US007186879B2

(12) United States Patent
Moore et al.

(10) Patent No.: US 7,186,879 B2

(45) Date of Patent: Mar. 6, 2007

(54) SCREENING SYSTEMS AND METHODS FOR IDENTIFYING MODULATORS OF XENOBIOTIC METABOLISM

(75) Inventors: David D. Moore, Bellaire, TX (US); Ping Wei, San Diego, CA (US); Steven S. Chua, Houston, TX (US)

(73) Assignee: Baylor College of Medicine, Houston, TX (US)

(*) Notice: Subject to any disclaimer, the term of this patent is extended or adjusted under 35 U.S.C. 154(b) by 71 days.

(21) Appl. No.: 10/268,822

(22) Filed: Oct. 10, 2002

(65) Prior Publication Data

US 2003/0150004 A1 Aug. 7, 2003

Related U.S. Application Data

(63) Continuation-in-part of application No. 10/219,590, filed on Aug. 15, 2002, and a continuation-in-part of application No. PCT/US01/29672, filed on Sep. 21, 2001.

(51) Int. Cl.
*A01K 67/00* (2006.01)

(52) U.S. Cl. .............................................. 800/8; 800/3

(58) Field of Classification Search .................. 800/18, 800/3; 435/325, 320.1
See application file for complete search history.

(56) References Cited

U.S. PATENT DOCUMENTS

| | | | | |
|---|---|---|---|---|
| 5,710,017 A | | 1/1998 | Moore et al. | |
| 6,693,226 B1 | | 2/2004 | McNeish | |
| 6,921,845 B1 | | 7/2005 | Amson | |
| 6,987,211 B1 | | 1/2006 | Soreq | |
| 2002/0152479 A1* | | 10/2002 | Lehmann et al. | 800/3 |

FOREIGN PATENT DOCUMENTS

| | | |
|---|---|---|
| WO | WO-99/15555 A1 | 4/1999 |
| WO | WO-00/47735 A2 | 8/2000 |
| WO | WO-01/51045 A2 | 7/2001 |

OTHER PUBLICATIONS

Oliver and Roberts. Pharmacology & Toxicology. 91:1-7, 2000.*
Wei et al. Nature 407:920-923, 2000.*
Bowie et al., 1990. Science, vol. 247, pp. 1306-1310.*
Ngo et al, The Protein Folding Problem and Tertiary Structure Prediction, 1994, Merz er (ed.), pp. 433&492-495.*
Cameron ER. Molecular Biotechnology 7:253-265, 1997.*
Wang et al. (2004) Human Constitutive Androstance Receptor Mediates Induction of CYP2B6 Gene Expression by Phenytoin. J. Biol. Chem. 279:29295-29301.*

(Continued)

*Primary Examiner*—Deborah Crouch
*Assistant Examiner*—Louis D Lieto
(74) *Attorney, Agent, or Firm*—Fulbright & Jaworski LLP

(57) ABSTRACT

The present invention provides mice having reduced CAR receptor activity and mice expressing a human CAR receptor. These mice are useful in screening methods to identify CAR ligands, including compounds that modulate CAR receptor activity, compounds likely to have CAR-mediated toxicity, and analogs of these compounds with less potential toxicity.

14 Claims, 25 Drawing Sheets

1 Kb
H3
H3
H3
CAR locus
1 2 3
4 5 6 7 8
9
Targeting vector
A
H3
H3
X
S
N
β-gal
neo
Mutated locus
A
H3
H3
X
S
N
H3
β-gal
neo
3' probe

OTHER PUBLICATIONS

Leiter et al. (2002) Mice with targeted gene disruptions or gene insertions for diabetes research:problems, pitfalls, and potential solutions. Diabetologia 45:296-308.*

Houdebine. (2000) Transgenic animal bioreactors. Transgenic Research. 9:305-320.*

Kolb et al. (1999) Insertion of a foriegn gene into the beta-casein locus by Cre-mediated site-specific recombination. Gene 227:21-31.*

Sigmund, C., (2000) Arterioscler. Thromb. Vasc. Biol., p. 1425-1429.*

Lariviere et al. (2001) J. Pharm. And Exp. Therap. 297:467:473.*

Oliver, J.D. et al. Receptor-medicated hepatocarcinogenesis: role of hepatocyte proliferation and apoptosis. Pharmacology & Toxicology 2002, vol. 91, pp. 1-7, see the entire document.

Xie W. et al. Reciprocal activation of xenobiotic response genes by nuclear receptors SXR/PXR and CAR. Genes & Development 2000, vol. 14, pp. 3014-3023, see the entire document.

Robertson, G.R. et al. Transgenic mouse models of human CYP3A4 gene regulation. Molecular Pharmacology 2003, vol. 64, No. 1, pp. 42-50, see the entire document.

Xie, W. et al. Humanized xenobiotic response in mice expressing nuclear receptor SXR. Nature Jul. 27, 2000, vol. 406, pp. 435-439, see the entire document.

Xie, W. et al. Control of steroid heme, and carcinogen metabolism by nuclear pregnane X receptor and constitutive androstane receptor. Proceedings of the National Academy of Sciences, USA, Apr. 1, 2003, vol. 100, No. 7, pp. 4150-4155, see the entire document.

Wei, P. et al. The nuclear receptor CAR mediates specific xenobiotic induction of drug metabolism. Nature Oct. 19, 2000, vol. 407, pp. 920-923, see the entire document.

Huang, Wendong, et al.: Induction of bilirubin clearance by the constitutive androstane receptor (CAR); PNAS 100(7):4156-4161, Apr. 1, 2003.

Baes et al., "A New Orphan Member of the Nuclear Hormone Receptor Superfamily that Interacts with a Subset of Retinoic Acid Response Elements," Molecular And Cellular Biology 14(3):1544-1552 (1994).

Blumberg et al., "SXR, a Novel Steroid and Xenobiotic-Sensing Nuclear Receptor," Genes Dev., 12:3195-3205 (1998).

Bornheim, "Effect of Cytochrome P450 Inducers on Cocaine-mediated Hepatoxicity," Toxicology And Applied Pharmacology 150:158-165 (1998).

Carthew et al., "The Quantitative Distinction of Hyperplastic in Hepatomegaly Induced in the Rat Liver by Phenobarbital," Toxicological Science 44:46-51 (1998).

Choi et al., "Differential Transactivation by Two Isoforms of the Orphan Nuclear Hormone Receptor CAR," The Journal of Biological Chemistry, 272:23565-23571 (1997).

Code et al., "Human Cytochrome P4502B6: Interindividual Hepatic Expression, Substrate Specificity, and Role in Procarcinogen Activation," Drug Metabolism And Disposition 25(8):985-993 (1997).

Cunningham, "Role of Increased DNA Replication in the Carcinogenic Risk of Nonmutagenic Chemical Carcinogens," Mutation Research 365:59-69 (1996).

Heubel et al., "Differences between Induction Effects of 1,4-bis[2-(3,5-dichloropyridyloxy)]Benzene and Phenobarbitone," Biochemical Pharmacology 38:1293-1300 (1989).

Honkakoski et al., "Characterization of Phenobarbital-inducible Mouse Cyp2b10 Gene Transcription in Primary Hepatocytes," The Journal of Biological Chemistry 271(16):9746-9753 (1996).

Honkakoski et al., "The Nuclear Orphan Receptor CAR-Retinoid X Receptor Heterodimer Activates the Phenobarbital-Responsive Enhancer Module of the CYP2B Gene," Molecular And Cellular Biology 18(10):5652-5658 (1998).

Jones et al., "The Pregnane X Receptor: A Promiscuous Xenobiotic Receptor that has Diverged during Evolution," olecular Endocrinology 14(1):27-39 (2000).

Kliewer et al., "An Orphan Nuclear Receptor Activated by Pregnanes Defines a Novel Steroid Signaling Pathway," Cell 92:73-82 (1998).

Lehmann et al., "The Human Orphan Nuclear Receptor PXR Is Activated by Compounds that Regulate CYP3A4 Gene Expression and Cause Drug Interactions," J. Clin. Invest. 102(5):1016-1023 (1998).

Moore et al., "Orphan Nuclear Receptors Constitutive Androstane Receptor and Pregnane X Receptor Share Xenobiotic and Steroid Ligands," The Journal Of Biological Chemistry 275(20):15122-15127 (2000).

Pellinen et al., "Regenerative changes in Hepatic Morphology and Enhanced Expression of CYP2B10 and CYP3A During Daily Administration of Cocaine," Hepatology 23(3):515-523 (1996).

Poland et al., "1,4-Bis[2-(3,5-Dichloropyridyloxy)]Benzene, a Potent Phenobarbital-like Inducer of Microsomal Monooxygenase Activity," Molecular Pharmacology 18:571-580 (1980).

Robinson et al., "Genetic Expression of Aryl Hydrocarbon Hydroxlase Induction. Presence or Absence of Association with Zoxazolamine, Diphenylhydantoin, and Hexobarbital Metabolism," Molecular Pharmacology 10:484-493 (1974).

Selim et al., "Hepatotoxicity of Psychotropic Drugs," Hepatology 29(5):1347-1351 (1999).

Shimada et al., "Interindividual Variations in Human Liver Cytochrome P-450 Enzymes Involved in the Oxidation of Drugs, Carcinogens and Toxic Chemicals: Studies with Liver Microsomes of 30 Japanese and 30 Caucasians," The Journal Of Pharmacology And Experimental Therapeutics 270(1):414-423 (1994).

Sueyoshi et al., "The Repressed Nuclear Receptor CAR Responds to Phenobarbital in Activating the Human CYP2B6 Gene," The Journal Of Biological Chemistry 274(10):6043-6046 (1999).

Traber et al., "Differential Regulation of Cytochrome P-450 Genes along Rat Intestinal Crypt-villus Axis," Am. J. Physiol. 263:G215-223 (1992).

Tzameli et al., "The Xenobiotic Compound 1,4-Bis[2-(3,5-Dichloropyridyloxy)]Benzene Is an Agonist Ligand for the Nuclear Receptor CAR," Molecular And Cellular Biology 20(9):2951-2958 (2000).

Waxman, "P450 Gene Induction by Structurally Diverse Xenochemicals: Central Role of Nuclear Receptors CAR, PXR, and PPAR," Archives of Biochemistry And Biophysics 369(1):11-23 (1999).

Zhang, Jun, et al.; Modulation of Acetaminophen-Induced Hepatotoxicity by the Xenobiotic Receptor CAR; Science, vol. 298, pp. 422-424, Oct. 11, 2002.

Waxman, David J.; Minireview—P450 Gene Induction by Structurally Diverse Xenochemicals: Central Role of Nuclear Receptors CAR, PXR, and PPAR; Archives of Biochemistry and Biophysics, 369(1):11-23, 1999.

* cited by examiner

Figure 1A
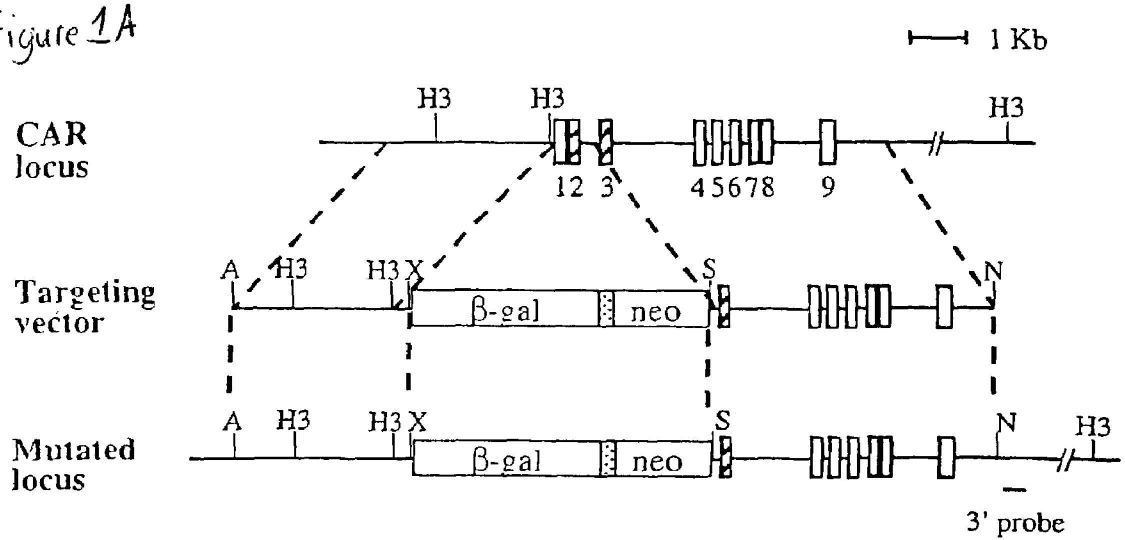
Figure 1B
Figure 1C
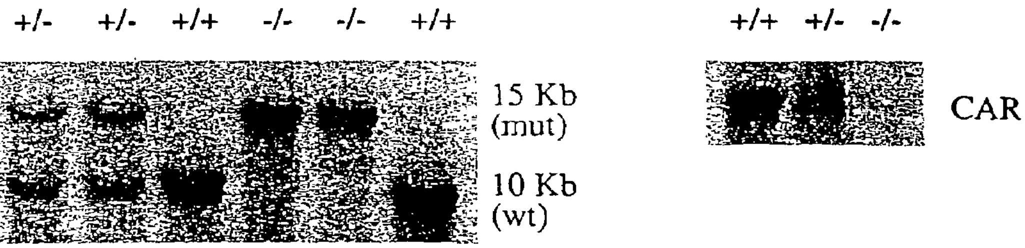
Figures 1A-1C

Fig. 5A
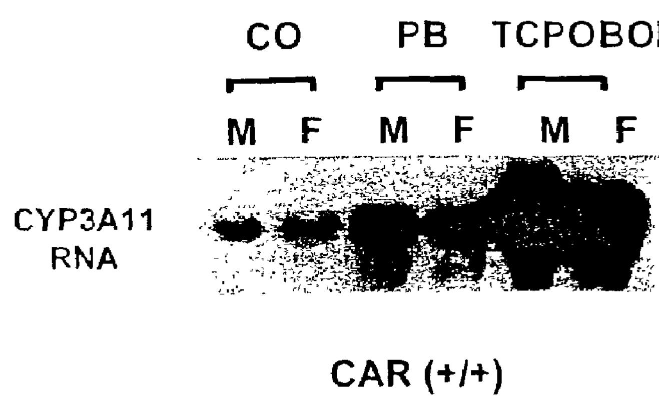
Fig. 5B
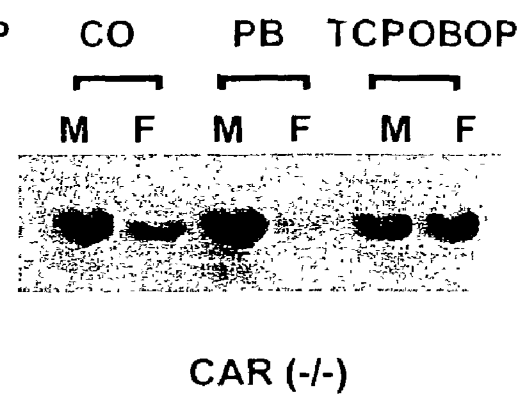
CO - control
PB - phenobarbital treated
TCPOBOP - TCPOBOP treated
M - male, F - female
Figures 5A and 5B

A

B

```
GTGAGCTTGC TCCTTAAGTT ACAGGAACTC TCCTTATAAT AGACACTTCA TTTTCCTAGT

CCATCCCTCA TGAAAAATGA CTGACCACTG CTGGGCAGCA GGAGGGATGA TAATCCTAAC

TCCAATCACT GGCAACTCCT GAGATCAGAG GAAAACCAGC AACAGCGTGG GAGTTTGGGG

AGAGGCATTC CATACCAGAT TCTGTGGCCT GCAGGTGACA TGCTGCCTAA GAGAAGCAGG

AGTCTGTGAC AGCCACCCCA ACACGTGACG TC

ATG GCC AGT AGG GAA GAT GAG CTG AGG AAC TGT GTG GTA TGT GGG GAC
Met Ala Ser Arg Glu Asp Glu Leu Arg Asn Cys Val Val Cys Gly Asp
1               5                   10                  15

CAA GCC ACA GGC TAC CAC TTT AAT GCG CTG ACT TGT GAG GGC TGC AAG
Gln Ala Thr Gly Tyr His Phe Asn Ala Leu Thr Cys Glu Gly Cys Lys
            20                  25                  30

GGT TTC TTC AGG AGA ACA GTC AGC AAA AGC ATT GGT CCC ACC TGC CCC
Gly Phe Phe Arg Arg Thr Val Ser Lys Ser Ile Gly Pro Thr Cys Pro
        35                  40                  45

TTT GCT GGA AGC TGT GAA GTC AGC AAG ACT CAG AGG CGC CAC TGC CCA
Phe Ala Gly Ser Cys Glu Val Ser Lys Thr Gln Arg Arg His Cys Pro
    50                  55                  60

GCC TGC AGG TTG CAG AAG TGC TTA GAT GCT GGC ATG AGG AAA GAC ATG
Ala Cys Arg Leu Gln Lys Cys Leu Asp Ala Gly Met Arg Lys Asp Met
65                  70                  75                  80

ATA CTG TCG GCA GAA GCC CTG GCA TTG CGG CGA GCA AAG CAG GCC CAG
Ile Leu Ser Ala Glu Ala Leu Ala Leu Arg Arg Ala Lys Gln Ala Gln
                85                  90                  95

CGG CGG GCA CAG CAA ACA CCT GTG CAA CTG AGT AAG GAG CAA GAA GAG
Arg Arg Ala Gln Gln Thr Pro Val Gln Leu Ser Lys Glu Gln Glu Glu
            100                 105                 110

CTG ATC CGG ACA CTC CTG GGG GCC CAC ACC CGC CAC ATG GGC ACC ATG
Leu Ile Arg Thr Leu Leu Gly Ala His Thr Arg His Met Gly Thr Met
        115                 120                 125

TTT GAA CAG TTT GTG CAG TTT AGG CCT CCA GCT CAT CTG TTC ATC CAT
Phe Glu Gln Phe Val Gln Phe Arg Pro Pro Ala His Leu Phe Ile His
    130                 135                 140

CAC CAG CCC TTG CCC ACC CTG GCC CCT GTG CTG CCT CTG GTC ACA CAC
His Gln Pro Leu Pro Thr Leu Ala Pro Val Leu Pro Leu Val Thr His
145                 150                 155                 160

TTC GCA GAC ATC AAC ACT TTC ATG GTA CTG CAA GTC ATC AAG TTT ACT
Phe Ala Asp Ile Asn Thr Phe Met Val Leu Gln Val Ile Lys Phe Thr
                165                 170                 175
```

FIG. 18
(PAGE 1 OF 2)

```
AAG GAC CTG CCC GTC TTC CGT TCC CTG CCC ATT GAA GAC CAG ATC TCC
Lys Asp Leu Pro Val Phe Arg Ser Leu Pro Ile Glu Asp Gln Ile Ser
            180                 185                 190

CTT CTC AAG GGA GCA GCT GTG GAA ATC TGT CAC ATC GTA CTC AAT ACC
Leu Leu Lys Gly Ala Ala Val Glu Ile Cys His Ile Val Leu Asn Thr
        195                 200                 205

ACT TTC TGT CTC CAA ACA CAA AAC TTC CTC TGC GGG CCT CTT CGC TAC
Thr Phe Cys Leu Gln Thr Gln Asn Phe Leu Cys Gly Pro Leu Arg Tyr
    210                 215                 220

ACA ATT GAA GAT GGA GCC CGT GTG GGG TTC CAG GTA GAG TTT TTG GAG
Thr Ile Glu Asp Gly Ala Arg Val Gly Phe Gln Val Glu Phe Leu Glu
225                 230                 235                     240

TTG CTC TTT CAC TTC CAT GGA ACA CTA CGA AAA CTG CAG CTC CAA GAG
Leu Leu Phe His Phe His Gly Thr Leu Arg Lys Leu Gln Leu Gln Glu
                245                 250                 255

CCT GAG TAT GTG CTC TTG GCT GCC ATG GCC CTG TTC TCT CCT GAC CGA
Pro Glu Tyr Val Leu Leu Ala Ala Met Ala Leu Phe Ser Pro Asp Arg
            260                 265                 270

CCT GGA GTT ACC CAG AGA GAT GAG ATT GAT CAG CTG CAA GAG GAG ATG
Pro Gly Val Thr Gln Arg Asp Glu Ile Asp Gln Leu Gln Glu Glu Met
        275                 280                 285

GCA CTG ACT CTG CAA AGC TAC ATC AAG GGC CAG CAG CGA AGG CCC CGG
Ala Leu Thr Leu Gln Ser Tyr Ile Lys Gly Gln Gln Arg Arg Pro Arg
    290                 295                 300

GAT CGG TTT CTG TAT GCG AAG TTG CTA GGC CTG CTG GCT GAG CTC CGG
Asp Arg Phe Leu Tyr Ala Lys Leu Leu Gly Leu Leu Ala Glu Leu Arg
305                 310                 315                     320

AGC ATT AAT GAG GCC TAC GGG TAC CAA ATC CAG CAC ATC CAG GGC CTG
Ser Ile Asn Glu Ala Tyr Gly Tyr Gln Ile Gln His Ile Gln Gly Leu
                325                 330                 335

TCT GCC ATG ATG CCG CTG CTC CAG GAG ATC TGC AGC TGA GGCCATGCTC
Ser Ala Met Met Pro Leu Leu Gln Glu Ile Cys Ser
            340                 345

ACTTCCTTCC CCAGCTCACC TGGAACACCC TGGATACACT GGAGTGGGAA

AATGCTGGGA CCAAAGATTG GGCCGGGTTC AAAGGGAGCC CAGTGGTTGC AATGAAAGAC

TAAAGCAAAA C
```

FIG. 18
(PAGE 2 OF 2)

```
     Mouse CAR
     cttgttttccaggcactgaggaccgcagtccctaattcctggcagttcctgagatctcaa
   1 ---------+---------+---------+---------+---------+---------+ 60
     gaacaaaaggtccgtgactcctggcgtcagggattaaggaccgtcaaggactctagagtt

     ggaaagcagggtcagcgaggaggcctggggagaggaggcatcctacacccaatcttgtgg
  61 ---------+---------+---------+---------+---------+---------+ 120
     cctttcgtcccagtcgctcctccggacccctctcctccgtaggatgtgggttagaacacc

     cctgctgcctaagggaaacaggagaccatgacagctatgctaacactagaaaccatggcc
 121 ---------+---------+---------+---------+---------+---------+ 180
     ggacgacggattccctttgtcctctggtactgtcgatacgattgtgatctttggtaccgg
                                  M  T  A  M  L  T  L  E  T  M  A

     agtgaagaagaatatgggccgaggaactgtgtggtgtgtggagaccgggccacaggctat
 181 ---------+---------+---------+---------+---------+---------+ 240
     tcacttcttcttatacccggctccttgacacaccacacacctctggcccggtgtccgata
       S  E  E  E  Y  G  P  R  N  C  V  V  C  G  D  R  A  T  G  Y

     catttccacgccctgacttgtgagggctgcaagggcttcttcagacgaacagtcagcaaa
 241 ---------+---------+---------+---------+---------+---------+ 300
     gtaaaggtgcgggactgaacactcccgacgttcccgaagaagtctgcttgtcagtcgttt
       H  F  H  A  L  T  C  E  G  C  K  G  F  F  R  R  T  V  S  K

     accattggtcccatctgtccgtttgctggaaggtgtgaggtcagcaaggcccagagacgc
 301 ---------+---------+---------+---------+---------+---------+ 360
     tggtaaccagggtagacaggcaaacgaccttccacactccagtcgttccgggtctctgcg
       T  I  G  P  I  C  P  F  A  G  R  C  E  V  S  K  A  Q  R  R

     cactgtccagcctgcaggttgcagaagtgtctaaatgttggcatgaggaaagacatgata
 361 ---------+---------+---------+---------+---------+---------+ 420
     gtgacaggtcggacgtccaacgtcttcacagatttacaaccgtactcctttctgtactat
       H  C  P  A  C  R  L  Q  K  C  L  N  V  G  M  R  K  D  M  I

     ctgtcagcagaagccctggcattgcggcgagccagacaggcacagcggcgggcagagaaa
 421 ---------+---------+---------+---------+---------+---------+ 480
     gacagtcgtcttcgggaccgtaacgccgctcggtctgtccgtgtcgccgcccgtctcttt
       L  S  A  E  A  L  A  L  R  R  A  R  Q  A  Q  R  R  A  E  K

     gcatctttgcaactgaatcagcagcagaaagaactggtccagatcctcctgggggcccac
 481 ---------+---------+---------+---------+---------+---------+ 540
     cgtagaaacgttgacttagtcgtcgtctttcttgaccaggtctaggaggacccccgggtg
       A  S  L  Q  L  N  Q  Q  Q  K  E  L  V  Q  I  L  L  G  A  H

     actcgccatgtgggcccattgtttgaccagtttgtgcagttcaagcctccagcctatctg
 541 ---------+---------+---------+---------+---------+---------+ 600
     tgagcggtacacccgggtaacaaactggtcaaacacgtcaagttcggaggtcggatagac
       T  R  H  V  G  P  L  F  D  Q  F  V  Q  F  K  P  P  A  Y  L

     ttcatgcatcaccggcctttccagcctcggggccccgtgttgcctctgctcacacacttt
 601 ---------+---------+---------+---------+---------+---------+ 660
     aagtacgtagtggccggaaaggtcggagccccggggcacaacggagacgagtgtgtgaaa
       F  M  H  H  R  P  F  Q  P  R  G  P  V  L  P  L  L  T  H  F
```

FIGURE 19 (PAGE 1 OF 3)

```
      gcagatatcaacacgtttatggtgcaacagatcatcaagttcaccaaggatctgccgctc
 661  ---------+---------+---------+---------+---------+---------+ 720
      cgtctatagttgtgcaaataccacgttgtctagtagttcaagtggttcctagacggcgag
        A  D  I  N  T  F  M  V  Q  Q  I  I  K  F  T  K  D  L  P  L

      ttccggtccctaaccatggaggaccagatctcccttctcaagggagcggctgtggaaata
 721  ---------+---------+---------+---------+---------+---------+ 780
      aaggccagggattggtacctcctggtctagagggaagagttccctcgccgacacctttat
        F  R  S  L  T  M  E  D  Q  I  S  L  L  K  G  A  A  V  E  I

      ttgcatatctcactcaacactacgttctgtcttcaaacagagaatttcttctgtgggcct
 781  ---------+---------+---------+---------+---------+---------+ 840
      aacgtatagagtgagttgtgatgcaagacagaagtttgtctcttaaagaagacacccgga
        L  H  I  S  L  N  T  T  F  C  L  Q  T  E  N  F  F  C  G  P

      ctttgctacaagatggaggacgcagtccatgcagggttccagtacgagtttttggagtcg
 841  ---------+---------+---------+---------+---------+---------+ 900
      gaaacgatgttctacctcctgcgtcaggtacgtcccaaggtcatgctcaaaaacctcagc
        L  C  Y  K  M  E  D  A  V  H  A  G  F  Q  Y  E  F  L  E  S

      atcctccacttccataaaaacctgaaaggactgcatctccaggagcctgagtatgtgctc
 901  ---------+---------+---------+---------+---------+---------+ 960
      taggaggtgaaggtatttttggactttcctgacgtagaggtcctcggactcatacacgag
        I  L  H  F  H  K  N  L  K  G  L  H  L  Q  E  P  E  Y  V  L

      atggctgccacggccctcttctcccctgacagacccggagttacccaaagagaagagata
 961  ---------+---------+---------+---------+---------+---------+ 1020
      taccgacggtgccgggagaagaggggactgtctgggcctcaatgggtttctcttctctat
        M  A  A  T  A  L  F  S  P  D  R  P  G  V  T  Q  R  E  E  I

      gatcagctacaagaggagatggcgctgattctgaacaaccacattatggaacaacagtct
1021  ---------+---------+---------+---------+---------+---------+ 1080
      ctagtcgatgttctcctctaccgcgactaagacttgttggtgtaataccttgttgtcaga
        D  Q  L  Q  E  E  M  A  L  I  L  N  N  H  I  M  E  Q  Q  S

      cggctccaaagtcggtttctgtatgcaaagctgatgggcctgctggctgacctccggagt
1081  ---------+---------+---------+---------+---------+---------+ 1140
      gccgaggtttcagccaaagacatacgtttcgactacccggacgaccgactggaggcctca
        R  L  Q  S  R  F  L  Y  A  K  L  M  G  L  L  A  D  L  R  S

      ataaacaatgcatactcctatgaacttcagcgcttggaggaactgtctgctatgacgccg
1141  ---------+---------+---------+---------+---------+---------+ 1200
      tatttgttacgtatgaggatacttgaagtcgcgaacctccttgacagacgatactgcggc
        I  N  N  A  Y  S  Y  E  L  Q  R  L  E  E  L  S  A  M  T  P

      ctgctcggggagatttgcagttgaggcccaggcttgcatcctttccccagacccccaggg
1201  ---------+---------+---------+---------+---------+---------+ 1260
      gacgagcccctctaaacgtcaactccgggtccgaacgtaggaaaggggtctgggggtccc
        L  L  G  E  I  C  S  *
```

FIGURE 19 (PAGE 2 OF 3)

```
     atacactggcctggaaagggtacagcgctggaccccacacgggaaccagcaggaaggagc
1261 ---------+---------+---------+---------+---------+---------+ 1320
     tatgtgaccggacctttcccatgtcgcgacctggggtgtgcccttggtcgtccttcctcg

     ttgggagtggcaatgaaatgctgaacagtcaaaaaaaaaaa
1321 ---------+---------+---------+---------+- 1361
     aaccctcaccgttactttacgacttgtcagttttttttttt
```

FIGURE 19 (PAGE 3 OF 3)

```
     1                                              2
mCAR1  1 MTAMLTLETMASEEEYGPRN CVVCGDRATGYHFHALTCEGCKGFFRRTVSKTIGPICPFA   60
hCAR     ..........  R D.EL      Q        H                     S   T

                                     3
    61 GRCEVSKAQRRHCPACRLQKCLNVGM RKDMILSAEALALRRARQAQRRAEKASLQLNQQQ   120
        S     T                DA                      K      QQTPV  SKE

                              4
   121 KELVQILLGAHTRHVGPMFDQFVQFKPPAYLFMHHRPFQPRGPVLPLLTHFADINTFMVQ   180
       E  IRT         M T  E    R  H  I  Q LPTLA      V            L

                 5
   181 QIIKFTKDLPLFRSLTMEDQISLLKGAAVEILHISLNTTFCLQTENFFCGPLCYKMEDAV   240
        V       V    PI                 C  V         Q  L   R TI  CA

           6                                         7
mCAR1                                                GFCMQS
   241 HAGFQYEFLESILHFHKGLKGLHLQEPEYVLMAATALFSFDRPGVTQREEIDQLQEEMAL   300
       RV    V      LLF    GT RK Q           L  K               D

                   8
   301 ILNNHIMEQQSRLQSRFLYAKLMGLLADLRSINNAYSYELQRLEELSAMTPLLGEICS    358
        T QSY KG   R PRD        L     E       E  G QI HIQG      K   Q
```

FIG. 20A

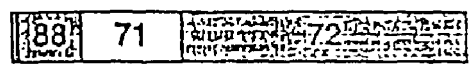

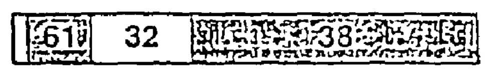

FIG. 20B

SEQUENCE LISTING

```
<160> NUMBER OF SEQ ID NOS: 27

<210> SEQ ID NO 1
<211> LENGTH: 358
<212> TYPE: PRT
<213> ORGANISM: Mouse

<400> SEQUENCE: 1

Met Thr Ala Met Leu Thr Leu Glu Thr Met Ala Ser Glu Glu Glu Tyr
1               5                   10                  15

Gly Pro Arg Asn Cys Val Val Cys Gly Asp Arg Ala Thr Gly Tyr His
            20                  25                  30

Phe His Ala Leu Thr Cys Glu Gly Cys Lys Gly Phe Phe Arg Arg Thr
        35                  40                  45

Val Ser Lys Thr Ile Gly Pro Ile Cys Pro Phe Ala Gly Arg Cys Glu
    50                  55                  60

Val Ser Lys Ala Gln Arg Arg His Cys Pro Ala Cys Arg Leu Gln Lys
65                  70                  75                  80

Cys Leu Asn Val Gly Met Arg Lys Asp Met Ile Leu Ser Ala Glu Ala
                85                  90                  95

Leu Ala Leu Arg Arg Ala Arg Gln Ala Gln Arg Arg Ala Glu Lys Ala
            100                 105                 110

Ser Leu Gln Leu Asn Gln Gln Gln Lys Glu Leu Val Gln Ile Leu Leu
        115                 120                 125

Gly Ala His Thr Arg His Val Gly Pro Leu Phe Asp Gln Phe Val Gln
    130                 135                 140

Phe Lys Pro Pro Ala Tyr Leu Phe Met His His Arg Pro Phe Gln Pro
145                 150                 155                 160

Arg Gly Pro Val Leu Pro Leu Leu Thr His Phe Ala Asp Ile Asn Thr
                165                 170                 175

Phe Met Val Gln Gln Ile Ile Lys Phe Thr Lys Asp Leu Pro Leu Phe
            180                 185                 190

Arg Ser Leu Thr Met Glu Asp Gln Ile Ser Leu Leu Lys Gly Ala Ala
        195                 200                 205

Val Glu Ile Leu His Ile Ser Leu Asn Thr Thr Phe Cys Leu Gln Thr
    210                 215                 220

Glu Asn Phe Phe Cys Gly Pro Leu Cys Tyr Lys Met Glu Asp Ala Val
225                 230                 235                 240

His Ala Gly Phe Gln Tyr Glu Phe Leu Glu Ser Ile Leu His Phe His
                245                 250                 255

Lys Asn Leu Lys Gly Leu His Leu Gln Glu Pro Glu Tyr Val Leu Met
            260                 265                 270

Ala Ala Thr Ala Leu Phe Ser Pro Asp Arg Pro Gly Val Thr Gln Arg
        275                 280                 285

Glu Glu Ile Asp Gln Leu Gln Glu Glu Met Ala Leu Ile Leu Asn Asn
    290                 295                 300

His Ile Met Glu Gln Gln Ser Arg Leu Gln Ser Arg Phe Leu Tyr Ala
305                 310                 315                 320

Lys Leu Met Gly Leu Leu Ala Asp Leu Arg Ser Ile Asn Asn Ala Tyr
                325                 330                 335

Ser Tyr Glu Leu Gln Arg Leu Glu Glu Leu Ser Ala Met Thr Pro Leu
            340                 345                 350

Leu Gly Glu Ile Cys Ser
```

```
        355


<210> SEQ ID NO 2
<211> LENGTH: 348
<212> TYPE: PRT
<213> ORGANISM: Human

<400> SEQUENCE: 2

Met Ala Ser Arg Glu Asp Glu Leu Arg Asn Cys Val Val Cys Gly Asp
1               5                   10                  15

Gln Ala Thr Gly Tyr His Phe Asn Ala Leu Thr Cys Glu Gly Cys Lys
            20                  25                  30

Gly Phe Phe Arg Arg Thr Val Ser Lys Ser Ile Gly Pro Thr Cys Pro
        35                  40                  45

Phe Ala Gly Ser Cys Glu Val Ser Lys Thr Gln Arg Arg His Cys Pro
    50                  55                  60

Ala Cys Arg Leu Gln Lys Cys Leu Asp Ala Gly Met Arg Lys Asp Met
65                  70                  75                  80

Ile Leu Ser Ala Glu Ala Leu Ala Leu Arg Arg Ala Lys Gln Ala Gln
                85                  90                  95

Arg Arg Ala Gln Gln Thr Pro Val Gln Leu Ser Lys Glu Gln Glu Glu
            100                 105                 110

Leu Ile Arg Thr Leu Leu Gly Ala His Thr Arg His Met Gly Thr Met
        115                 120                 125

Phe Glu Gln Phe Val Gln Phe Arg Pro Pro Ala His Leu Phe Ile His
    130                 135                 140

His Gln Pro Leu Pro Thr Leu Ala Pro Val Leu Pro Leu Val Thr His
145                 150                 155                 160

Phe Ala Asp Ile Asn Thr Phe Met Val Leu Gln Val Ile Lys Phe Thr
                165                 170                 175

Lys Asp Leu Pro Val Phe Arg Ser Leu Pro Ile Glu Asp Gln Ile Ser
            180                 185                 190

Leu Leu Lys Gly Ala Ala Val Glu Ile Cys His Ile Val Leu Asn Thr
        195                 200                 205

Thr Phe Cys Leu Gln Thr Gln Asn Phe Leu Cys Gly Pro Leu Arg Tyr
    210                 215                 220

Thr Ile Glu Asp Gly Ala Arg Val Gly Phe Gln Val Glu Phe Leu Glu
225                 230                 235                 240

Leu Leu Phe His Phe His Gly Thr Leu Arg Lys Leu Gln Leu Gln Glu
                245                 250                 255

Pro Glu Tyr Val Leu Leu Ala Ala Met Ala Leu Phe Ser Pro Asp Arg
            260                 265                 270

Pro Gly Val Thr Gln Arg Asp Glu Ile Asp Gln Leu Gln Glu Glu Met
        275                 280                 285

Ala Leu Thr Leu Gln Ser Tyr Ile Lys Gly Gln Gln Arg Arg Pro Arg
    290                 295                 300

Asp Arg Phe Leu Tyr Ala Lys Leu Leu Gly Leu Leu Ala Glu Leu Arg
305                 310                 315                 320

Ser Ile Asn Glu Ala Tyr Gly Tyr Gln Ile Gln His Ile Gln Gly Leu
                325                 330                 335

Ser Ala Met Met Pro Leu Leu Gln Glu Ile Cys Ser
            340                 345


<210> SEQ ID NO 3
<211> LENGTH: 42
```

<212> TYPE: DNA
<213> ORGANISM: Artificial Sequence
<220> FEATURE:
<223> OTHER INFORMATION: Primer

<400> SEQUENCE: 3
gcgcgcgggc cctggcatac attaacacaa acacatacat at 42

<210> SEQ ID NO 4
<211> LENGTH: 42
<212> TYPE: DNA
<213> ORGANISM: Artificial Sequence
<220> FEATURE:
<223> OTHER INFORMATION: Primer

<400> SEQUENCE: 4
gcgcgctcta gaaggaccca gactctggac ccagggcaaa ga 42

<210> SEQ ID NO 5
<211> LENGTH: 42
<212> TYPE: DNA
<213> ORGANISM: Artificial Sequence
<220> FEATURE:
<223> OTHER INFORMATION: Primer

<400> SEQUENCE: 5
gcgcgcgtcg acaggtgaag tgcttctccc caacagaaac aa 42

<210> SEQ ID NO 6
<211> LENGTH: 42
<212> TYPE: DNA
<213> ORGANISM: Artificial Sequence
<220> FEATURE:
<223> OTHER INFORMATION: Primer

<400> SEQUENCE: 6
gcgcgcgcgg ccgctgtcct gggagcagcc tctgcagccg ct 42

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
ggacaacctc agcccacagt gatgc 25

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
tcctttggtt accacctgac tctgc 25

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9

-continued

```
ccgcctctag aagtcaacat tggttagac                                 29


<210> SEQ ID NO 10
<211> LENGTH: 29
<212> TYPE: DNA
<213> ORGANISM: Artificial Sequence
<220> FEATURE:
<223> OTHER INFORMATION: Primer

<400> SEQUENCE: 10

ccgccggatc ccacactaag cctcataat                                 29


<210> SEQ ID NO 11
<211> LENGTH: 1822
<212> TYPE: DNA
<213> ORGANISM: Mouse

<400> SEQUENCE: 11

accaggacca tggagcccag tgtgctgctc ctccttgctc tccttgtggg cttcttgcta     60

ctcttagcca ggggacaccc aaagtcccgt ggcaacttcc caccaggacc ccgtcccctg    120

cccctcttgg ggaacctctt gcagatggac agaggaggcc tcctcaagtc tttaattcag    180

cttcgagaaa aatatggcga tgtgttcaca gtgcacctgg gaccaaggcc tgtggttatg    240

ctgtgtggaa cagacaccat aagggaggct ctggtgggcc aagccgaggc tttctctggc    300

cgggggacag ttgctgtcgt tgagccaacc ttcaaggaat atggtgtgat ctttgccaat    360

ggggaacgtt ggaagaccct tcgtagattc tctctggcca ccatgagaga ctttgggatg    420

ggaaagagga gtgtggagga gcggattcag gaggaagccc aatgtttagt ggaggaactg    480

cggaaatccc agggagcccc cctggacccc acgttcctct tccagtgcat cacggccaat    540

gttatctgct ccattgtgtt tggagagcgc tttgagtaca cagaccgtca gttcttgcgc    600

ctgctggagc tgttctatca gaccttttca ctcataagct cattctccag ccagatgttt    660

gagctcttct ctggcttcct gaagtacttt cctggtgccc acagacaaat ctccaaaaac    720

ctgcaggaac tcctcgacta cattggccat agtgtggaga ggcacaaggc caccttggac    780

cccagtgttc cacgagactt cattgatatt taccttctgc gcatggagaa ggagaagtcc    840

aaccagaacg cagagttcca tcaccagaac ctcatgatgt ctgtgctctc tctcttcttt    900

gtcggcaccg agaccagcag caccacgctc cactatggct tcctgctcat gctcaagtac    960

ccccatgtta cagagaaagt ccaaaaggag attgatcagg tgatcggctc acaccggcta   1020

ccaacccttg atgaccgcac caaaatgcca tactcagatg cagtcatcca cgagattcag   1080

agattttcag atcttatacc tattggagtg ccacacagag tcaccaaaga taccctgttc   1140

cgagggtacc tgctccccaa gaacactgag gtgtacccca tcctgagttc agctctacat   1200

gatccacagt actttgaaca accagacagt ttcaatcctg accagttcct ggatgccaat   1260

ggggcactga agaaaagtga agcttttctg cccttctcaa caggacaaat tttgatcaa    1320

aagtctgtgg gaaagcgcat ttgtcttggt gaaagcattg cccgcagcga attgttcctt   1380

ttcttcacgt ccatcctcca gaacttctct gtggcaagcc atgttgctcc taaggacatt   1440

gacctcactc ccaaggagag tggtattgga aaaatacctc caacgtacca gatctgcttc   1500

ttggcccgct gattgggctg aggcagacag ggtcaccag taatgttgag aatgactctg    1560

tctttgagcc tctgagacag ctggtggaaa tcagtactcc tattgcatgt ctccaaatct   1620

ccagggctcc aaggcatgtt cttcttccct gtgaatggca ctggagaaat caatcaactg   1680

tctttcttga catgtgaaaa gagacttctg gagtccacat ctcatgttga gtcacttccc   1740
```

-continued

```
ttttcctccc aatagcccaa gtgtccactt atcagctccg catgatctgg gatctgtgct   1800

aatggactct gtataaggtc tg                                            1822
```

<210> SEQ ID NO 12
<211> LENGTH: 42547
<212> TYPE: DNA
<213> ORGANISM: Human

<400> SEQUENCE: 12

```
gatccagggg tctgccgtag atcttagcca tggactgcac ctggggctcc gtttgaagaa     60

ctatttgtag ttttacagct tcaattctgg aagagacaaa cttaacaagg aggttaaaga    120

cacagggatt gaaatgtctg gcctgaagtg caggggatta tttctttggc acacttcaca    180

ggccctgact acctgcttga tagttttgaa aaggcctggt ccagcaaata atgatttggc    240

cattggatgg gtgctatcaa cgcctaaatg aaaggtttgg tgaagggttt taagtaattt    300

ccattggtta gctgcaggca aaagtatttt tccttctttg gtggctagac atcctgaggg    360

gagggaacta tgtccttgtg aggtacccca ttctatttct tctgctgagc actggggctt    420

ggtttcctgg aggggattac cccatactag ggttccttct ataagcattt ctaatggagg    480

gtcccgcctt gtggctcttt ggcttcaata tctgcttggt ggttcccttc tatttccctt    540

tcctttcctt tctgatgacc ccagcagtgt aagatggcca cctctttagg tttccgtaca    600

gcccataata actcataatg gcttcctgat gtttaatagg tgttccctca gaagttagga    660

attccatttc tcaccatatt tttgtgtagg catggaggag aaggtaagca taattagagt    720

gtttatatat atttaccctt ttcccttctc ctaattctag tgtatcatgg cccctgcttt    780

tgctaggatg tctctcccta acaaaggagt ggggctttca ggcataatta gaaaggcatg    840

tgaaaagagt aaagtccccc agttacaact tagtggctgg gcgaagtaac tagtgactgc    900

ttgtcctagg acccctcgga tagtaacaga tctggaaatc cagctagtcc tgtctctcaa    960

aactacaatg ataaacaata agagaaaaag aaaggaagaa aggatataca tacataaaga   1020

agccaactaa taatatgaca ggattaagct ctcacatatc aataataacc ttgaattaaa   1080

tggattaaac tttccactta aaagaaagag actggctgaa tggatttaaa aagcatgacc   1140

cagctatatg ctgcctacaa gaaacacatc tcaccaggaa agacatatat agtgaaagta   1200

aagaaatgag aaaagatatt ccatgcaaat aaaaaccaaa agtgagcagc aatacctatg   1260

tttataaagg aaacagactt taagtcaaaa actgtaaaaa gagacaaaga aggtcaatac   1320

ataatgataa aaggatcaat cgagcaaagg atccatgagg aaattcctgc ctaataaatt   1380

ttggtcagac cggttgtctg ctctcaaacc ttgtctcctg ataagatgtt atcaatgaca   1440

atgcttgccc gaaacttcat tgcaatttta atttcacccc ggtcctgtgg tcctgtgatc   1500

tcgccctgcc tccatttgcc ttgttatatc ttattacctt gtgaagcatg tgatctctgt   1560

gacctacacc ctattcgtac actccctccc cttttgaaaa tcactaataa aaactttctg   1620

gttttacggc tcagggggca tcatggaacc tgccgacatg tgatgtctcc cccggacccc   1680

cagctttaaa atttctctct tttgtgctct gtccctttat ttctcaggct ggccgacact   1740

tagggagaac agaaaagaac ctacgtggaa tattgggggt gaattttgcc cgatatctgg   1800

ctgaatttcc cctgataatg ccactctcta tgtccatgtg tacacattgt ttagcaccca   1860

cttatgaatg agaacatgtg atattcactt tctgtgcctg gcttgtttca cttaagataa   1920

tcccctccag ttgtatccat gttgctataa aagacattat tttattcctt tttatggcta   1980
```

-continued

```
aatagtattc aatggtgtat atataccaca ttttatttaa ccattcatct gttgattccc   2040
tatttttgct attgtaaata gcatttggac cacatttcaa gtacttaatt agtggccaca   2100
tgcagcaagt gactatcaca ttggacaatg tagccccaac ccactgtatg accttgggta   2160
agacttgcaa actgtcattg cttcaatatc tccatctata aaatggggat ggcaacaata   2220
cctcactaag agtgtaaaga ctgagttact gtgtgtaaag cacttcacgc ctccccatcg   2280
gtgcttcacc ctggggctgc aatgagcacc caatcttagt gtcagatgac acagcacagc   2340
aagaccgagg cccttggttc aggaaagtcc atgctgccac ctcttcaggg tcaggaaagt   2400
acagtttcca cctcttacaa ataggactgt ttgtctgctc ctcctgggtc aaagtaactt   2460
cgggttcagg tcctggatcc agcaaagggt ttgcttaaca ttgcaagaaa gatgttgcct   2520
catggtcaaa agtcaggcgt aggatgagac aggcagacac gcacacattc acacccacgt   2580
tttgcaaaga tggactgacc ctgtcagagg atgtgtgggt gaaggtgcac agtgaggata   2640
gagacatatg ggagtccagt agacatcaat caaactggac tcagtttgca cacacctgga   2700
gctcaagagt ctccaggggg aaaacagaga cacaaagtca gacagagaga gagccagaga   2760
aatttcctgc accgtgaaga tagtcagagg cagggaagaa actccttagc actagttaga   2820
gtgatcagaa accaagagga cctgatcgct gtacctgcca ggtctcagtt tctgtctcct   2880
tccaactgac cacctcttcc tctgagactc accagttctg catctcttgc tcctccttct   2940
gtttctccga ccacttccac ctgtggctgt cacagaaggg cggatgaagg aggggacact   3000
ggagatagac tcagcatctg caggcttcca aagagagggg ctaggagatc caccaacaca   3060
ccagcacaaa tacaccagca cacacagata cacacaattg gttcatgtat tgctaggtta   3120
cagtttgcta tgctacaaag gcagtaggcc aaatttgatt gaattgaata attccttatt   3180
ttcatcagct tctccttttt tttttttttt tttttttttt gagatggagt attgctgtgt   3240
cacccaggct ggagtgcagt ggtgtaatct tggctcactg cagcctccac ctcccaggtt   3300
caagtgattc tcttgcctca gcctcccgag tagctgggat taaaagtacc caccatcacg   3360
cccggttaat tttttgtttt ttagtacaga tggggttttg ccatgtgggc caggatggtc   3420
tcgaactctt gacctcaatt gatctgcccc cctcagcttc ccaacgtgct gggattacag   3480
gtgtgagcca ccgcacccag ccagcctctc agttttgaac atgcactacc accacctcca   3540
caacacacaa atgtaaatgc actttcgtat ataaaactgt ataaatacaa ggaagctcat   3600
acacatgcaa ggatacacac ataagcaccc ccagattcaa ccacagaaat atacgccagt   3660
acatttgcat aaattcaaac accccctttac atgtaaaaat catataagca catacaggga   3720
tgcaagcagg catggacaaa tgcatgcaag cacagacaaa cagacaaagc taagtaaaaa   3780
agtgcaagct cacctatgct tacaaaaata gacatacata tacccacaaa cccacacacc   3840
cacacattca cttgctcacc tggactttga tatctctacc actgtatccc tgccaatatc   3900
tacagagtgg gtaaagggat aggcatcagg tcactgggtt gcccaagcag gaagtctggg   3960
ttccctaaca actttttcta agctaatgct cctggatgat gatgaaaaag gaggtgggga   4020
atggatgaaa ttttataaca gggtgcagag gcagggtcag gataaaaggc ccagttggag   4080
gctgcagcag ggtgcagggc agtcagacca ggaccatgga actcagcgtc ctcctcttcc   4140
ttgcactcct cacaggactc ttgctactcc tggttcagcg ccaccctaac acccatgacc   4200
gcctcccacc agggccccgc cctctgcccc ttttgggaaa ccttctgcag atggatagaa   4260
gaggcctact caaatccttt ctgagggtaa gacacagacg aatggggtct gagggtgagc   4320
tgcttcttgc cttggtactt ggggaagctt caccaaacag aatgaggcag acttccagag   4380
```

-continued

```
tcaggggtgg cacgggcatg gttggtgagt acggagcatg gtgaagcatg atgggtggta   4440
ttattaggag aaaagcatca aattaaattt agcagagttt atttgagcaa agaagtgact   4500
catgagttgg acagctccct aaaccaggaa agacaccaca cggcagtatg gtcaagtggt   4560
atttacaggc agaaaaagga ggtgacatac agaaacagcc tgattggcca cagatcacag   4620
cttgccttac ttggtcacaa tctgagcagt ttgcagcctg tgtggactga aagcccagct   4680
gctctgatta gccaacactt ggctacttgt cacaagaata tattcatttg ggccaggtgc   4740
agtggctcat gcctgtaatc ccagtgcttt tggaggccga ggtggtggat cacctgaggt   4800
caggagttcg agaccagcct ggccaacatg gtgaaacctt gtctctacta aaaatacaaa   4860
tattagctgg gcatagtgat gcgtgcctgt aatctcagct acccaggagg ctgaggaagg   4920
agaatcactt gaatccagga ggcagaggtt gcagtgagcc aaaatcttac cactgcactc   4980
catcctgggt gacagagtga gactccttct caaaaaaaaa aaaaaaaaaa agaatatact   5040
cccaagttag gttgcagttc actctacaga gagagcttta ggtcaaattt aatttaatta   5100
aacaattctc cccttttggt cagcctcaaa attttgagat tgaccaaaac cttgggcatc   5160
aacattactt ctgtcaccat cataatggac ttgtctgctc tcagtatgga attcacaatg   5220
gacaatgtca acgtagttga gtgattcttt accttttctt catgtttttg ttgttcccac   5280
tgtaatgagc ccactggatg tacaaagaat ggctgcatat gagcatttaa gactcttttt   5340
ttttctgaga cagggcctca ctctgtcagc caggctgaag tgctgtggca tgatcacgtc   5400
tcactgcagc cttgacctcc caaggctcaa gtgatcctcc tgcctcagcc ccccaagtag   5460
ctggaactac aggtgcatgc caccacgccc agctaatttt tgtatttttt gtagagacag   5520
ggttttgcca tgttgcccag actggtctta aactcctggg ctcaagcaat ccacctgcct   5580
cggcctccca aagtgctagg attacatgtg tgagccaccg cacccggcca agactcttga   5640
gaaaatacaa cacatcaggg agactgttat gatggctctc aggagggtaa tacgaagaaa   5700
atgaagtcac tgggcctgta ataaactttg aggaatgtgg acttggggggt atagataagg   5760
tccactgtcc acagagagaa gaaaggctgt taatagtctc ttttaacttg agtgtgtcca   5820
tgaaccaaac tgatcaaaat cgaataattc gaagttcaga caataaagat agttcaatag   5880
tattagagtc caattggtca tagattttgt tcagggcatg atggtaatta aggaccagag   5940
cttgctataa aataacttga tttatagaga cattcatttg tagttggcct ggtaacatat   6000
agtatcctgg agacccacta gaagaaacat taagagtaga aaagtttggg atagccaggc   6060
ttgctgtgtt agtccattct cacactgtta taaagacata cctgagactg ggtaatttat   6120
aaacaaaagg gatgtaactg actcacagtt ccacatggct ggggaggccc caggaaaata   6180
caattcatgg caaaaggtga atgagaagca ggaaacttac aatcatgatg gaaggtgaag   6240
gagaagcaag taccttcttc acaaggtggc aggaaaaaga gagagagcca agggggaaga   6300
gcctcttata aaaccatcag atcttgtgag aactcactca ctatcacaag aacagcatgg   6360
gggaaaccgc ccccaggatc cagttacctc ctactaggtc cttccctcca cacctgggga   6420
ttacaattca agatgagatt tgggtgagga cacagagcca aaccatatca cttaccatca   6480
ccattcagga tgcttgcaaa ccaactgcta gctgcacctg taaacacata tctgtttctt   6540
tcccctgaga aatgtcctta gtgtatttgt ggcagtgtct agagaaacag cagtgtcagc   6600
cgcattttaa attaagttat ctgcactagt gaattcactg gaaagataag agcaatattt   6660
ggttttcttc agcaccatac acaagcctcc aagatgggca tagaggagat ctaaaattgc   6720
```

-continued

```
gtgatgttcc attaagcgtt tttgttgcca caaatgttct catctcagtt tggagagtgg   6780
cttctaccca tctgaactcc ttggaggttc aattagctgc aaaattcaag atgtccctta   6840
atgtataact tagcctcaga ttccatacaa ctgtcaccca aataccacca agaatgagca   6900
cccaggaacc caactggaac cttttctgaa cagaaaccaa cttatcttcg tcgattttga   6960
ggttgatagt aatttcagtt attgactgtt ttggctttta actatgggag gtattaggaa   7020
actctcaggg aaacaatttg gaaagcagca gtgagctagg ccaaatagca agttctggac   7080
ctgtgaggag aaagaacaga gtaagcaaac ctcaagatac tcaaggtagg cactcgtggt   7140
gttggaaaag agggtcacct actggcatta gagcagagat cagttagatt tgtttaccca   7200
taagtctgca tagctcctga acaaggtggg aaacttactt ttttgtggtc tttttctagc   7260
atgctgcgaa ggtgcataac cacatttagt tggaaagaga ctttactgta tttacttatt   7320
tatttgtttt taatagagtt ggggtcgtgc tatgttgaac tcttggcctc aagcaatcct   7380
cccatctcaa tctcccaaag tgctgggatt acaagcatga gccaccatgc ctggccactt   7440
tacatattta atccagtaac attacacacg caattgccca cacccccata ggtagtcccc   7500
aggtcttgca tacgggatgc ctggaagcaa aatatgcctt ttgcagccat tattcagata   7560
catttcctat atttagtagt gattatgtta ttagctagtt aatagtatgt tattacgtac   7620
tgttattata ttaactaact aataacataa tcactactaa atatttccag tgagtgcaaa   7680
aaagcaagtg gcaatgatgt ctagaatatc aagatatagc tttccactcc tcctttgggg   7740
tttctgggtg attctcattg ggaacatgaa gaggcattgg caccagtgaa attatttcct   7800
gattttgggg cgttggttca gaaactcaac aactccttgt ttttttgtt tgtttgcttg   7860
ttttgctaga gtataagcct ttgctaaagc cattcacaga ttatagtcct atggattttc   7920
ttgtaaggaa agggaaaggg ttaggacagc aagaaatggg gaagaaagga taaaagataa   7980
tgctttcatg atggaagaga aatcttgatc cacaatcttg gaaaagctgt ccgcatataa   8040
gatgccaact gcttctgggg aaaaacttcc ctggtcagct ttgccttaag gtctccaaca   8100
gacatacagt tctaggagtc tagaagggtc ctttccaatg gagagatgtg gatccaagat   8160
ccgagaccct gacattttgc tacagagaag aacttggcat tgtccttccc aatggagtac   8220
aaggaacagt cttagaagaa cttggtacgg tctcttccaa tggagttcaa ggacagtttg   8280
tctggtgtca tttccaaagg gcccaacctc taaattctag atcatgaaag gtctggttgt   8340
catcaaccga tgtgtcatca atgactcatt ttacctggtg aaaacatgct ttggcataaa   8400
gtattatagc cttgcattat tgagtcatat cagagtttat aagagtggga gatacatgag   8460
attctattat taggggcata ggccctctat tactatttta caagagatct atctatgtct   8520
ttccagtagg agtggatctg attgccatca atcaataata cctgagacca agggactcca   8580
atcaattcag catgctttgc ctaatgatat ttgtttgtaa tactgttgcg ggacaatcaa   8640
agactggaga gaccaaaaaa ggttcaggag agtttattaa attaaggtga tcaccggttc   8700
agccagacat acatccagaa agtctgagcc ccgaacaaag gcttttccta cttttaaaca   8760
tattaaggtg ggaactacat gaggcaggaa gccagtttca gaagtgagaa acaaagcagt   8820
taaataacat ttcttacatc ttgagaaaga catgtcttgc aacctaacct tatcggtccg   8880
gtgaccctgc agctgtgcag gaactcactg ggcctgtaat aaactttgag ggatgtggag   8940
ttggggagta taggtaaggt ccactgtcca cagagagaag acaggctgtt aatattctct   9000
tttaacttga atgtaaggtg tggtcatact ttgcagcaac cttaagagga ttttaaaatt   9060
tatattacta ctactattag gttatagttg atttcattaa ttccttcttc aataccttat   9120
```

-continued

```
ttaactgttt taccacttgt ctagtgaaac aagtacctct gtcactggag agttctccag   9180
gaatgcccag taaggaaata cattttctaa taacctttta tctacggtta tggcattgat   9240
tgatctttgt gcatagaaat gctttaatac aaccagaaaa catgcaatga agctggcagt   9300
tgaattaact ccagcttcaa gtgttcaaat gatctaccaa gtgccagaaa tatatcacct   9360
gaggtttttg ttgtcttact agaattatgg atttgataaa ccaaatatta gttataaacc   9420
atttagtaat cttagaatag tcacctcatc aatatttttt cactgtttgg atcattttct   9480
ctcttctatg atgagtcatg gaatacggag cttttagtaa tggaaatttt aagaactcag   9540
gaaggaccag gcggccatct agggtctcca tgagtgcatg cttcacattg gaattacaga   9600
ctctaaagta caaattttaa tacaatgagt tgcaatttat gcttctctaa ttcaggtaca   9660
taacactggt ttattaaata ggttatcata ggtaatttga tggtgccatt gcactccagc   9720
ctgggtaaca gattgagacc ctgtctctga attggaactg cacgggggca ctgtccttgg   9780
aggggtgaat gggcatgaag aggtgtctgg gtatgagcca caggtataga atttcactct   9840
tctctgccat cctctgttac atcctgggta cctgcctgcc actgaaagaa tgaggtaaaa   9900
gaggtggtgg cacgaatcaa atagatcttg ctgtgccaat gagagagagc agactagccc   9960
atgtcagtgc caggagagtg gaggagagag ggagagcagg agaggagtgt gggtagggag  10020
tgctcatcaa cagtacacat agtgccctat accggtaact gccactggct cagtatttac  10080
ctgggttatc actgcttacc atgcctgatt ttatgattaa ttatctactt atcattacta  10140
atccatcaac ccactttcca atgggagaat tagaacactg acaatacctt ccagctcctc  10200
ttccccttcc ccctcccatg ttgaccatac tcctgaatct taggctcgtt atccttttac  10260
tattaataga gttatttttt taatttctga tcaatggtct ttttaatgat accaagtaca  10320
gagtatatat gccaatacta ctatgaattt ttaaattatt tgctcagaca gaatacatgg  10380
acatacaaat gatgaatgtg ataattgtca tacatatata tttatcttag acacttagtc  10440
aaaacatgtg gtctttggtt atcagttaga cactgtcact ttacctggaa gatacaaggt  10500
aattggtcac agactctcaa attatgaaac atttagattt ttcaggggaa tgacatggag  10560
ggagccaagg agtcttatga ttagataaga tgttgtttgg gtggctcacg acaccactgg  10620
gcaacactca aagaggtggt ggcttatacc tgtaatccca acactttggg aggctgaggt  10680
gggaggatcg cttgaagcca ggagttagaa accagcctgg gcaaccaaac aagacctggc  10740
tctacaaaaa agttttaaaa atttagccag gcatggtggc atgtgcctgt agtcccagct  10800
acttgggaga ctgaggcagg aggatgactt gagccttgta gtttgaggct gcagtgagct  10860
atgatcacgt cactgccctc cagcctgggc acagagcaag accctgtctc ttaaaaaaaa  10920
atcatctgca atgtgaggag tgataacatt taggaacgtg tgtataggtt taaatgctgg  10980
tcaaagacat cctacacaat tcgctgaacc ttctctctaa gggtttttttc ccaagctctg  11040
cagacgctat ctgggcacaa atcatgcctc tgttaacaga atttgctgtt ccttctagct  11100
cttggtatcc cactgcccgc tttctttatg aaagctggta tggtcattga atatcccaat  11160
cctttacaaa tttggaaaca agcaaaactg tcaatgaaat ttgtatttgc ctaaaatgag  11220
ttttctttct ttcttttta ttattattat actttaagtt ttagggtaca tgtgcacatt  11280
gtgcaggtta gttacatacg tatacatgtg ccatgctggt gcgctgcacc cactaactcg  11340
tcatctagca ttaggtatat ctcccaatgc tatccctccc ccctccccc accccacaac  11400
agtccccaga gtgtgatgtt tcccttcctg tgtccatgtg atctcattgt tcaattccca  11460
```

-continued

```
cctatgagtg agaatatgtg gtgtttggtt tttttgttct tgcgatagtt tactgagaat  11520
gatgatttcc aatttcatcc atgtccctac aaaggacatg aactcatcat tttttatggc  11580
tgcatagtat tccatggtgt atatgtgcca cattttctta atccagtcta tcattgttgg  11640
acatttgggt tggttccaag tctttgctat tgtgaataat gccgcaataa acatacatgt  11700
gcatgtgtct ttatagcagc atgatttata gtcctttggg tatataccca gtaatgggat  11760
ggctgggtca aatggtattt ctagttctag atccctgagg aatcgccaca ctgacttcca  11820
caatggttga actagtttac agtcccacca acagtgtaaa agtgttccta tttctccaca  11880
tcttctccag cacctgttgt ttcctgactt tttaatgatt gccattctaa ctggtgtgag  11940
atggtatctc attgtggttt tgatttgcat ttctctgatg gccattgatg ttgagcattt  12000
tttcatgtgt tttttggctg cataaatgtc ttcttttgaa aagtgtctgt tcatgtcttt  12060
cgcccacttt ttgatggggt tgtttttttc ttgtaaattt gtttgagttc attgtagatt  12120
ctggatatta gccctttgtc agatgagtag gttgcgaaaa ttttctccca ttttgtaggt  12180
tgcctgttca ctctgatggt agtttctttt gctgtgcaga agctctttag tttaattaga  12240
tcccatttgt caattttgtc ttttgttgcc attggttttg gttttttaga catgaagtcc  12300
ttgcccatgc ctatgtcctg aatggtaatg cctaggtttt cttctagggt ttttatggtt  12360
ttaggtctaa cgtttaagtc tttaatccat cttgaattga ttttgtatac taaaatgagt  12420
tttcaaaagg atctttgtgg ctaccttatt agttcataga aagtggaggc ttgtctggaa  12480
tgatattaaa gaattttttt cattttaatt gttttagaga cagggtctca gtctgttacc  12540
caggctggag tacaatggca cagtcatagc tcactgcagc cttgaactcc tgtgctcagg  12600
agattctccc accttagcct ccagagtagc tgggactaaa agtgtgagcc accatgcccc  12660
actatttatt tttgtagaga tgtgtttggg ggacggtctc actatgttgc ctaggctggt  12720
ctcgaactcc tggactcaag caatcctcct gcctcaacct cccaaagcat tgggataagt  12780
tttgcataga catgtttgac cctctccctt cctttattgc agcaaagatt tccattttct  12840
cacagggagg acttggggca aattgttttt gtcgttgtta ttgttatttg aggatgtggg  12900
tgggtcatct tggttaatgt cagtgcaaga acggtgtctg ctcctcatta ttggggttcc  12960
ttagctattc aggcaggcag cagctccctt gagaagactt cctgaccccc aggtccccat  13020
catatgctct catacaccag ctgcccctcc ttactgagcc tatgtccttg atagtgctgc  13080
atttacctgt gatcctgtgg ctgagctctc cctcacactt ccagacaagg aaggcctgtg  13140
aggtatcagc acagtgctga acatagtacc tggtacacaa taggcattta gtaaatatgt  13200
gaacaggaac aaatgaagga gtcagtgagt gaaagctcca agcctgactc agcggaactg  13260
gcagtcggcc agggcctaca aagtgctgcc tggccctcag taggggtgg cagatctggg  13320
gatccctctt caccaaatag agttgcatca tacaggtaaa ggtcccaagt gcctattgtt  13380
ttcttttcat catttccat gtgtgacaag agtatcacgc aatcatgtga atcaatggac  13440
ttagttttct cactagacta atgtgtctag gaattatctg tgttgtcatg gggattttcc  13500
aggtgtcatt tacaactacc tgtggacaag atgaggtgct accctcatct tagaattagg  13560
gatggtggct gggcatggca gcccatgcct ataatctcag cactttggga ggctgaagca  13620
ggtggatcaa ctgaggtcgg gagttcgaga ccaacctgac caacatggag aaaccctgtc  13680
tgtactaaaa aacacaaaac tagctgggca tggtggcaca tgtctgtaat cccagctact  13740
cgggaggctg aggcaggaga attgcttgaa cccaggaggc ggagtttgcc ctgagctgag  13800
attgcatcat tgcactccat catgggcaac aaaagtgaaa ctccatctca aaaaaaaccc  13860
```

-continued

```
aaacagaaac aaacaaacaa acaaaattag tgatagtgat gctcagcctg gggaaagcat  13920
ttgtccagtg gcacacaact gggaaaaggg gaagctgaga tccagcagga ggtctgtctc  13980
caaagccctc ctagactaaa gctgcttaac aatttgtgga ttatgaaatt ctcatagagt  14040
ttgattaaag ctgtggcccc ctcttttcca aataggcaca tacatgtttg cataaagttg  14100
tgaggcttca cacactccct aaaactcttt cataaacctt ccaaggatcc tctaggtatt  14160
cacgaccatc tattatgatt gcatctcttg ggggtggggt aaagagggag ggcatgagca  14220
agtgtgcatc agggctgagg aaggtggcgc tgttgcttct ccatttccca ataagcttcc  14280
agattctttt tgatgtcaga gggatgtggg ctcgtgtctc agattcaacc cgtatgcatt  14340
gagtcacagt tttctcttcc gtcagttaag atcatgacaa tgagaatgtg tgcccctaag  14400
gtggttgtga ggattaaatg ggatattgca tacagctagt atataataag tgctcattaa  14460
atggcaacta ccttgatcca ctcattcatt tattcacgaa tccaataaca attcactggg  14520
cactttctat gtaccaggaa atagtctagg aattgatgat gtggcatctt ggacaagaca  14580
tacgaggtca ctgcgcttat ggacattcca ttggcagaga cagataagca aaaaataaac  14640
agataaggaa atgttaggtg gagaagagct acaattaaac taaagcaggg ggatatttca  14700
gacagtgatg agaactacgt tagattgagt ggttagggga agactgtctt gttttttttt  14760
ctgagcagag acaatgaaag attcaggtgg aaggcactag aaggaggcag ggtggctac   14820
aagaatcctg aaacaggaaa aatgtcagag aacaacatgg aggaatgagt gggaggagaa  14880
gtcagagcgg taatagggcc acgtcatgta ggaccatgtg aaccctcagt ggagacttca  14940
gatcttattc tcagcaaagt gggaatattg taggccttgg tgagcacgtg gatattaatt  15000
attttacatt ttagtggggt taccctggct tgtggggcag tgaaacaatt gttaagtgga  15060
gtaagcatgt catccagaag tccagtgaag gggctttgca gagatcaatg cagggcattt  15120
gtaagtaaac ttaacaaatt ttatgacttt tatgtcaagt ttttattgaa cttgaacatc  15180
actgtaaaaa gcgcacagct caatgaattt tcacaaactg aacatactca tgtaattgac  15240
atgcaggcca agtagcaaga atgccccgaa accctgcacc ctgttctttt ctattcacta  15300
tccacctacc atcttgatca tgggttgatt ttatctgtgt atgaacttct tttttgtttt  15360
tgtttgtttg ttcctgagat tgaattttgc tctgtcgccc aggctggagt gcagtggcac  15420
tatctcgcct cactgcaacc tccgcctccc cgggctcaag caattctctc gtctcagcct  15480
cccgagtagc tgggactaca ggtgagagcc accatgcctg gctaattttt gtatttttag  15540
tagagatggg ttttcaccat gttggtcagg ctggactcaa actcctgacc tcgtgatcag  15600
cctgcctcag cctcccaaat tgctgggatt acagatgtga gtcaccacgc ctggccctgt  15660
gtttgaactt catacacata aaattatgat gcattgactc ttttgtgcct agttgcttcc  15720
actcaacatt atgcctgtga gtttcagcca cgttgtcgcc tgtagctgtg gtttgttctt  15780
ttttgttgct gtatactagt ctattgtgag aaccctcact gattgtctat atctatattg  15840
atgagcattt tattaagaaa gcttctgtga atattttgtt catttttttgg tgaacacaca  15900
tacacatttt tgctgggcat gtacctggga gtgaagtggc tggtttcctg ggtatccatt  15960
tgttcagctt caggaaatac tgcccagcag ttccccaagt ggctgcacag taatcccacc  16020
ttatccactg gagatatctt ctgagacccc cagtggatgc ctgaaacccc acataatact  16080
gagcactatg catactcttt ttttttccta tacaatcaca ttatataggg agggtggtat  16140
acacagtgca gacatggtgg acaaaggatg attcgtgtcc ggggtgggac agagtggatg  16200
```

-continued

```
gtgagagata tcatcatcct actcagaatg atgcacaact taaaacttac gaattcttta  16260
tttctggaat tttccattta atattttcag actgcgatta gctgcaggta actgaaactg  16320
caaaaagcaa aaccacagat cataagaagt atgcggtggg ggtgatattc atcgtatttt  16380
atcaaccatc tttactgttt agggcacaag ccaatcagag cagaccctgg ctgggccacc  16440
cattaaccta agcttgtcca acctgcctta ttttgttgtt gttctgtttt gttttgtttt  16500
agctttttag cagcctgaag ccatggtttt cagtttctgt ctccagtgat acacagaaag  16560
gaaggatgag gaaggggctt tactggccca accagaaacg gaaactaaga acccatgact  16620
gtattctctc ccttggacag cgttaaccat taacccttaa ttgctgggtc ccagcagggg  16680
aaagggcagc ctggggaggc ggatgttggg gaggggctaa ttaccaatct ggtatgtaag  16740
tattttgata gttttacaaa tgaggtgtat gctgactaac agccacccct ggtgtggatg  16800
tgattggcag ttccgagaga aatatgggga cgtcttcacg gtacacctgg gaccgaggcc  16860
cgtggtcatg ctgtgtggag tagaggccat acgggaggcc cttgtggaca aggctgaggc  16920
cttctctggc cggggaaaaa tcgccatggt cgacccattc ttccggggat atggtgagag  16980
cctcagaggc actgggaggg ggcgggtggg gggtgcatca gggaagggag tatatgggag  17040
gaagaaggac tcagagcctt cttccaactt cttctacaac caacccacac ctcccctgca  17100
ccccaggtgt gatctttgcc aatggaaacc gctggaaggt gcttcggcga ttctctgtga  17160
ccactatgag ggacttcggg atgggaaagc ggagtgtgga ggagcggatt caggaggagg  17220
ctcagtgtct gatagaggag cttcggaaat ccaagggtga gtcctggggg atgaatagga  17280
aagaaagaca atgaaacact gagagatgca ggtgcacggg aatagaaaga cagagaggta  17340
tataagggca cagacagaga cagacgaaac tggagacacc atcagacaga gggatagaga  17400
cagagaggga gagagacagg ggaatagaga gggatgggga tgggcaggag agaaacacag  17460
agagccaggg aaagagagag atgccaggtg tataatgtcc aagagttact caaagaggct  17520
ggatgtgatg actctcacct gtaatcccag tactttggga agctcaggca ggaggattgc  17580
ttgaggccaa gagttggaga acagcctggg caacataatg agatcctgtc tctacacaat  17640
atagaaaaga agtgagccac gcatggtggt gtgtgcctgt agtcccagct actcaggagg  17700
ctaaggtggg actacaggat cacttgagcc caggaggttg aggttgcagt gagctgtgat  17760
tgtaccactg cactccagcc tggacaacag agcaagatcc tgtctcaaac aaacaaacaa  17820
accctcaaag acatataatt tcatggatca attgtgtctg tcaaagtcaa aaacggaagt  17880
taagtaaaag aaaaaaacta cagacattta acaaataatg aactgtgttt tccttgccct  17940
gggtgaagtg ctgatgagct ggcagtgagc agacaggcca ggtggggtgt tctgcccggg  18000
tgcagctgga ggggtcatca aagaatcact aggttatttt tgagttctcc ataacttggt  18060
gtctgtgaga catgtaggtg aagggtctct ggctagcacc tccatctcat tcatgccagg  18120
tgtttaccat ctctcttatc aaaatttctc aagagactct gggatgtaaa tgcagaggct  18180
gcatggggag gtagagaccc aggagctata gggaaacggg gacaagaaga ctgaagagaa  18240
ggacaggaag aaacagtgac acaggcagga ggaaagagac agatggaggg accaaaacaa  18300
aaaaatatag gttgggtatg gggctcatgc ctgtaatccc agcactttgg gaggctgagg  18360
ctggcggatc atttgaggcc agcagttcaa aaccagcctg gccaacatgg tgaaacccca  18420
tctgtgctaa aaatacaaaa attagccagg cttggtagca cgtgccttta atcccagcta  18480
ctcaggaggc tgagacagga gaattgattg agcctgggaa atggaggttg ccgtgagcta  18540
agatcacact actgcactcc agtctgcatg atagagtgag actctgtctc caaaaataat  18600
```

-continued

```
aataataata ataaaataaa gaacggcagg ggggagacaa atatacacac agagagacag 18660
aaagaaacaa aggcaaagag aaattgaggc agagaaaatt agagagacag acagacaaag 18720
cttaggaaaa ggtctgcaga ggaatgagag aagacaggca agtgagaacc agagagaggc 18780
tgcactaacc tgatgttctt gggtccttac agaccactct ccctccagct ggggccagtg 18840
ctgagcctgg tgtatacagg tatcacttaa caagtacaga ataattccca gaagactgga 18900
gagccctaga tgtggaaaga agagattaag gggagtaat aggtaggggt ggaaagatgg 18960
tttttattt gttttaaatt agagacgggg tctcactctg tacccaggct ggagtgcagt 19020
ggcacgatca tagctcactg cagcctcaaa ctcctgggcc catgtgatcc tcccacttca 19080
gcccctggac tatttcaact gggactacag gcatgtgcca ccatgtctag ctacattttt 19140
ttttttttt ttttgtagag acagggtctc cttatgttgc ccaggctggt cttgaattcc 19200
tgatcctttt gaatcaggct cccgaagtgc tgggtttaga ggtatgggcc cctgtgccca 19260
cccagggctt tttaatttat ataagcaatt gattgaacac ctactctgcc cagcccctat 19320
ccctgggatt taactgtact cactcccaga gtcagaggtg gggcctgaga ggaggtgcag 19380
agtgagaacc ggctgcatgg actctatagc tgtgttgcct gggtctaaat cctggcctca 19440
gtaatgagta gctgtgcaac tttggtcaaa ttactcagcc tctcggtctg cccatctata 19500
aactggagct aataatcaaa ttgcatctgc ctcacattgt tgtagtgaga gttcaatgga 19560
attacgcgtg acgtgctggt acataattag ctgttacggt tattctcatg tttaccatta 19620
ctgagtgatg gcagacaatc acacagagat aggtgacagc ctgatgttcc ccaggcactt 19680
cagtctgtgt ccttgacctg ctgcttcttc ctaggggccc tcatggaccc caccttcctc 19740
ttccagtcca ttaccgccaa catcatctgc tccatcgtct ttggaaaacg attccactac 19800
caagatcaag agttcctgaa gatgctgaac ttgttctacc agactttttc actcatcagc 19860
tctgtattcg gccaggtcag ggagacggag agggacaggg ggtgtggggg tgaggtgaac 19920
acccagaaca cacgagaaaa ggatgacctg tcttgggggc tcagaaatgc agcttatcct 19980
tggaagaaac gcagacatgt gaagaatcag ggacatggag acctggaggg aggagagacg 20040
gtgagacagg gatagagaca ctgagagaga gaatgaggcg tgatggggag gcagaaatag 20100
agtcagagag agactgagag aaggaagatg agcaaaaaca agacaaagaa gagcagaaat 20160
caagagattc tgagagacag agttgatgag aatgagtgtg aaagagaggg agagagagag 20220
aacgaataag gctttgggct tcatgtctat tctgctcctg gatgtcattt ctgttttatt 20280
ttttttagac ggagtctcgc tgtttcattc cagctggggt gtagtgttgc catcttggct 20340
tactgcaacc tccacctccc gggttcaagt gattctcctg cctcagcctc ccaagtagct 20400
gggactgcag gcatgtgcca ccacacctgg ctaatttttt ttttttctt ttcgagacag 20460
agcctcgctc tgttgcctag gctggagtgc agtggcacaa tctcagctca ctgcaacttc 20520
cacctccctg gttcaagcaa ttcccctgcc tcagcctcct gtagctggga ttacaggcgc 20580
ctgccgctat gccaggctaa tgtttttgta tttttagtag agacggggtt tcgccatgtt 20640
ggccaggctg gtctctaact cctgacctca agtgatctgc ccgcctcaga ctcctaaagt 20700
gctggaatta caggtgtgag ccaccatgcc cagactgctt ctggttcttc tgtatccttg 20760
cttctcagtc tttggtaaag ctctccacct aaagaaaatg aaggataaat gacaataagg 20820
aacagcattt cttcattttc tcccatttct ccttctccct ctgtgttttt ttttttaact 20880
ttccccagat tgtaaaggca gtcttctgct cttttaaaac aaaatactaa aatgtctcct 20940
```

-continued

```
tatttattaa cctggaaata tgcctattac atattaaatt taagaatatc aagctgcaga  21000
acagtatgca tagctgtagt ttgttgttgt tgttgttttc agacagtatc ttgctctgtt  21060
actcaggctg gagtgcagta gtgtgatctc aactccctgc cacctccacc tcccaggttc  21120
aagcaattct catggctcag cctcccgagc agccgggact ataggcgagc gccaccacac  21180
ccagctaatt tttttgtatt tttagtagag atggtgtttc accatgtcgg ccaggctggt  21240
caacatagct acagctatta agcagggatg tatgttggat tcacatgtgg ggttgtcaca  21300
gttatggatt ttcaggaccc tactttctgg gcggtctgat ctggaaagtc tgggatgggg  21360
cccaaggtga gtacttgtaa caagcccgac cagtaattct aatgttctcc tcccaccgag  21420
aaccacagag aaaagtctgg aaggagaccc accagacagt taacaatggt tatctctaga  21480
aggagagatt aagaaggaaa tttacatctg actatatatg tttgcatttt tgcaattatt  21540
tgcaataaat taggcattcc attcttcatc aaagtaatag aaataacctc caaaatacgt  21600
agtcctaaca tgtcagcagg cttatcttgt gtaagaatca ttttattaat atctgacaca  21660
gcaagggaga tgaggagagg tgggaagagg gagagaaaag tatgagaaag acaaataaac  21720
aggctgaggt agacaatggg tgacacagaa aggaagtgag acagagacta agagagatag  21780
aaaggagaga ggcagggaga tggggcagag gccaagaaaa agacagaagg atgagggagg  21840
aagatgcaga aagaggtaaa tgtgagatag atcaaaggag atatagagtc agtgagtgag  21900
gggttcagag gcagagggga gtggggaagt ggggttccca tggagggatt ggggcccagg  21960
aggcgctctc tccctgtgac ctgctagctc agccctaggc aaacctcacc accccttctt  22020
tcttgcagct gtttgagctc ttctctggct tcttgaaata ctttcctggg gcacacaggc  22080
aagtttacaa aaacctgcag gaaatcaatg cttacattgg ccacagtgtg gagaagcacc  22140
gtgaaaccct ggaccccagc gcccccaagg acctcatcga cacctacctg ctccacatgg  22200
aaaaagtggg gtctgggaga ggaaaaaggg aagggagggg agggagggca agatggagag  22260
gtgagaagag ggagggaaaa ggggtaggga aggggaagat ggggagggaa gaagaaagac  22320
tagggagggg agaataggga aagggaggag agaacatgag gaaggaaaga aagatgaggt  22380
gaaaggaggg agaaaatagg gaggaggaac tgagacaggg agagagggga ggtgggaaga  22440
cagaatgaaa gacagaggga gagagagaga agactggctg aggaaggaat tcggggcaag  22500
ggacaaaaat acagcaacaa gagaaaaaac tcacagaggc agaaagagac ggggacaaaa  22560
agagagaaac acatcaaaga gatgtggaga gagatagaaa cagagttagg aagactaaag  22620
agaggctgag agagatgagt tagagatacg cggttggatg tgtagaggac agagaaaagc  22680
aaactgggcc agatagtgtc aaagaccttt aggccaacgg agggcagcca gggagatggg  22740
cgtatacaca gcaaggctac agcctcccct gaccctcccc ttccttccct actgtggacg  22800
caggagaaat ccaacgcaca cagtgaattc agccaccaga acctcaacct caacacgctc  22860
tcgctcttct ttgctggcac tgagaccacc agcaccactc tccgctacgg cttcctgctc  22920
atgctcaaat accctcatgt tgcaggtggg ccagggacag ccagtcaagg gggtcttctg  22980
acctccttct gagctgcaga aatggggcta tgggtaccac ctggatgaga gaggggatgc  23040
tggcttccta ttctgggagc actgtaggct ctgggctaga ttccaaccaa gccaattctg  23100
ttggtggatg catggatgca tgaagaatct gtccatgcgt tctcccactg ttttcttcca  23160
tcacttaagg attttttgtt ctaaggtttt tgtttgtttg tttgtttttt gttttttggt  23220
tttttttttt ttgtcttttt tgagacagag tctcgctctg tcacccaggc tggagtgcag  23280
tggcatgctc ttggcttact gcaagcttca cttccagggt tcacgccatt ctcctgcctc  23340
```

```
agcttcccga gtagctggaa ctacaggcgc ctgccaccac acccggctaa tttttgtgt  23400
ttttagtaga gatggggttt aaccatgtta gccaggatgg tctcgatctc ctgacctcat  23460
gatgtacaaa tttaggggt acatatgcag ttttgttaca tgcgtaggtt ttgtaatggt  23520
caagtttggg ctgttagggt atttatcacc caaacagtgt acattgtacc cattaagtaa  23580
tttctcatca ttcacccccc ttctgctccc tcactcttct gagtcttcac tgtgtatcat  23640
tcctctctct gtgtccatgt gtacacattt tgtagcactc actcatgagt gagaacatgc  23700
aatatttgac tttctgtgcc atcacttaaa aatcgatcca tccacttatc atttcatcta  23760
ttcattcttt aattcattaa ttaaagaatg tataattact gattctttca tttatgattc  23820
atctaaggac atatactgtc attcatttat ttggattact tgatccacaa gttgatcctt  23880
tgaaacagtg gtatgttgat ggactatttg tcattgattc attggctcat tcattcattc  23940
attcatgcat tcatccatcc ttctacgaac taggtttcac tcttatcctt ccatgagtca  24000
acctttcaat tcacccttaa tccatccgtg atttccttca tttatcacaa taattcactc  24060
atttattcac ctctgatcta cttatcattc aatccagcct ttcatttact cctttattta  24120
ctcatacttc actaatttaa ttattcactt gctcttccat aaatctagcc attcatgtga  24180
ttattcatta attgggttca ttgatttctt tgtctatgga tcattcatta gtgattaatt  24240
aatcaatcca tctattaatt gataagtaaa tacagacatc catttattgg tttgttcatt  24300
tattcatcaa tctttccatc catgaattga tctattgatt gattgattga tgtttttatc  24360
cagttgttca tgaattcatc tattgttcta ttacactgtt atatacctga ggaccaagaa  24420
tagtgtctca actatattat aaacacaata aatattagtt cattttctac tcatcttaga  24480
gagggtgttt tgagaggttt gtagcctgga gttcttaatc tgaaattcca tgcaaaatcg  24540
tggtgtgtgt gtgcatgtgt gtgtgtgtac ctgggcatgt gggaagagga tctgtaatat  24600
tcattagatt tcaagcagtg agaattcttg ttgcttcctc cctcctcccc tcaccccatg  24660
ctgattactt tgaggggtat caaggatcta accctttact ataggttttt cattggtcaa  24720
tagaaagtag tgtccttgct gaaaggtctc tttttaaaaa aattttttttt tcttttgaga  24780
tggagtcttg ctctgtcacc cagtctagag tgcagtggca tgatctcggc tcactgcaac  24840
ctccacctcc tgggttcaag tgattctcct gcctcagcct cctgagtagc taggaataca  24900
ggtgtgcacc agcacaccca gctaattttt tgtattttta ggagagacgg gattttgcca  24960
tgttggccag gctcatcttg aactcctgac ctcaaggaat ccacccacct caacctccaa  25020
aattgctggg attacaggca tgagccacca tgcctggcct gaaatgcctc tttaaaatga  25080
gattcattgg tcttcttttc tgtacagaga gagtctacag ggagattgaa caggtgattg  25140
gcccacatcg ccctccagag cttcatgacc gagccaaaat gccatacaca gaggcagtca  25200
tctatgagat tcagagattt tccgaccttc tccccatggg tgtgccccac attgtcaccc  25260
aacacaccag cttccgaggg tacatcatcc ccaaggtaag accggctgga accccatagc  25320
cctcctgttt gggcatcctg gattctctta atccccgaac tcaacctttt gttagctcct  25380
taattgagtc ccgttgtttt tgttttttgt atttcttttt tgtggagtgt gtggagggtt  25440
ggagggaatg gcaatatctt ttgatcttgt gatcctccct caggacacag aagtatttct  25500
catcctgagc actgctctcc atgacccaca ctactttgaa aaaccagacg ccttcaatcc  25560
tgaccacttt ctggatgcca atggggcact gaaaaagact gaagctttta tccccttctc  25620
cttaggtaag ctggacccac aatttctttc ccagacacca gagggcaggt actatcccca  25680
```

-continued

```
acttgagaaa aacaacgaga gatactgatt atttgagcac ttaatatatt ctgattgctt  25740
cacctgcctt atcccattcc atcttcacta caaccctata aggaggcttg agaaagaaga  25800
ttacattccc aaaggcacat cttggcaagc aggaccttgg gcaagtattt taacatctct  25860
aaacctcagt gagttcattt tcttaaaaag aaaaaatctg ttgggcacca ctgtaagccc  25920
agtgctgtac tgggggctga agataatgca tcaaacaagt cacacagaga cagggttcct  25980
gccccaggaa atttaaagtc cagcagggaa gatgggcatt catcaaataa taataaaata  26040
atcatctcat gaaatgaatg aatgcctgca acatgcttag aactgcctgg cacaaaggac  26100
atgctcacaa gggcaattat tattataatt agacataatt gtgataagtg ctctaaaggg  26160
agctttggga gcacaaaata ggaaatagta gctaatcttg tggtgggtcc gtaaggaaaa  26220
gcttaccaga ggaactggct tccaagctaa catgttcatg ggtgagcatc aatcaaccat  26280
tgcaaagtgt gttccaggca aaggaaacag caaggacaaa ggccaaaggt agaaacgtga  26340
tatggcacca ttgagaacct ataggaagtc cagtgagcct tgggtgtaga ttgcagaagg  26400
aaataagaca aagggctcat ctgggcagga ccttgaaggt tgcaggagga gtttggattt  26460
atggtctagc actgggaagg tggaaaaggt cttgacgtgc tctgacttgt cccagttctc  26520
atcctctact ctttggctgg ttaaaagaaa aactttagac aaattaaact tagcagagtc  26580
tatctgaaca aagaaacaat tcatgaattg ggcagcacaa ggaaccagta aaggttcaga  26640
gagctccatc cagcaatgtg gtcaggcact atttatccac agggaaagga actgaggtac  26700
tgaaacagcc tgattggtta cagctctgtg tttgccttat ctgagcatgt ctgggcagct  26760
tgtagcctgt gactggctga agcttggctg ccctgattgt ccaaggttac ttgttacaag  26820
aatatactct caagtttgtt tacatgttga gttacattac aatttgttat gtagggaggc  26880
tgctttaggc caaatttaat tgaatttaac atgcaccatc catgaaaggc cccagaaaca  26940
aacccccagt cttgagtttc atcagtgact tcagtgatcc agggtttggc ccagcccccg  27000
gttttgcgca gtacagtgac ctccttccac attttatctt caatgaaaat tgggaacatg  27060
tgtggtgatg gcttgaatgt caatgtcttc tctcaatttt gctatctgaa gtttcttttt  27120
tttttttgt cttcagacgg agtcttcctg tgttgcccag gctggagtgc agtgtcacga  27180
tcacagctca ctgcaacctc tgcctcccag gttcaagtga ttctcctgcc tcagcctccc  27240
gagtacctga aactacgggc gcatgccacc atgcctggct attttttttt atttttagta  27300
gagactgggt ttcaccgtgt tagccaggat ggtgctgatc ttctgacctt gtgatatgcc  27360
cacctcagtt tctgaaagtc ctgggattac aggcataagc cactgcgact ggcctgctaa  27420
tttgttttaa gagaggcaga gatgtaggga aataaggaca gagacagata agtaacaaag  27480
ataatgagac tgagaaacag agttagggac aaagagggaa cacatagaga tagagatggg  27540
gagccagtgg cagaaagaca gagggcaaac ctcagacagt atacagagag gaagagagag  27600
agacacagag agagagagag tcacgtaagg agaaggagga ggaggaggaa taagaggaga  27660
gagagtagga aaaggaagga ggaggggaga aaggagggaa aggagagaaa cagaataaga  27720
gataggaaaa agagagagtg acataaaaag agaggaagaa agaatgaaca agacaaataa  27780
ggtatcttta gagggagatg aaaagaaaga atgagagaga aagagattgg ggagaaatca  27840
gattcaaata gatggagata ggaagttaag caagatggaa gaaagccaaa aaaaggagag  27900
gaaaagaaga aaagctgtgt ctgacaggta tagacagaga aaaagacagg agtagggctg  27960
ccaggggcag aaagaaaggt ataacccaag ccaaaagggt actgcagcca aagaaattcg  28020
aaaggtgtcc aaacagacgg ccccagagat ggggagggcg tgatgagagg gagataataa  28080
```

-continued

```
gcctcaggct gttgtgaaaa atgttaggtc acacaaagag ttacagaaga acaggcccag  28140
agacctgcct gtttctaagc tcatgtcacc caccttctgg gtatgccaaa gggatgtgga  28200
cacttttcca aacacctcca catagacaca cttgtccaac aacttgacag gcatagggaa  28260
tgcctgaaaa ctcacacttg acatggcctt tccaaggttt gcagattatg aaacactgaa  28320
gtgaagggaa aggctccctt tgtctctgcc tgagcttttt ccagcaccct ttgttcttat  28380
ttttctccca atctgtggtt tagaatctac tgggggttcc ttgcacctct gagaatcagt  28440
ggaagccata gaccctccct gtctcatacg catcagtccc attcacaatt tatatacaat  28500
tgggcttttc ccccttgag ctcttgaagc ctgtggatct caggctgaga ctagaagaca  28560
gcctagagac acagacacag acacatggcc agaaacacat accccacaca taccccagaa  28620
acaaacacaa ggcagtaacc aaaccttaag cctccttagc acaagccaag tgctattcta  28680
agaattttta caattgtctc ctttaacctc acaagagccc tttgagggag gtgccattct  28740
ccccatatga gaagtgaaga acactaagaa tgttgtcata aatgtgctca cactcacaca  28800
tgtacaggta cacacacaca cacacacaca cagaaccaga aatgggtcat tatactctgt  28860
gggtttcacc aaccctttgg aactgtaaca gaagctagaa actctcttat ataaaaatga  28920
acatggcgcc gggtgcagtg gctcatgcct gtaatcccac tttgggaggc caaggcaggt  28980
ggattatctg aggtcaggag ctcgaggcta gcctggccaa tatgatgata ccccatgtct  29040
actaaaaata gaagaaatta gccaggcgtg gtggcaggtg cctgtaatcc cagctacttg  29100
gtaggctgag gcacaagaat catttgaacc acctgggagg tggaggttgc agtgagccaa  29160
gatggtgcca ctgtgctcca gtctgggtga caaagagaga ctccatctca aaaaaaaaaa  29220
aaaaaaaaaa aaaaaaaaaa aaaagagaga gagagaaatg aacgtggcac atccactcaa  29280
agatttgcat ctggtttcag agcagcttcc taaaagtcca ccctgaattg taggttaaag  29340
gccagtctta tgcaaatctg ttgcagtgga catttgtgtc tgggcttagg gacatggcag  29400
agcgaagtgt atgcacctgc cctgtgccca cactggtgac cttctgtgtc cacagggaag  29460
cggatttgtc ttggtgaagg catcgcccgt gcggaattgt tcctcttctt caccaccatc  29520
ctccagaact tctccatggc cagccccgtg gccccagaag acatcgatct gacaccccag  29580
gagtgtggtg tgggcaaaat acccccaaca taccagatcc gcttcctgcc ccgctgaagg  29640
ggctgaggga agggggtcaa aggattccag ggtcattcag tgtccccgcc tctgtagaca  29700
atggctctga ctccccgcaa cttcctgcct ctgagagacc tgctacaagc cagcttcctt  29760
cccctccatg gcaccagttg tctgaggtca cattgcaagt gagtgcagga gtgagattat  29820
cgaaaattat aatatacaaa atcatatata tatatatgtt cttgtttttt gagacagagt  29880
ctcacactgt tgcccaggct ggagtgcagt ggcgtgatct cggctcactg caacctccac  29940
ccccggggat caagcaactc tcctgcctca gcctccctag tagctgggat tacaggcatg  30000
cactaccacg cttggctaat ttttgtattt ttagtagaga tggggtttca ctgtgtaggc  30060
caggctggtc tcgaactcct gaactcaagt gattcaccca ccttagcctc ccaaagtgct  30120
gggattacag gcgtgagtca ccgtgcccag ccatgtatat atataatttt aaaaattaag  30180
ctgaaattca cataacataa aattagctgt tttaaagtgt aaaatttagt ggcgtgtggt  30240
tcattcacaa agctgtacaa ccaccaccat ctagttccaa acattttctt tttttctgag  30300
atggagtctc actctgtcac ccaggttcga gttcagtggt gccatctctg tccactgcaa  30360
cctccacatc ctgggttcaa gtgattctcc tgcctcagcc tctggaggag ctggtatcac  30420
```

-continued

```
aggcgtcccc caccacgcct ggctaaattt tgtattttta ggtggtcttg aactcctgat  30480
gtcaggtgat tctcctagct ccaaatgttt tcattatctc tcccccaaca aaacccatac  30540
ctatcaagct gtcactcccc ataccccatt ctctttttca tctcggcccc tgtcaatctg  30600
gtttttgtca ctatggactt accaattctg aatatttccc ataaacagaa tcatacaata  30660
tttgattttt tttttttttt tgaaactaag ccttgctctg tctcccaggc tggagtgcta  30720
tggtgcaatt tttgttcact gcaacctctg ccttccaaga tcaagagatt ctccagtctc  30780
agctcccaag tagctgggat tacaggcatg tactaccatg cctggctaat tttcttgtag  30840
ttttagtagg gacatgttgg ccaggctggt ggtgagctcc tggcctcagg tgatccaccc  30900
acctcagtgt tccaaagtgc tgatattaca ggcataatat gtgatctttt gtgtctggtt  30960
gctttcatgt tgaatgctat ttttgaggtt catgcctgtt gtagaccaca gtcacacact  31020
gctgtagtct tccccagtcc tcattcccag ctgcctcttc ctactgcttc cgtctatcaa  31080
aaagcccccct tggcccaggt tccctgagct gtgggattct gcactggtgc tttggattcc  31140
ctgatatgtt ccttcaaatc tgctgagaat taaataaaca tctctaaagc ctgacctccc  31200
cacgtcaaga ggtgatctgt gccattttgt gtgtgattct tttattgtcg ggtctctagg  31260
gatttttctg gaaggaatgt tggtgagaat gcctctctca cctcaatgcc aactctgtga  31320
agggccaaac cattgtcttg ctcatccctg tactctcaac acagcgtgtg gcatatgaca  31380
ggtgttcaaa atatttggtg aggaatgaat gaatgagtgg ctaaatcagc cacccccctac  31440
ccccacagcc cacccaaaat ggagctaggc ctcctccatc agactatatc tcctccatat  31500
cccactttct tgtgaggtcc agaataaatt ctcatcccca aagggcccag gatgcccccca  31560
ttctgcctac cagttactct cgataccccg tgctgcaatg ccaccttttg ataaagctta  31620
gcgctattct tgcagtggaa ccactctaaa tccagcctcc aggctggacg cggtggctca  31680
tgcctataat cccagcactt tgggaggccg acgcgggtgg atcacttcaa gtcaggggtt  31740
cgagaccagc ctgaccaaca tacaaaaacc gtgtttcaac taaaaaagat acaacaatta  31800
cccgggcatg gtggtgtgca tctgtagtcc catctactcg ggaggctgag acagggtgat  31860
cgcttgaatg caggagggag aggttgcagt gagccaagtt cccgccactg cactccagcc  31920
tgggtgacaa agtgagactc cgtttcataa ataaataaat aaataaatcc agcctccaaa  31980
cattccacca gcaggaccac caccccttccc tgagggaggt gctgcaagtt taatatcatt  32040
atcacaagga tacatcagcc agcctgtggc cagtgggaag ctggccctgg gactccaccc  32100
tgagatgcta accttttggc gtctgcagca tctgccatct ttgggctcct tgtagcctct  32160
gaagagttaa cagagactct gccagtacaa atgcatggca cacattccct caccaaccac  32220
agaaataaca aacagagcaa catgtctttt aagagcgaca gcagaatgga aggcgggaag  32280
aatgaggacc acggtgccct cagccttctc actcctcatt gtccccagtg gcctcttgct  32340
actctggttc tggggccatc ccacctccca gggctgcctc tctcctaggc cctggcctct  32400
gcccttcctg gggagcatt ttgcaaataa accacagggc tttctgaagt ctgtccaggt  32460
ggtgagatgg gagagtgtgg aagggatgga aaaggaggag gtgggtagac gggaaacagc  32520
tcacaggcag caaggcagtt ggggtcgtac tttgggtggg attccacaga caagcttggg  32580
aattcctttc tggcttatat attaactaca gaagcttctg gaattttata aggtgaaatg  32640
gagaggagac agactggagg gtgaaattct gatagacttg aggctttgag atgtggtcct  32700
ggggtggagc aagacaagaa aagtactgga gattggggtt tgaggagtct atgcaattat  32760
ttttattttt aaaaatcttt gtggctacat agcaggtgta tatatttatg tggtaagtga  32820
```

-continued

```
gatatttcga tacagacata caatgtataa tcacaggcat acaatgtaga caggcataaa  32880
gtgtatagtc acatataata ataacatcat ggtaaatggg gtaaccatca cctcaagcac  32940
tcatcatttc tttgtgttac attagagtta tattccctct gttatgctaa aatgtaccac  33000
aggctgggca cagtggttca tgcctataat cccagtattt tgggaggctg aggcagacag  33060
attgcctgag ctgaggagtt cgaaaccacc ctgggcaaca tggtgaaacc ctgtctctac  33120
aaaaatacaa aaaaaaatta gccaggcatg gtggcatgca tctgtaatcc cagctactct  33180
ggaggctgaa gcgggagaat tgcttgagcc tggtaggtgg agtttgcagt aagccaagat  33240
tgtgccactg cagtcccgct tgggtgacag agtgagactc catctcaaaa aaataaacaa  33300
gcaaacaaac aaaagtacaa tgaattattg ctgacggcca tcaccttatt gtgctatcaa  33360
aaactagatc ttattcattg tatcgaactc tatttttgta cccattagcc atccccagtc  33420
cctcacctcc acccttccca gtctctggta accatcattc tactctatct ccatgagtta  33480
aattgtcata atttttagct cccacgaatg agtgagaatg tgcaaagttt gcctttccgt  33540
gcctggctta tttcacctaa cataatgtcc tgcagttcca tccatgttgc tgcaaatagc  33600
aggatatcat tctttttttaa tggttgaata gtactccctt ctgtatgggc accatatgaa  33660
cacttaggtt gattccataa cttggctctt gcaaacagag ctgcaaaata cactggagtg  33720
cagatatctc ttcagtatac ggatttcctt ttttttgata tagatttagc ggtgggattg  33780
ctggattgtg tggtagctct atttttagtg gttttctttc tttttgtttg tttattttat  33840
ttctttattc attttttttg agatggagtc ttactctgtc acccaggctg gagtgcagtg  33900
gtatgatctc agctcactgc agcctccacc tcctgggttc aagcgattct cctgcctcag  33960
catcctgagt agctgggact acaggcacct gccgacacgc ttggatgatt tttgtaattt  34020
tagtagagat ggagtttcac cacgttggcc aggctggtct tgaactcctg acctcagatg  34080
actcgcccac ctcagcctcc caaagtgctg ggattacagg catgagccac cgcacctggc  34140
ctattctact tttttttttc tttttcttag ggaaactcca tgttgttcct caaagtggct  34200
ctattaattt acattaccac caacagtgta caagggttcc atggggatta cttcagattg  34260
agtggtcaga gagggctcct ttgagaagac ttctgagaat tggccatggg aaggtgtggg  34320
gagaagcctt ctcagctgag ggaacagcaa ggtcaaagac ccagaggtaa gaaagcaagc  34380
ttggaacctt ccaggagcaa caaggcattg gctctgataa tgccttctcc tgctaaaatg  34440
acagctctag gaaggcaggg ttcttatttc ctgtctatct atctatctat ctatctatct  34500
atctatctat ctatctatca tctatctatc tatcatatat ctatctatcc gtctgtcttt  34560
atttatttat agaggcagag tcttgctcta ttgtccattg tattagtcca ttttcatgct  34620
gctgataaag acataccgta gactgggtaa tttataaaga aaaaaagttt aataaactca  34680
cagttccaca tggctgcgga ggcctcacaa tcatgctgaa aggcaaaagt tgcgtcttac  34740
atggtggctg gcaagagaga gaatgagaac caagagaacg gggtttcccc ttataaaacc  34800
aacagatctc atgagactta ttcactacta tgagaacagt atgggggaaa ccacccctat  34860
gattcaatga tcacccaccg ggtccctccc acaacacgtg gggattatgg gagctgcaat  34920
tctagatgag atttgggtgg ggacacagcc aaaccatatc accaaggctg gagtgcagtg  34980
gtatgatcat ggctcattgc agcctccaac ttctgggttc aagcaatcct cccacctcag  35040
cctcctgatt agtggtgact acaggtgtgt gacaccacct ctggctggct tttaaatttt  35100
ttggagagat ggagtcttgc tattttgccc aggctggtct caaactcttg gtctcaaatg  35160
```

-continued

```
atcttcccat cttgacttcc caaagcactg agattacagg tgtgagccat tgcacctggc  35220
tggttctcat ttatttaagt attactgctg tcatggtttg ctttggtccc tgtgggttcc  35280
cccacccttt gaaacaagtg cctgacacat ggtagggttc acaataaata tttgtagaat  35340
aaataagagc tgagccttca aggggtccaa aatacttgca cggagttttt ctaggtgggc  35400
acgatgccac ccagctgcag gactatttca gggtgttcat tggctcctct ggttgatctt  35460
ttgatgcctg tataagaact cccacttctc caaatctggg ggccacatct ttagagttct  35520
cagctttctg tctctcagga atgaaggaga taatatcact gattggagcc agattgtctg  35580
gatgttgaat cccagctcct tgctggtgcc tttgagaagt gactttagcc ctccatgtgc  35640
cttatttctg cctctgtaaa cggagatcat catagcacct ctcatgtggg gctgtttgac  35700
gattcggtga ggtatgtgca aagagctttt tgcacttgca aaaagtgtct gggatatcat  35760
tgtgtgctgt aagaatgagc tgtaatgatt atcactgaga cttgttgttg ggattaaaag  35820
agatcaggtc tgtcagggcc tggtacacaa gaggtactag aaaaataatg ggaggtttag  35880
gtgctccttc ctccagatac actcgtaaat atgactgctg tgtcgtcatc tactttttag  35940
ggatatgaag aatctgctgt gtgaccttag atgaataaat ctctgattca ctctgggcct  36000
tggttttccc tgcctctgaa aggggtatga tgtttccttc ccttttgcct gggcgcaggt  36060
actgggtgct ttgtagttaa gggagtatca gctggtggct caagggtaga ttctaacagg  36120
aacttccaag ctggagaaat actaggctac acctcagaga ggggaggtgg gtaagggagg  36180
cccctgctgg tgtgagcagg aggtgggtga gggaggcccc tgctggtgtg agctcgatcc  36240
tttatccctg agcttcagac tctcttaagc cttcccacat gagaaactga catccagatg  36300
gaggtgggga ccctgcaatg taaagccagg tcacctgtcc acagaggtgt gtctgataac  36360
cagggcatga taggttagag agtgtggtgg ctaaaagcac cagcccttgg atcacctgag  36420
gtcaggagtt caagacctgc ctggccaaca tggtgaaact ccatctctac taaacataca  36480
aaaattagct tggtgtggtg gtgggcacct gtaatcccag ctacttggga ggccgaagca  36540
ggagaatcac ttgaacccag gaggcagagg ttgcagtgag ctgagattgc gccatttcac  36600
tccagcctgg gtgacaaaag cgaaactctg tctcaaaaaa agcaccagcc ttagactcag  36660
agagaccagg atttgagctt gggggacctc agcttcctct ctgtgtgacc tcaggtaagc  36720
cacttatact ctttgggcct cagtttcctc atttgtaaaa ttgaggccgt gattgaacct  36780
ccttcaagag ctgttgtgag tgctataggg gatactatct taaagcactt aatgcagtgc  36840
ctggcacatg gtagttctgt agaagtgctt gctattttaa ttcacgtgca caggtcctgc  36900
ctgtgggtga gggctcagta gatggaacag cgatggttga tatagttggg attgtgagga  36960
ttattatgac aggggctaat ttgaatgggc ctgtgttgtc tgccctcccc actgccagcc  37020
tgatttccct ctgcctggct ttgcagctcc tcccattggc tgctggggtg taccccttgc  37080
atgcggatga gaaacgagtc aatgaagtcc cgtggggaat tgggatccag cgtgcactgg  37140
ttgtgctcca ctttcttggc aatgaagtcc tccagccctt gcagctcctt aaaggcctgt  37200
tgctgtggtc ctggcaggtg tttcatcacc gaagagaaca tctcatagag ctggggttgc  37260
agagagagga tgggaaggga aggaccgctg tcaggaggca ggaactgatg ggaatgggac  37320
ctgtgtcaga gcaagaaagg cactgggtta aaggcaccta cctgcccagg tgtttaggta  37380
tttcagtggg gctggatggg aacatatatg taagtcttca tgagggttaa gtgagaaggc  37440
tactgtccag aaatttaggt aacatggact gaggcacaca tccaggtttc aatgaaggtg  37500
gattggagcg cacagctagg tgttcagaca ttcaaggcag gatgtgttgg aaaacacctg  37560
```

```
ttcaactgtt tagctactca gacggggctg gtatgagggg agtgtcacct gtctaggtat  37620
gtaggcattc aggtgggcct ggttgaagac aactaccgag atacttattg ggtctggatt  37680
gggggctttt gttcagatgt tcaggtatta aagtggggct ggtgaagatg ttgaagagga  37740
ggggatacct gttgaggtgt ttacctatcc aagtgggatg cactgggggc acctctgtaa  37800
ggtgtgtgat tggaaagggt tggggaacac ttatttgggt gtctggggaa taatctgtct  37860
agatatttat gtgtttaggg tattggttag ggcacctgtc catgttttca ggtatttaag  37920
tgggtgaagt agagggcgct tggccagata ttccagtggg ctaatctggg acatttgtgt  37980
agatgtgaaa tgattatgat gggctggatt ttgcagcacc aggtgttcag gtatgcagga  38040
ggcgggttga ggcagtcact tgtccaggtg ttaaaatatt cagaagaact gggtagggag  38100
catctgttag aaattatggt aagttgggga tgggaacatg tgcccaggtg agagagctga  38160
gctgagggta tgcatcctgc cttcaggctc tgttttgggg atcatctgtt gagctatcca  38220
ggtgtccttg gagactgggt attgggcacc catcctgggt tctggtgcaa ctttccggtt  38280
gtccaatatt gggggctgat tttgagggga cactgtctgg aggggggtgg gagtttgggg  38340
cacctgtccc catgtagggg agcagttggc aggttgtggt aggggcgtga cagccaggct  38400
gcagccggtt acctgccccg tggagggtgc cgtgaactgg aagctttcca gcatcatgca  38460
cagcagtgac aggaactttt gtcctcatag tcaaagcggt ccccaaagac aatggagctg  38520
atgacattgg aggtggtacg gcttaggaag aaggtgggat agatgctgga gcttgcgggt  38580
gtggcggtgt attgggggag aagggggttg ggaagagagt caactcagag ctctgatgct  38640
agtctgagaa ttccaggagg cactgccctg atgagccaca ttcccagcgc cagactacag  38700
ggctgggagc gcgggcgcct ttccccacca aggcccggtc cccagacaga acgcgcgcgg  38760
gttcctcgcc ctgggcgttt tccttctccc gcctccacac tcggggtgtt ctgctcaccg  38820
cgcgtgccct agacggcctt gatgaggaag cccgccttct cctggatacc tccttgatgc  38880
cgcgcttgcc caccccgaag tcccgcaggg tggcgatgga gaagcgcctg agcggcttgg  38940
tgcgctccca ggtgcggcag gtcactcctg ggagaggaac gcaggggtgg ggagaggtca  39000
ggccgtggga acaggcacag aagcctcgcg caggagaact gcaaactcag tcagagaaac  39060
acagagagaa acagagaccg aacaggaaca agaggatcag aaaagagaca ggccagacag  39120
acagatgcac agcagaacag agggagacgg gacactccat ggagcatagg gagggaagga  39180
gggagagaaa aagacagaga tgggagaaga tgatggaagg gggggaagtg aggtatgggg  39240
agatctgcga ggagaaaata aaaatggtga aagagtcttt tttgtttgta tgtttgttta  39300
tttgtttttg agacggattc tcgctctgtc gcccaggctg aagtgcattg tcgccatctt  39360
ggccgctcgc tgcaacctcc accttccagg ttcaagcgta aaaatggtga aagactccta  39420
agctgagctg gtgaagacag aaaactacgg aaagagaaac agagacggtc gggaaggagg  39480
agagactgtt atcaggagag gaggctggag atgtggaagt aggaataccg cgaaatccta  39540
agacagagga agaagaagga gaggtcagtg gacagaggag aaactcagag aagcacagaa  39600
gctgagaagg acaaaaagac aaatgaagac agagaaccag ggttggaaaa cagaaaccca  39660
ggattgtcct cagagatggg gaaagaggag actccagtga gagaggcagg gagaaatctg  39720
gacagggaca gggacaggga tgctggagac aggcaagagg gagaggccgc aatgaaggga  39780
gctggggagc gaaggccaga caggggctc tgccgcagcc ttcagtgggc aggagagtca  39840
gggagaaggc tggggacacg gaggccatcg agtcggcctg gccaccttcc ccctcttggg  39900
```

-continued

```
caccccctca ccatagcctt tgaagagcca gtcgaaggtg gcctgctcgc ctcgcccgct  39960
gaactcctca gcctggtcca ccagagcctc cttgacggca tcatgtccgc acagcaccac  40020
gacccgccgg ggccccaggt gaatggtgaa cacggggcca tagcgctcac tgatctgatg  40080
gaggcaggtg ggagtggtta gagggagcag cccccactct gaatgggcgc agcaccgaga  40140
tatcatgtac tgggatgttt tgcccccagg ttctcacagt cagggagctg gacatcccaa  40200
gatcctgtct ttccagccta ggaccctgat gctgaaactc caaaactccc tttcctaaga  40260
ctctggtcca cactggtcaa tcccctgcca caaagcctca gccaactggg cagcccccac  40320
cccgtgccac ccatctccct gccttgggac accttcatga tggagtcaca tatgtgctct  40380
gtgttcagct gcaggtagtt tccaataaag agcaatgggg tgggtcccaa aggcagcttc  40440
cccctgctct tcctctgctg ccagactgac atcaagacca tcacagtcag gctggccagc  40500
aaggccacca gaagcagccc tgaggccagc atggtggcag tggaatgata gatggtgacg  40560
gctggggtgg tttgccttta tactgcctga aaaaaagggg tggactttgg ctggttataa  40620
aatcacctca tttcacctcc caactacatc ctctccgtga accccaccta gctttggaca  40680
caaccagcaa aggaggagga gggggacccc agggaagctg aacagagagg gtacctcccg  40740
actaaatctg tggtacctca ggaggggtgc cccagggctg tggatttagg agcgggcaac  40800
agataagctg tagaacaaag gagttgggaa tatttgcata ggggagcact tgggctttgg  40860
atttgggatc tgggagtgag aatgcacccc aaaattgtgg atttggggt tccgaggaga  40920
agaatgcaaa ggtctgggtt ttattagggt gagatggaag tgtggctgtg catctggggg  40980
tcttctgttg tggaggatgc agggttaagg gtctcaggag gggggattcc aggcatatgg  41040
acttgagagt cttggggcta ggaagaccca gggctgtggg tgtggagttt ctgggaggag  41100
gagtgtgtag caagcccagt aggtcgtccc agaaagccca gcagcccagc actgggccca  41160
ggggctgact tgattttgct tttgcccaga gctgtctctt gatgcccgga atcctcactg  41220
gaacctcaga gtgaggccag gatgggtgcc atggaaactc cactgaccat ctctggttgg  41280
caaaggggtg gaagaccaga gccatatttc aagggaaatt tccacacacc tggagaagag  41340
taccttgtgt tatcagttgg cagagggatt ggccaggtct ggagaaatag taacaacaac  41400
ccccaaatgg tggaaaaagc tcaagtgtcc caagggttgt aatttacaaa gacctccact  41460
ggtttccaac ccagatcctt agggaaaccc actagattga ttgtatcatc cctattaata  41520
ttatgattgt tgtttatctt tctcatttta tataagggtc tacagaggac agaaaacaga  41580
cagtaggcag gggacatgca tgagtggccc tgaactccca tctctcctgc tctgagtact  41640
tagttcccct ttctggattt ggttttccca ccagtagaaa gggagtattt aggaaaagat  41700
catatttgag ggtgagttaa gtctccttta agggcgattc ctgctttgtc aggggctact  41760
actattagca ggcagaggga acaatcgcag aagagattgg ggtaaactcc agtgttaggc  41820
acagaggtag atcctggggt gggtgtgagt ggagaaggga tgagtagccc tcctgtcctt  41880
ccctcaggga aattcttcct tagtaaacgg ggcagttacc ctttggtgag catggtcgta  41940
tatgggaaga ttaagtctag gtgtgtatga tctggtcgaa tctttgtaac agtgaggttt  42000
gttcatcatg atcatcctca ttttgaagat gagcagatct agactccata aatcctcttg  42060
agtgaggtca cacagggaat aagtgaggga gctgggatgt gaactttctt ctcatccccc  42120
gtcattgact ggcctagatc accctgggag tcaagtgcag gccaggctta gcaggaggtg  42180
agtgctgaga ctggcatcag cagtggacac actgatgaca ttggcgggtt ctgatatcag  42240
catcaggtgt gttcagggag ggaaaggcat cgtgttggct ttgggactgc ccccaggtgt  42300
```

atgcgaggat gggaaacaag ttggtactga acttgatacc aggagaatat tgaagtcatg 42360
tttggtgcca agagggctct gtgtgttgtt tcaggtttca ttgagggcat aagtgtgtcc 42420
tgcttcagga gggcgtaaga atggcaccat atagggtctg aggttggtcc cagtgggctg 42480
tgacatgagc atgaggcagg tgctgatatt ggtcctatgt gggtctgaga tgagcctcag 42540
ccagatc 42547

<210> SEQ ID NO 13
<211> LENGTH: 1690
<212> TYPE: DNA
<213> ORGANISM: Mouse

<400> SEQUENCE: 13
gaagcattga ggaggatcac acacacagtt gtagggagaa cacagagaag taaattgctg 60
acaaacaagc agggatggac ctggtttcag ctctctcact ggaaacctgg gtgctcctag 120
caatcagctt ggtgctcctc taccgatatg ggactcgtaa acatgaactt tttaagaaac 180
agggaattcc tgggcccaaa cctctgccat ttttaggcac tgtgctgaat tattacaagg 240
gtttatggaa attcgacatg gagtgctata aaaagtatgg aaaaacatgg gggttgtttg 300
atggtcaaac gcctctcctt gctgtcacag acccagagac gattaagaat gtgctagtga 360
aggaatgttt ttctgtcttc acaaaccggc gggattttgg cccagtgggg ataatgagta 420
aagctatctc aatatctaag gatgatgaat ggaagagata tagagctttg ctgtccccca 480
cattcaccag tggaaaactc aaggagatgt tccctgtcat tgaacagtat ggagacattt 540
tggtaaagta cttgaggcag aaggcaaaga aaggcaagcc tgttactatg aaagatgtgt 600
taggtgctta cagcatggat gtgatcacca gcacatcatt tggagtgaac gtggattccc 660
tcaacaaccc agaggatcct tttgtggaga aagccaaaaa gcttttaaga tttgattttt 720
ttgatccttt gctcttctca gtagtacttt ttccattcct gacaccagta tatgagatgt 780
taaatatctg catgttccca aaggattcaa tagaattttt caaaaaattt gtggacagaa 840
tgaaggaaag ccgcctggat tctaagcaga agcaccgagt ggattttctt cagctgatga 900
tgaattctca taataattcc aaagacaaag tctctcataa agccctttct gacatggaga 960
tcacagccca gtcaattatc tttatttttg ctgggtatga aaccaccagt agcacacttt 1020
ccttcaccct gcattccttg gccactcacc ctgatatcca gaaaaaactg caggatgaga 1080
tcgatgaggc tctgcccaac aaggcacctc ccacgtatga tactgtgatg gagatggaat 1140
acctggatat ggtgcttaat gaaaccctca gattatatcc cattgctaat agacttgaga 1200
gagtctgtaa gaaagatgtt gaactcaatg gtgtgtatat ccccaaaggg tcaacagtga 1260
tgattccatc ttatgctctt caccatgacc cacagcactg gtcagagcct gaagaattcc 1320
aacctgaaag gttcagcaag gagaacaagg gcagcattga tccttatgta tatctgccct 1380
ttgggaatgg acccaggaac tgccttggca tgaggtttgc tctcatgaat atgaaacttg 1440
ctctcactaa aattatgcag aacttctcct tccagccttg taaggaaaca cagatacctc 1500
tgaaattaag cagacaagga cttcttcaac cagaaaaacc cattgttcta aaggttgtgc 1560
cacgggatgc agtcataact ggagcatgag tctccctcaa ggagttcttc tgagttcttc 1620
agaaaggcag tgtctaagaa catcggacat tttagtttca tcatgagtaa aattgagatg 1680
aataaggggc 1690

<210> SEQ ID NO 14

-continued

<211> LENGTH: 2768
<212> TYPE: DNA
<213> ORGANISM: Human

<400> SEQUENCE: 14
cactgctgtg cagggcagga aagctccatg cacatagccc agcaaagagc aacacagagc 60
tgaaaggaag actcagagga gagagataag taaggaaagt agtgatggct ctcatcccag 120
acttggccat ggaaacctgg cttctcctgg ctgtcagcct ggtgctcctc tatctatatg 180
gaacccattc acatggactt tttaagaagc ttggaattcc agggcccaca cctctgcctt 240
ttttgggaaa tattttgtcc taccataagg gcttttgtat gtttgacatg gaatgtcata 300
aaaagtatgg aaaagtgtgg ggcttttatg atggtcaaca gcctgtgctg gctatcacag 360
atcctgacat gatcaaaaca gtgctagtga aagaatgtta ttctgtcttc acaaaccgga 420
ggccttttgg tccagtggga tttatgaaaa gtgccatctc tatagctgag gatgaagaat 480
ggaagagatt acgatcattg ctgtctccaa ccttcaccag tggaaaactc aaggagatgg 540
tccctatcat tgcccagtat ggagatgtgt tggtgagaaa tctgaggcgg gaagcagaga 600
caggcaagcc tgtcaccttg aaagacgtct ttggggccta cagcatggat gtgatcacta 660
gcacatcatt tggagtgaac atcgactctc tcaacaatcc acaagacccc tttgtggaaa 720
acaccaagaa gcttttaaga tttgattttt tggatccatt ctttctctca ataacagtct 780
ttccattcct catcccaatt cttgaagtat taaatatctg tgtgtttcca agagaagtta 840
caaatttttt aagaaaatct gtaaaaagga tgaaagaaag tcgcctcgaa gatacacaaa 900
agcaccgagt ggatttcctt cagctgatga ttgactctca gaattcaaaa gaaactgagt 960
cccacaaagc tctgtccgat ctggagctcg tggcccaatc aattatcttt atttttgctg 1020
gctatgaaac cacgagcagt gttctctcct tcattatgta tgaactggcc actcaccctg 1080
atgtccagca gaaactgcag gaggaaattg atgcagtttt acccaataag gcaccaccca 1140
cctatgatac tgtgctacag atggagtatc ttgacatggt ggtgaatgaa acgctcagat 1200
tattcccaat tgctatgaga cttgagaggg tctgcaaaaa agatgttgag atcaatggga 1260
tgttcattcc caaaggggtg gtggtgatga ttccaagcta tgctcttcac cgtgacccaa 1320
agtactggac agagcctgag aagttcctcc ctgaaagatt cagcaagaag aacaaggaca 1380
acatagatcc ttacatatac acaccctttg gaagtggacc cagaaactgc attggcatga 1440
ggtttgctct catgaacatg aaacttgctc taatcagagt ccttcagaac ttctccttca 1500
aaccttgtaa agaaacacag atcccccctga aattaagctt aggaggactt cttcaaccag 1560
aaaaacccgt tgttctaaag gttgagtcaa gggatggcac cgtaagtgga gcctgaattt 1620
tcctaaggac ttctgctttg ctcttcaaga aatctgtgcc tgagaacacc agagacctca 1680
aattactttg tgaatagaac tctgaaatga agatgggctt catccaatgg actgcataaa 1740
taaccgggga ttctgtacat gcattgagct ctctcattgt ctgtgtagag tgttatactt 1800
gggaatataa aggaggtgac caaatcagtg tgaggaggta gatttggctc ctctgcttct 1860
cacgggacta tttccaccac ccccagttag caccattaac tcctcctgag ctctgataag 1920
agaatcaaca tttctcaata atttcctcca caaattatta atgaaaataa gaattatttt 1980
gatggctcta acaatgacat ttatatcaca tgttttctct ggagtattct ataagtttta 2040
tgttaaatca ataaagacca ctttacaaaa gtattatcag atgctttcct gcacattaag 2100
gagaaatcta tagaactgaa tgagaaccaa caagtaaata tttttggtca ttgtaatcac 2160
tgttggcgtg ggcctttgt cagaactaga atttgattat taacataggt gaaagttaat 2220

-continued

```
ccactgtgac tttgcccatt gtttagaaag aatattcata gtttaattat gccttttttg   2280

atcaggcaca gtggctcacg cctgtaatcc tagcagtttg ggaggctgag ccgggtggat   2340

cgcctgaggt caggagttca agacaagcct ggcctacatg gttgaaaccc catctctact   2400

aaaaatacac aaattagcta ggcatggtgg actcgcctgt aatctcacta cacaggaggc   2460

tgaggcagga gaatcacttg aacctgggag gcggatgttg aagtgagctg agattgcacc   2520

actgcactcc agtctgggtg agagtgagac tcagtcttaa aaaaatatgc ctttttgaag   2580

cacgtacatt ttgtaacaaa gaactgaagc tcttattata ttattagttt tgatttaatg   2640

ttttcagccc atctcctttc atatttctgg gagacagaaa acatgtttcc ctacacctct   2700

tgcattccat cctcaacacc caactgtctc gatgcaatga acacttaata aaaaacagtc   2760

gattggtc                                                             2768
```

<210> SEQ ID NO 15
<211> LENGTH: 39
<212> TYPE: DNA
<213> ORGANISM: Artificial Sequence
<220> FEATURE:
<223> OTHER INFORMATION: Primer

<400> SEQUENCE: 15

```
ccggaattca ggaaagacat gatactgtcg gcagaagcc                            39
```

<210> SEQ ID NO 16
<211> LENGTH: 41
<212> TYPE: DNA
<213> ORGANISM: Artificial Sequence
<220> FEATURE:
<223> OTHER INFORMATION: Primer

<400> SEQUENCE: 16

```
cgcggatccg gccgctgcag gcgcagaact ggtaggtatg g                          41
```

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17

```
gatgtgctcc aggctaaagt t                                                21
```

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18

```
agaaacggaa tgttgtggag t                                                21
```

<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19

-continued ccgcctctag agcggtttct taccaata 28

<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20
ccgccggatc cagccagagt aggcaaatct 30

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
ggatgaatat gccctacatg 20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
tgatgggcag caggtctcat 20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
acagaaacta tgtgagcctg 20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
atgggacggt tcacatgttc 20

<210> SEQ ID NO 25
<211> LENGTH: 1450
<212> TYPE: DNA
<213> ORGANISM: Human

<400> SEQUENCE: 25
gtgagcttgc tccttaagtt acaggaactc tccttataat agacacttca ttttcctagt 60
ccatccctca tgaaaaatga ctgaccactg ctgggcagca ggagggatga taatcctaac 120
tccaatcact ggcaactcct gagatcagag gaaaaccagc aacagcgtgg gagtttgggg 180
agaggcattc cataccagat tctgtggcct gcaggtgaca tgctgcctaa gagaagcagg 240
agtctgtgac agccacccca acacgtgacg tcatggccag tagggaagat gagctgagga 300

-continued

```
actgtgtggt atgtggggac caagccacag gctaccactt taatgcgctg acttgtgagg    360

gctgcaaggg tttcttcagg agaacagtca gcaaaagcat tggtcccacc tgcccctttg    420

ctggaagctg tgaagtcagc aagactcaga ggcgccactg cccagcctgc aggttgcaga    480

agtgcttaga tgctggcatg aggaaagaca tgatactgtc ggcagaagcc ctggcattgc    540

ggcgagcaaa gcaggcccag cggcgggcac agcaaacacc tgtgcaactg agtaaggagc    600

aagaagagct gatccggaca ctcctggggg cccacacccg ccacatgggc accatgtttg    660

aacagtttgt gcagtttagg cctccagctc atctgttcat ccatcaccag cccttgccca    720

ccctggcccc tgtgctgcct ctggtcacac acttcgcaga catcaacact ttcatggtac    780

tgcaagtcat caagtttact aaggacctgc ccgtcttccg ttccctgccc attgaagacc    840

agatctccct tctcaaggga gcagctgtgg aaatctgtca catcgtactc aataccactt    900

tctgtctcca aacacaaaac ttcctctgcg ggcctcttcg ctacacaatt gaagatggag    960

cccgtgtggg gttccaggta gagtttttgg agttgctctt tcacttccat ggaacactac   1020

gaaaactgca gctccaagag cctgagtatg tgctcttggc tgccatggcc ctcttctctc   1080

ctgaccgacc tggagttacc cagagagatg agattgatca gctgcaagag gagatggcac   1140

tgactctgca aagctacatc aagggccagc agcgaaggcc ccgggatcgg tttctgtatg   1200

cgaagttgct aggcctgctg gctgagctcc ggagcattaa tgaggcctac gggtaccaaa   1260

tccagcacat ccagggcctg tctgccatga tgccgctgct ccaggagatc tgcagctgag   1320

gccatgctca cttccttccc cagctcacct ggaacaccct ggatacactg gagtgggaaa   1380

atgctgggac caaagattgg gccgggttca aagggagccc agtggttgca atgaaagact   1440

aaagcaaaac                                                          1450
```

<210> SEQ ID NO 26
<211> LENGTH: 1350
<212> TYPE: DNA
<213> ORGANISM: Mouse

<400> SEQUENCE: 26

```
cttgttttcc aggcactgag gaccgcagtc cctaattcct ggcagttcct gagatctcaa     60

ggaaagcagg gtcagcgagg aggcctgggg agaggaggca tcctacaccc aatcttgtgg    120

cctgctgcct aagggaaaca ggagaccatg acagctatgc taacactaga aaccatggcc    180

agtgaagaag aatatgggcc gaggaactgt gtggtgtgtg gagaccgggc cacaggctat    240

catttccacg ccctgacttg tgagggctgc aagggcttct tcagacgaac agtcagcaaa    300

accattggtc ccatctgtcc gtttgctgga aggtgtgagg tcagcaaggc ccagagacgc    360

cactgtccag cctgcaggtt gcagaagtgt ctaaatgttg gcatgaggaa agacatgata    420

ctgtcagcag aagccctggc attgcggcga gccagacagg cacagcggcg ggcagagaaa    480

gcatctttgc aactgaatca gcagcagaaa gaactggtcc agatcctcct gggggcccac    540

actcgccatg tgggcccatt gtttgaccag tttgtgcagt tcaagcctcc agcctatctg    600

ttcatgcatc accggccttt ccagcctcgg ggccccgtgt tgcctctgct cacacacttt    660

gcagatatca acacgtttat ggtgcaacag atcatcaagt tcaccaagga tctgccgctc    720

ttccggtccc taaccatgga ggaccagatc tcccttctca agggagcggc tgtggaaata    780

ttgcatatct cactcaacac tacgttctgt cttcaaacag agaatttctt ctgtgggcct    840

ctttgctaca agatggagga cgcagtccat gcagggttcc agtacgagtt tttggagtcg    900
```

-continued

```
atcctccact tccataaaaa cctgaaagga ctgcatctcc aggagcctga gtatgtgctc    960

atggctgcca cggccctctt ctcccctgac agacccggag ttacccaaag agaagagata   1020

gatcagctac aagaggagat ggcgctgatt ctgaacaacc acattatgga acaacagtct   1080

cggctccaaa gtcggtttct gtatgcaaag ctgatgggcc tgctggctga cctccggagt   1140

ataaacaatg catactccta tgaacttcag cgcttggagg aactgtctgc tatgacgccg   1200

ctgctcgggg agatttgcag ttgaggccca ggcttgcatc ctttccccag acccccaggg   1260

atacactggc ctggaaaggg tacagcgctg gaccccacac gggaaccagc aggaaggagc   1320

ttgggagtgg caatgaaatg ctgaacagtc                                    1350


<210> SEQ ID NO 27
<211> LENGTH: 286
<212> TYPE: PRT
<213> ORGANISM: Mouse

<400> SEQUENCE: 27

Met Thr Ala Met Leu Thr Leu Glu Thr Met Ala Ser Glu Glu Glu Tyr
1               5                   10                  15

Gly Pro Arg Asn Cys Val Val Cys Gly Asp Arg Ala Thr Gly Tyr His
            20                  25                  30

Phe His Ala Leu Thr Cys Glu Gly Cys Lys Gly Phe Phe Arg Arg Thr
        35                  40                  45

Val Ser Lys Thr Ile Gly Pro Ile Cys Pro Phe Ala Gly Arg Cys Glu
    50                  55                  60

Val Ser Lys Ala Gln Arg Arg His Cys Pro Ala Cys Arg Leu Gln Lys
65                  70                  75                  80

Cys Leu Asn Val Gly Met Arg Lys Asp Met Ile Leu Ser Ala Glu Ala
                85                  90                  95

Leu Ala Leu Arg Arg Ala Arg Gln Ala Gln Arg Arg Ala Glu Lys Ala
            100                 105                 110

Ser Leu Gln Leu Asn Gln Gln Gln Lys Glu Leu Val Gln Ile Leu Leu
        115                 120                 125

Gly Ala His Thr Arg His Val Gly Pro Leu Phe Asp Gln Phe Val Gln
    130                 135                 140

Phe Lys Pro Pro Ala Tyr Leu Phe Met His His Arg Pro Phe Gln Pro
145                 150                 155                 160

Arg Gly Pro Val Leu Pro Leu Leu Thr His Phe Ala Asp Ile Asn Thr
                165                 170                 175

Phe Met Val Gln Gln Ile Ile Lys Phe Thr Lys Asp Leu Pro Leu Phe
            180                 185                 190

Arg Ser Leu Thr Met Glu Asp Gln Ile Ser Leu Leu Lys Gly Ala Ala
        195                 200                 205

Val Glu Ile Leu His Ile Ser Leu Asn Thr Thr Phe Cys Leu Gln Thr
    210                 215                 220

Glu Asn Phe Phe Cys Gly Pro Leu Cys Tyr Lys Met Glu Asp Ala Val
225                 230                 235                 240

His Ala Gly Phe Gln Tyr Glu Phe Leu Glu Ser Ile Leu His Phe His
                245                 250                 255

Lys Asn Leu Lys Gly Leu His Leu Gln Glu Pro Glu Tyr Val Leu Met
            260                 265                 270

Ala Ala Thr Ala Leu Phe Ser Pro Gly Phe Cys Met Gln Ser
        275                 280                 285
```

SCREENING SYSTEMS AND METHODS FOR IDENTIFYING MODULATORS OF XENOBIOTIC METABOLISM

CROSS-REFERENCE TO RELATED APPLICATIONS

This application is a continuation-in-part of International Application PCT/US01/29672, filed Sep. 21, 2001 and published in English, and a continuation-in-part of U.S. utility application Ser. No. 10/219,590, filed Aug. 15, 2002, both of which claim priority to U.S. utility application Ser. No. 09/666,250, filed Sep. 21, 2000.

STATEMENT AS TO FEDERALLY SPONSORED RESEARCH

This invention was made with government support under NIH grant NIDDK RO1 DK46546. The government therefore has certain rights in the invention.

BACKGROUND OF THE INVENTION

In general, the present invention is directed to compositions, including transgenic animals, and methods for identifying modulators of metabolism of any of a wide range of foreign compounds, collectively termed xenobiotics.

A number of cytochrome P450 (CYP) enzymes able to metabolize diverse substrates serve as a primary defense against potentially deleterious effects of xenobiotic compounds. Induction of the expression of individual CYP genes in response to particular xenobiotics is a central component of this metabolic mechanism. One of the best characterized of these responses is the induction of specific CYP genes by a diverse group of agents known as "phenobarbital-like" inducers. Exposure of animals to any of a chemically diverse series of compounds exemplified by phenobarbital (PB) results in a potent activation of expression of a specific subset of CYP enzymes and other proteins associated with xenobiotic metabolism. In the mouse, these PB-like inducers increase expression of CYP2B10 and several other genes. The pesticide contaminant 1,4-bis[2-(3,5-dichloropyridyloxy)]benzene, referred to as TCPOBOP, is generally considered to be the most potent of this group of inducers.

Xenobiotics, such as therapeutic drugs, insecticides, polycyclic hydrocarbons, and some natural products, are often metabolized via oxidation reactions catalyzed by CYP enzymes. These reactions add hydrophilic groups to xenobiotics, allowing the body to rid itself of these noxious or simply insoluble materials. For example, oxidation of polycyclic aromatics produces epoxides, which are very reactive electrophilic groups. Usually these epoxides are rapidly hydrolyzed into hydroxyl groups which are then coupled to other groups, producing compounds water-soluble enough to be excreted. Unfortunately, the intermediate epoxides may also be released into the cell as highly reactive electrophiles, possibly reacting with negatively charged groups in DNA and causing changes in the DNA sequence. Reactive oxygen species generated during metabolism of cocaine by CYP enzymes in humans has been associated with mutagenesis and chromosome breakage.

CYP-mediated metabolism may also result in other undesired effects, such as the rapid degradation of a therapeutically active compound, lowering its half-life in vivo. Alternatively, CYP enzymes may convert a prodrug into an active drug at a faster than desired rate resulting in a toxic concentration of the active drug in vivo. Additionally, the activation of CYP enzymes by the administration of a therapeutically active compound or exposure to another foreign compound may result in faster metabolism of a second therapeutically active compound, reducing its effectiveness or increasing its toxicity.

Because of the potentially deleterious effects of compounds that activate CYP enzymes, improved methods are needed to determine which compounds activate CYP-mediated metabolism and, thus, might cause side-effects if administered to humans. These compounds may thereby be eliminated from drug development or chemically modified to generate related compounds with less ability to activate CYP enzymes.

SUMMARY OF THE INVENTION

The present invention provides screening systems and methods that facilitate the identification of compounds that activate or inhibit a constitutive androstane receptor (referred to as "CAR" or "CAR receptor"). Such CAR receptor-activating compounds are potentially toxic when administered to a mammal alone or in combination with other compounds, and are therefore preferably excluded from candidate drugs or drug development programs. Similarly, compounds that inhibit a CAR receptor may be administered to a mammal to decrease the CAR-mediated metabolism of a therapeutically active compound, potentially decreasing side-effects and re-establishing the therapeutic half-life of the compound in vivo. Such a decrease of metabolic activity may also be useful to decrease production of toxic products from appropriate precursor compounds.

Accordingly, in a first aspect, the invention features a transgenic mouse expressing a human CAR receptor. Preferably, the human CAR receptor is activated by phenobarbital. In various embodiments, phenobarbital increases the rate of human CAR-mediated induction of a CAR target gene or a transgene operably-linked to a CAR responsive promoter by at least 2, 5, 10, or 20-fold. In certain embodiments, 1,4-bis[2-(3,5-dichloropyridyloxy)]benzene increases the rate of human CAR-mediated induction of a CAR target gene or a transgene operably-linked to a CAR responsive promoter by less than 20, 10, 5, or 2-fold. In other embodiments, an activity of the human CAR receptor (e.g., induction of a CAR target gene) is increased by less than 200, 100, 50, or 25% by 1,4-bis[2-(3,5-dichloropyridyloxy)]benzene. In preferred embodiments, phenobarbital increases an activity of the human CAR receptor by at least 2, 5, 10, 20, or 40-fold more than the corresponding amount of 1,4-bis[2-(3,5-dichloropyridyloxy)]benzene increases the activity of the human CAR receptor. In other preferred embodiments, administration of acetaminophen to the mouse activates human CAR-mediated induction of a CAR target gene (e.g., CYP1A2, CYP3A11, or GSTPi). Preferably, administration to the mouse of an inhibitor of human CAR (e.g., an inverse agonist) decreases the level of activation of human CAR (e.g., reduces the induction of CYP1A2, CYP3A11, or GSTPi) by acetaminophen.

In preferred embodiments of the above aspect, the mRNA of the human CAR receptor includes a bovine growth hormone polyadenylation sequence. Preferably, the nucleic acid encoding the human CAR receptor is operably linked to an intronic sequence of a rabbit β-globin nucleic acid, which increases the expression of the human CAR receptor.

In a preferred embodiment, the transgenic mouse expressing a human CAR receptor does not express a substantially active murine CAR receptor or does not express any murine CAR receptor.

In another aspect, a transgenic mouse expressing human CAR exhibits induction of a xenobiotic response in the presence of a xenobiotic inducer. In one embodiment, the transgenic mouse of the present invention exhibits an induction or activation of a CAR target gene, such as CYP2B10 mRNA in response to PB. In another embodiment, the transgenic mice expressing human CAR does not demonstrate or exhibit an induction or activation of a CAR target gene in response to TCPOBOP.

In yet another aspect, the invention features a mouse having a mutation that reduces CAR receptor activity. Preferably, the activity of a murine CAR receptor is reduced by at least 20, 30, 40, 50, 60, 70, 80, 90, 95, or 100% compared the corresponding activity of a naturally-occurring murine CAR receptor. In some preferred embodiments, the mouse does not express a functional murine CAR receptor. In a preferred embodiment, the level of induction of a CAR target gene (e.g., CYP1A2, CYP3A11, or GSTPi) in response to acetaminophen administered to the mouse having a mutation in a CAR receptor is less that 10, 5, or 2-fold times the corresponding level of induction in a CAR null mouse that does not express CAR mRNA or protein.

In a further aspect, the present invention features a transgenic animal deficient of or lacking in a CAR gene. In a preferred embodiment, the transgenic animal of the present invention comprises a reduction or absence of native or naturally-occurring CAR receptor activity, and is preferably a mouse.

In various embodiments, the transgenic mouse of the present invention exhibits a decrease or absence of induction, expression, or activity of a CAR target gene in response to a xenobiotic inducer. In a preferred embodiment, the transgenic mouse exhibits a decrease or absence of induction, expression, or activity of a CAR target gene. In a particular embodiment, the transgenic mouse of the present invention exhibit a decrease or absence of CYP enzyme induction, activity, or expression in response to a xenobiotic inducer, such as PB or TCPOBOP.

In another embodiment, the transgenic mouse of the present invention does not exhibit hyperplasia or hypertrophy of the liver upon treatment with a xenobiotic inducer, including PB or TCPOBOP. Preferably, the transgenic mouse of the present invention does not exhibit hyperplasia or hypertrophy of the liver in response to treatment with either phenobarbital or TCPOBOP as exhibited in wild-type mice.

In a further embodiment, the transgenic mouse exhibits decreased metabolism of the CYP substrate zoxazolamine. In yet a further embodiment, the transgenic mouse exhibits a resistance to acetaminophen toxicity.

The present invention also provides cells derived from the transgenic animals of the present invention, such as cells that are isolated or present in a tissue or organ, and any cell lines or any progeny thereof.

The animals of the present invention may be used to determine whether a compound modulates the activity of a CAR receptor. In addition, methods are provided to determine whether the metabolism of a compound is regulated by modulation of the activity of a CAR receptor.

Accordingly, the invention also features a screening method for determining whether a compound activates a CAR receptor. This method involves administering a compound to a transgenic mouse expressing a human CAR receptor and measuring induction of a CAR target gene. The compound is determined to activate the CAR receptor if the compound mediates induction of the CAR target gene. In one preferred embodiment, a CAR receptor inverse agonist is also administered to the mouse expressing a human CAR receptor. Preferably, the CAR receptor inverse agonist is clotrimazole.

In another aspect, the invention features a screening method for determining whether a compound inhibits a CAR receptor. This method involves administering the compound to a transgenic mouse expressing a human CAR receptor and measuring expression of a CAR target gene in the presence and absence of the compound. The compound is determined to inhibit the CAR receptor if the compound decreases the expression of the CAR target gene. In one preferred embodiment, a CAR receptor agonist is also administered to the mouse expressing the human CAR receptor. Preferably, the CAR receptor agonist is a functional CAR receptor agonist that is specific for human CAR, and the agonist is administered after the compound is administered to the mouse.

In yet another aspect, the invention features a screening method for determining whether a compound modulates the activity of a CAR receptor. This method involves administering the compound to a transgenic mouse expressing a human CAR receptor and measuring a physiological effect mediated by the administration of the compound. The compound is determined to modulate the activity of the CAR receptor if the magnitude of the physiological effect in the mouse expressing the human receptor differs from that in a mouse having a mutation that reduces CAR receptor activity. In preferred embodiments, the physiological effect is assayed by measuring the toxicity or activity mediated by the administration of the compound or by measuring the half-life of the compound. In other preferred embodiments, the toxicity or activity is mediated by a metabolite of the compound. Preferably, the difference between the magnitude of the physiological effect in the mouse expressing the human CAR receptor as compared to a mouse having reduced CAR receptor activity is at least 2, 5, 10, or 20-fold. In other preferred embodiments, the magnitude of the physiological effect in a mouse having reduced CAR activity is at least 10, 25, 50, or 75% smaller or larger than the magnitude of the effect in the mouse expressing the human CAR receptor.

In still another aspect, the invention features a screening method for determining whether the metabolism of a compound is regulated by modulation of the activity of a CAR receptor. This method involves administering the compound to a transgenic mouse expressing a human CAR receptor and measuring the rate of metabolism of the compound. The metabolism of the compound is determined to be regulated by modulation of the activity of the CAR receptor if the rate of metabolism is faster in the mouse expressing the human receptor than in a mouse having reduced CAR receptor activity. Preferably, the rate of metabolism is at least 2, 5, 10, or 20-fold faster in the mouse expressing the human CAR receptor than in the mouse having reduced CAR receptor activity. In preferred embodiments, the rate of metabolism is determined by measuring the toxicity or activity mediated by the administration of the compound, measuring the half-life of the compound, or measuring the serum level of a liver enzyme. Preferably, these measurements are performed at more than 1, 3, or 5 time points after administration of the compound.

In another aspect, the invention provides a screening method for determining whether the metabolism of a first compound is modulated by a second compound. This method involves administering the first compound in the presence and absence of the second compound to a transgenic mouse expressing a human CAR receptor. A physiological effect that is mediated by the administration of the first compound is measured in the presence and absence of the second compound. The second compound is determined to modulate the metabolism of the first compound if the second compound effects a change in the physiological effect mediated by the administration of the first compound. In preferred embodiments, the physiological effect is assayed by measuring the toxicity or activity mediated by the administration of the first compound or measuring the half-life of the first compound. In various preferred embodiments, the toxicity or activity is mediated by a metabolite of the first compound. In still another preferred embodiment, the physiological effect is assayed by measuring the half-life of the first compound in the presence and absence of the second compound. The second compound is determined to activate the metabolism of the first compound if the second compound decreases the half-life, or the second compound is determined to inhibit the metabolism of the first compound if the second compound increases the half-life.

Similar methods for determining whether a compound modulates the activity of a CAR receptor or the metabolism of another compound may also be performed using a mouse having a mutation that reduces CAR receptor activity. For example, the invention features a screening method for determining whether a compound activates a CAR receptor. This method involves administering a compound to a mouse having a mutation that reduces CAR receptor activity and measuring induction of a CAR target gene. The compound is determined to activate the CAR receptor if the induction is smaller in the mouse having reduced CAR receptor activity than in a mouse having wild-type CAR receptor activity. In a preferred embodiment, a CAR receptor inverse agonist to is also administered to the mouse having reduced CAR receptor activity. Preferably, the inverse agonist is androstanol.

In another aspect, the invention features a screening method for determining whether a compound inhibits a CAR receptor. This method involves administering the compound to a mouse having a mutation that reduces CAR receptor activity and measuring expression of a CAR target gene in the presence and absence of the compound. The compound is determined to inhibit the CAR receptor if the decrease in expression effected by the compound is smaller in the mouse having reduced CAR receptor activity than in a mouse having wild-type CAR receptor activity. In one preferred embodiment, a CAR receptor agonist is also administered to the mouse having reduced CAR receptor activity. Preferably, the CAR receptor agonist is TCPOBOP, and the TCPOBOP is administered after the compound.

In still another aspect, the invention features a screening method for determining whether a compound modulates the activity of a CAR receptor. This method involves administering the compound to a mouse having a mutation that reduces CAR receptor activity and measuring a physiological effect mediated by the administration of the compound. The compound is determined to modulate the activity of the CAR receptor if the magnitude of the physiological effect in the mouse having reduced CAR receptor activity differs from that in a mouse having wild-type CAR receptor activity. Preferably, the difference between the magnitude of the physiological effect in the mouse having reduced CAR receptor as compared to a mouse having wild-type CAR receptor activity is at least 2, 5, 10, or 20-fold. In other preferred embodiments, the magnitude of the physiological effect in the mouse having reduced CAR activity is at least 10, 25, 50, or 75% smaller or larger than the magnitude of the effect in a mouse having wild-type CAR receptor activity. In yet other preferred embodiments, the physiological effect is assayed by measuring the toxicity or activity mediated by the administration of the compound or measuring the half-life of the compound. In another preferred embodiment, the toxicity or activity is mediated by a metabolite of the compound.

In still another aspect, the invention provides a screening method for determining whether the metabolism of a compound is regulated by modulation of the activity of a CAR receptor. This method involves administering the compound to a mouse having a mutation that reduces CAR receptor activity and measuring the rate of metabolism of the compound. The metabolism of the compound is determined to be regulated by modulation of the activity of the CAR receptor if the rate of metabolism is slower in the mouse having reduced CAR receptor activity than in a mouse having wild-type CAR receptor activity. Preferably, the rate of metabolism is at least 2, 5, 10, or 20-fold slower in the mouse having reduced CAR receptor activity than in a mouse having wild-type CAR receptor activity.

In preferred embodiments, the rate of metabolism is determined by measuring the toxicity or activity mediated by the administration of the compound, measuring the half-life of the compound, or measuring the serum level of a liver enzyme. Preferably, these measurements are performed at more than 1, 3, or 5 time points after administration of the compound.

In yet another aspect, the invention features a screening method for determining whether the metabolism of a first compound is modulated by a second compound. This method involves administering the first compound in the presence and absence of the second compound to a mouse having a mutation that reduces CAR receptor activity. A physiological effect that is mediated by the administration of the first compound is measured in the presence and absence of the second compound. The second compound is determined to modulate the metabolism of the first compound if the change effected by the second compound in the physiological effect mediated by the administration of the first compound is smaller in the mouse having reduced CAR receptor activity than in a mouse having wild-type CAR receptor activity. In preferred embodiments, the physiological effect is assayed by measuring the toxicity or activity mediated by the administration of the first compound or measuring the half-life of the first compound. In various preferred embodiments, the toxicity or activity is mediated by a metabolite of the first compound. In another preferred embodiment, the physiological effect is assayed by measuring the half-life of the first compound in the presence and absence of the second compound. The second compound is determined to activate the metabolism of the first compound if the decrease in the half-life effected by the second compound is smaller in the mouse having reduced CAR receptor activity than in a mouse having wild-type CAR receptor activity, or the second compound is determined to inhibit the metabolism of the first compound if the increase in the half-life effected by the second compound is smaller in the mouse having reduced CAR receptor activity than in a mouse having wild-type CAR receptor activity.

The above screening methods may be carried out using transgenic mouse expressing a human CAR receptor, for example, any such transgenic mouse described herein.

The invention also features methods for preventing, stabilizing, or treating toxicity associated with CAR-mediated metabolism of a xenobiotic by administering an inhibitor of CAR receptor expression and/or activity to a mammal (e.g., a human). Accordingly, in one such aspect, the invention features a method for preventing, stabilizing, or treating an adverse effect or symptom associated with one or more hepatotoxic agents (e.g., acetaminophen and/or phenobarbital) in a mammal (e.g., a human) by administering to a mammal (for example, a human) one or more compounds that inhibit the expression and/or activity of a CAR receptor in the mammal.

In preferred embodiments of various aspects of the invention, the mouse having a mutation that reduces CAR receptor activity is a transgenic animal. Preferably, the mutation that reduces CAR receptor activity substantially eliminates CAR receptor activity. In yet other preferred embodiments, the mouse having a mutation that reduces CAR receptor activity and the mouse having wild-type CAR receptor activity have the same genotype except for a mutation in the CAR receptor gene, promoter, or regulatory sequence. In still other preferred embodiments, the mouse having wild-type CAR receptor activity is a transgenic mouse expressing a human CAR receptor. Preferably, the mouse expressing a human CAR receptor does not express a substantially active murine CAR receptor or does not express any murine CAR receptor.

In other preferred embodiments, at least one of the compounds tested in the screening methods of the invention is a member of a library of as few as 2 or 5 compounds to as many as 10, 20, 50, or more compounds, all of which are simultaneously administered to the mouse. Preferred routes of administration of the compounds include oral, intramuscular, intravenous, parenteral, intraarticular, intraperitoneal, subcutaneous, or any other suitable route. Preferably, a compound that activates a CAR receptor or a compound whose metabolism is regulated by modulation of the activity of a CAR receptor is eliminated from drug development. If a first compound activates the metabolism of the second compound, then the first compound, the second compound, or both compounds are preferably eliminated from drug development. It is also contemplated that other animal models, such as a rat or other rodent having reduced CAR receptor activity or expressing a human CAR receptor, could be used in any of the various aspects of the invention.

The present invention provides a number of advantages. For example, the methods of the present invention may be used to facilitate the identification of analogs of a compound that have reduced or undetectable ability to activate a CAR receptor, and thus are expected to have fewer side-effects or a longer half-life in vivo. In addition, because murine and human CAR receptors have somewhat different substrate specificities, the use of transgenic mice expressing a human CAR receptor in the methods of the present invention may more accurately predict the modulation of CAR receptor toxicity or half-life of a compound when administered to humans. Moreover, the present assays may be easily and rapidly performed.

Other features and advantages of the invention will be apparent from the following detailed description and from the claims.

Definitions

The following terms have the meanings ascribed to them below unless specified otherwise.

As used herein, "CAR receptor activity" refers to CAR-mediated induction of a gene, denoted a "CAR target gene," or a transgene operably-linked to a CAR responsive promoter.

The term "mutation" refers to an alteration in a nucleic acid sequence such that the amino acid sequence encoded by the nucleic acid sequence has at least one amino acid alteration as compared to the naturally-occurring sequence. The mutation may, without limitation, be an insertion, deletion, frameshift mutation, or missense mutation. Alternatively, the mutation may alter the sequence of a CAR receptor promoter, transcriptional regulatory sequence, or translational regulatory sequence such that a smaller amount of CAR mRNA or protein is expressed. Preferably, the mutation results in at least a 25, 35, 50, 70, 80, 90, 95, 99, or 100% reduction in the activity of the encoded CAR receptor compared to the activity of a naturally-occurring CAR receptor. In another preferred embodiment, the level of induction of a CAR target gene in response to a xenobiotic administered to a mouse having a mutation in a CAR receptor is less that 10, 5, or 2-fold times the corresponding level of induction in a CAR null mouse that does not express CAR mRNA or protein.

The term "transgenic" refers to any cell or organism which includes a DNA sequence which is inserted by artifice into a cell and becomes part of the genome of the organism which develops from that cell. As used herein, the transgenic organism is generally a transgenic non-human mammal, preferably, a rodent such as a mouse.

The phrase "substantially eliminates CAR receptor activity" means the reduction of CAR receptor activity by 25, 35, 50, 70, 80, 90, 95, 99, or 100% compared to the activity of a naturally-occurring CAR receptor. In another preferred embodiment, the level of residual CAR receptor activity is no greater than 10, 5, or 2 times the corresponding level of CAR receptor activity in a CAR null mouse that does not express CAR mRNA or protein.

The phrase "a substantially active murine CAR receptor" means having at least 30, 60, 80, 90, 95, or 100% of the CAR receptor activity of the naturally-occurring murine CAR receptor encoded by SEQ ID NO: 26 (GenBank Accession No. AF009327)in a normal murine host (Choi et al., J. Biol. Chem. 272:23565–23571, 1997) The predicted amino acid sequence for the murine CAR receptor is SEQ ID NO: 1.

The phrase "a human CAR receptor" means a protein that has an amino acid sequence at least 75, 80, 90, 95, 99, or 100% identical to the amino acid sequence of the naturally-occurring human CAR receptor, encoded by SEQ ID NO: 25 (GenBank Accession No. Z30425)(Baes et al., Mol. Cell. Bio. 14:1544–1551, 1994) and that has at least 50, 75, 80, 90, 95, or 100% of the CAR receptor activity of a naturally-occurring human CAR receptor assayed under identical conditions. The predicted amino acid sequence for the human CAR receptor is SEQ ID NO: 2. It is also contemplated that the expressed human CAR receptor may be a fragment having an amino acid sequence at least 75, 80, 90, 95, 99, or 100% identical to the corresponding region of a naturally-occurring human CAR receptor and having at least 60, 80, 90, 95, or 100% of the CAR receptor activity of a naturally-occurring human CAR receptor. In addition, a human CAR receptor is inhibited by clotrimazole, an inverse agonist of human, but not murine, CAR (Moore et al., J Biol Chem. 275:15122–15127, 2000).

As used herein "naturally-occurring murine or human CAR receptor" refers to a protein with an amino acid sequence identical to that of a murine or human CAR receptor found in nature, such as the murine CAR receptor encoded by GenBank Accession No. 2267575 or the human CAR receptor encoded by GenBank Accession No. 458541.

The phrase "activation of a CAR receptor" means an increase in the rate of the CAR-mediated induction of a CAR target gene, or a transgene operably-linked to a CAR responsive promoter. Preferably, the increased induction of the CAR target gene or transgene in a mouse results in a 2, 5, 10, or 20-fold increased level of the encoded mRNA or protein, increased enzymatic activity of the CAR target gene, increased relative liver mass, increased release of a liver enzyme such as alanine aminotransferase into the serum, or increased DNA synthesis in the liver, as measured using the assays described herein. In another preferred embodiment, the increased induction is 2, 5, 10, or 20-fold greater in a mouse having wild-type CAR receptor activity than in a mouse having a mutation that reduces CAR receptor activity.

In one preferred embodiment, the candidate activator of a CAR receptor and a CAR receptor inverse agonist are administered to a mouse having a mutation that reduces CAR receptor activity or a mouse expressing a human CAR receptor. The level of induction of a CAR target gene is measured in the presence and absence of the candidate activator to determine whether the candidate activator effects an increase in the level of induction of the CAR target gene. The administration of the CAR receptor inverse agonist may decrease the initial level of induction of the CAR target gene and thus facilitate the detection of an increase in the induction mediated by the candidate activator.

The phrase "inhibit a CAR receptor" means a decrease in the rate of induction of a CAR target gene or transgene operably-linked to a promoter of a CAR target gene. Preferably, the decreased induction of the CAR target gene or transgene in a mouse results in a 2, 5, 10, or 20-fold decreased level of the encoded mRNA, protein, enzymatic activity, relative liver mass, release of a liver enzyme into the serum, or DNA synthesis in the liver, as determined using the assays described herein. In another preferred embodiment, the decrease in the level of induction is 2, 5, 10, or 20-fold greater in a mouse having wild-type CAR receptor activity than in a mouse having a mutation that reduces CAR receptor activity.

In one preferred embodiment, the candidate inhibitor of a CAR receptor and a CAR receptor agonist are administered to a mouse having a mutation that reduces CAR receptor activity or a mouse expressing a human CAR receptor. The level of induction of a CAR target gene is measured in the presence and absence of the candidate inhibitor to determine whether the candidate inhibitor effects a decrease in the level of induction of the CAR target gene. The administration of the CAR receptor agonist may increase the initial level of induction of the CAR target gene and thus facilitate the detection of a decrease in the induction mediated by the candidate inhibitor.

The phrase "having wild-type CAR receptor activity" or "having naturally-occurring CAR receptor activity" means having a substantially identical activity to that of a naturally-occurring murine or human CAR receptor. By "substantially identical," as used herein, is meant at least 80, 90, 95, 99, or 100% of the activity of a naturally-occurring CAR receptor. The ability of a CAR receptor to induce a CAR target gene or a transgene operably-linked to a CAR responsive promoter may be routinely measured using assays for the encoded mRNA, protein, or enzymatic activity or assays for relative liver mass, a liver enzyme released into the serum, or DNA synthesis.

As used herein, "modulate the metabolism" refers to an increase or decrease in the rate of a CYP-catalyzed reaction of a compound, such as the oxidation of the compound. For example, the rate of metabolism of the compound may be measured as the rate of formation of the oxidized product or the formation of a subsequent product generated from the oxidized intermediate. Alternatively, the rate of metabolism may be represented as the half-life or rate of disappearance of the initial compound or as the change in toxicity or activity of the initial compound or a metabolite generated in a CYP-dependent manner from the initial compound. For example, a second compound is said to modulate the metabolism of a first compound if the half-life, toxicity, or activity of the first compound is increased or decreased in the presence of the second compound. Preferably, the change in the half-life, toxicity, or activity of the first compound or a metabolite of the first compound is at least 25, 50, 100, 200, 500, or 1000% of the corresponding half-life, toxicity, or activity in the absence of the second compound. In another preferred embodiment, the change in the half-life, toxicity, or activity is at least 2, 5, 10, or 20-fold greater in a mouse having wild-type CAR receptor activity than in a mouse having a mutation that reduces CAR receptor activity. In various preferred embodiments, a second compound mediates a change of at least 2, 5, 10, or 20-fold in the magnitude of the half-life, activity, or toxicity of a first compound or a metabolite of the first compound, as measured in any of the assays described herein.

The half-life may be measured by determining the amount of the compound present in samples taken from the mouse at various time points; the amount of the compound may be quantified using standard methods such as high-performance liquid chromatography, mass spectrometry, western blot analysis using compound specific antibodies, or any other appropriate method. In preferred embodiments, a reaction required for the toxicity or activity of the first compound or a metabolite of the first compound (such as the reaction of an activated metabolite with DNA, RNA, or protein) is at least 25, 50, 100, 200, 500, or 1000% of the corresponding rate in the absence of the second compound. The toxicity of the first compound or a metabolite of the first compound may also be measured by determining the relative liver mass, amount of a liver enzyme released into the serum, or rate of DNA synthesis in the liver of a mouse. It is also contemplated that the rate of a reaction catalyzed by another enzyme involved in xenobiotic metabolism that is downstream of a CAR receptor may also be increased or decreased. In one preferred embodiment, the second compound modulates the metabolism of the first compound by activating or inhibiting a CAR receptor.

As used herein "activity of a compound" refers to a biological effect mediated by a compound. Examples of possible activities of compounds include binding to other molecules, modulation of a binding interaction between molecules, modulation of the rate of catalysis of an enzyme, induction of physiological or behavioral changes, or any other therapeutically relevant activity of a compound.

As used herein "physiological effect" means a toxic effect, an activity, or the modulation of the expression of a CAR target gene mediated by a compound, as described above. For compounds that are metabolized to form a metabolite that has a different level of toxicity or activity as the initial compound, the physiological effect of the compound may also be measured by determining the half-life of the compound.

The term "promoter" refers to a minimal sequence sufficient to direct transcription of an operably-linked gene. The promoter may also be operably-linked to 5' regulatory sequences that modulate the transcription of the gene.

BRIEF DESCRIPTION OF THE DRAWINGS

FIG. 1A is a schematic illustration of the targeted disruption of the mouse CAR gene. Boxes represent exons. Exons 2 and 3 (hatched boxes) contain the DNA binding domain. Homologous recombination resulted in replacement of Exons 1 and 2 with the β-gal and neo resistance genes.

Restriction enzyme sites for ApaI (A), HindIII (H3), NotI (N), SalI (S), and XbaI (X) are indicated.

FIG. 1B is a picture of a gel showing genotype analysis by Southern blotting. Genomic DNA from tail samples was digested with HindIII and hybridized with the 3' probes. The 10 Kb and 15 Kb bands were generated from wild-type and mutant alleles, respectively.

FIG. 1C is a picture of a gel showing Northern blot analysis. The murine CAR cDNA was used as a probe to determine the level of CAR mRNA expressed in liver of wild-type and CAR +/− or −/− animals.

Figure 2A:
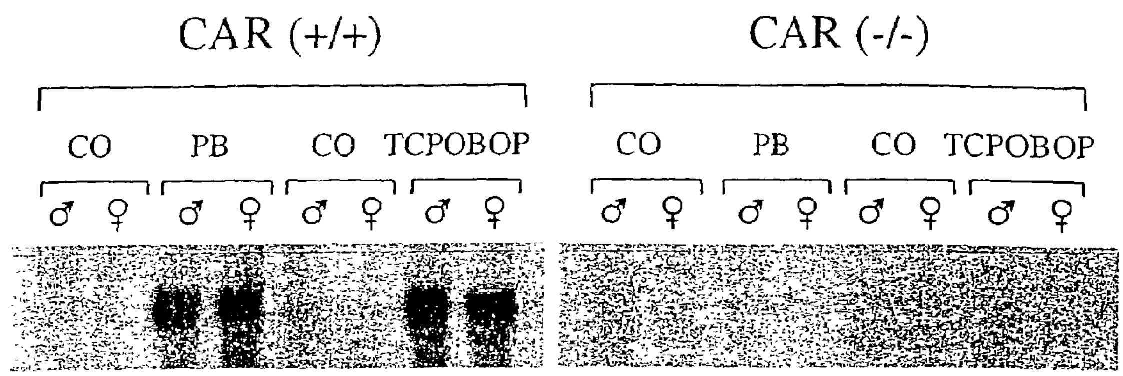

FIG. 2A is a picture of a representative Northern blot of xenobiotic activation of the CYP2B10 gene by CAR in a liver sample. Mice (8–10 weeks old, 3 mice per treatment) were treated with corn oil (CO) for 6 or 24 hours, PB for 24 hours, or TCPOBOP for 6 hours.

Figure 2B:
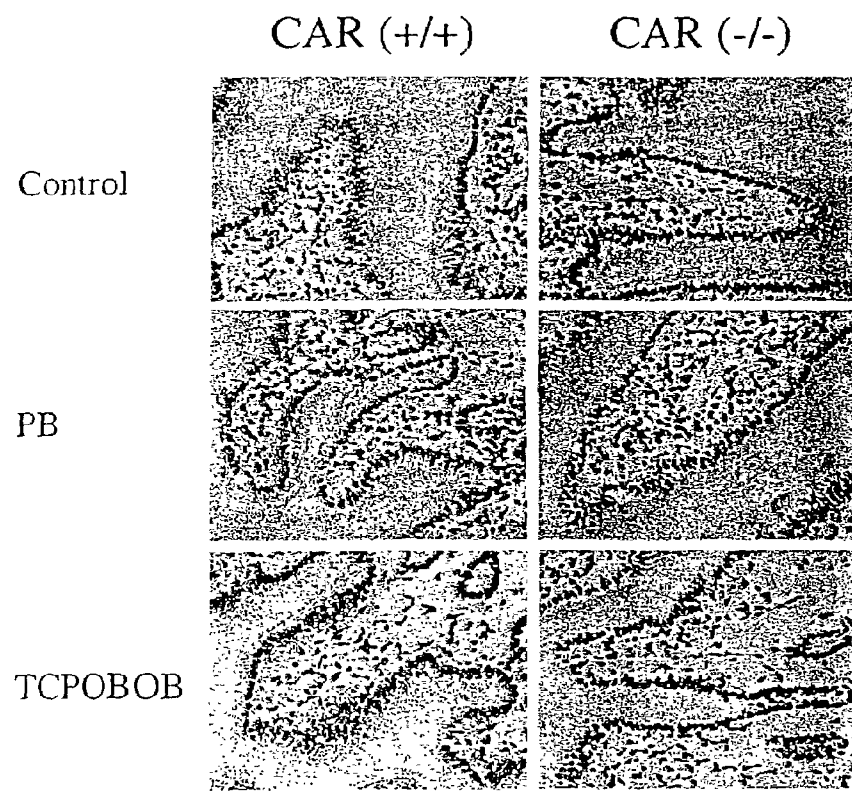

FIG. 2B is a series of photographs of in situ hybridization of a piece of small intestine from mice treated with PB or TCPOBOP for 3 days. The in situ hybridization was performed with a [$^{35}$S]-labeled antisense CYP2B10 riboprobe. The number of grains per cell is not significantly different in the CAR −/− animals, with or without xenobiotic treatments. The number of grains per cell is approximately two-fold higher in the untreated wild-type mice than in the CAR receptor knockout mice, and the number of grains per cell in the xenobiotic-treated wild-type mice is approximately two-fold higher than in the untreated wild-type mice.

Figure 3A:
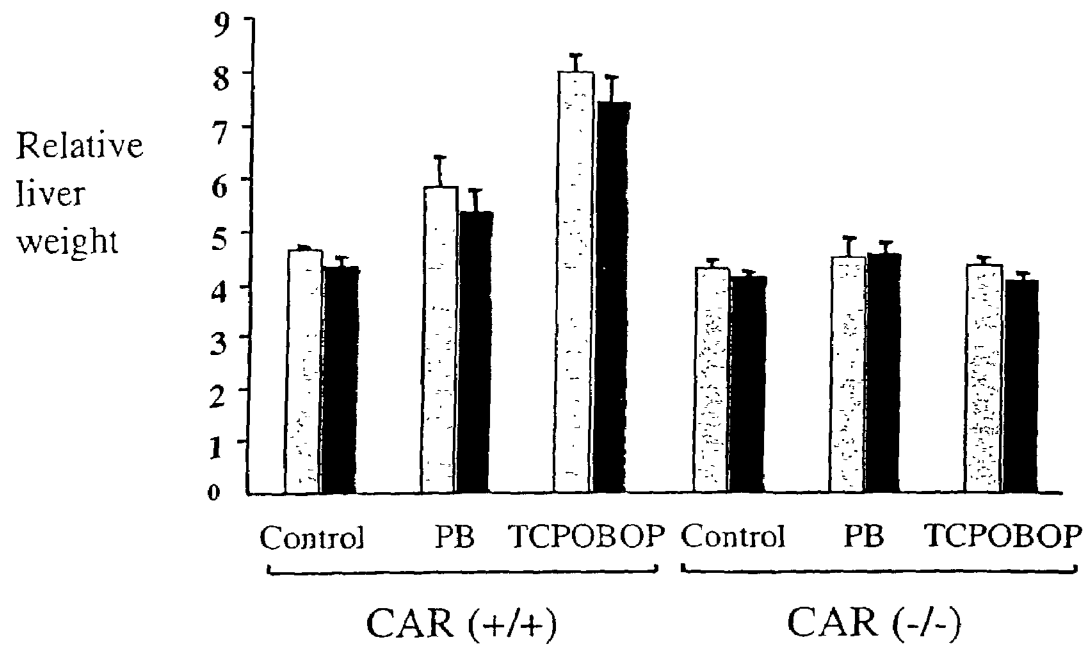

FIG. 3A is a bar graph showing the liver enlargement and hepatocyte proliferation by PB or TCPOBOP. Mice (8–10 weeks old) were treated with PB or TCPOBOP for 3 days, and then both liver mass and body weight were measured. The data is presented as percentage of liver mass relative to total body weight.

Figure 3B:
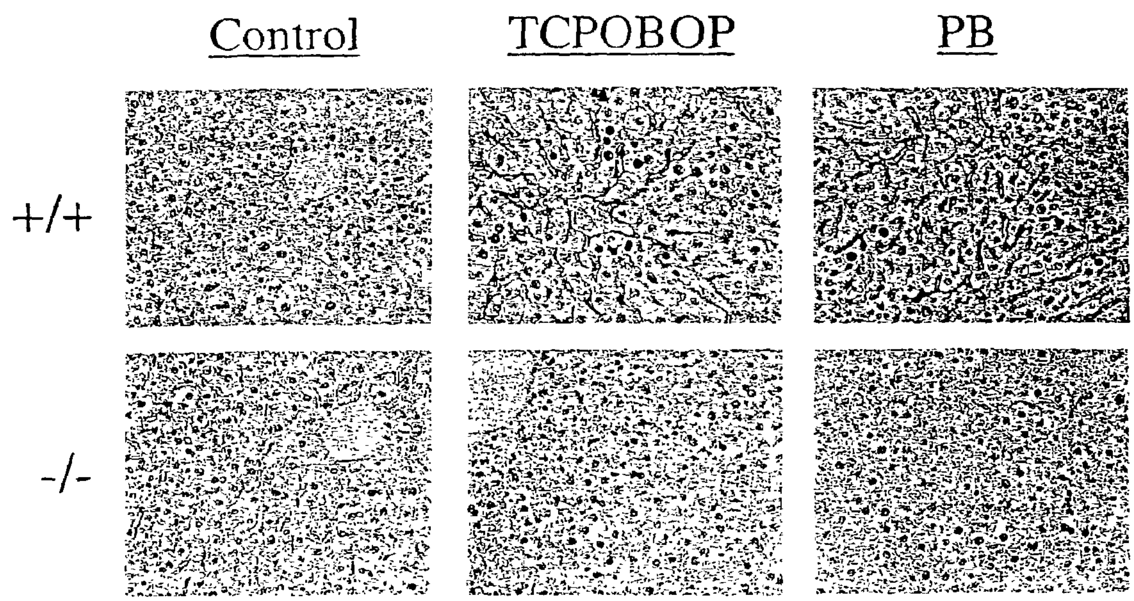

FIG. 3B is a set of pictures of PB-treated, TCPOBOP-treated, or control mice that were treated with BrdU for two hours before their liver tissues were harvested. The representative microphotography illustrates the presence of BrdU-positive hepatocytes only in PB- or TCPOBOP-treated wild-type animals.

Figure 4:
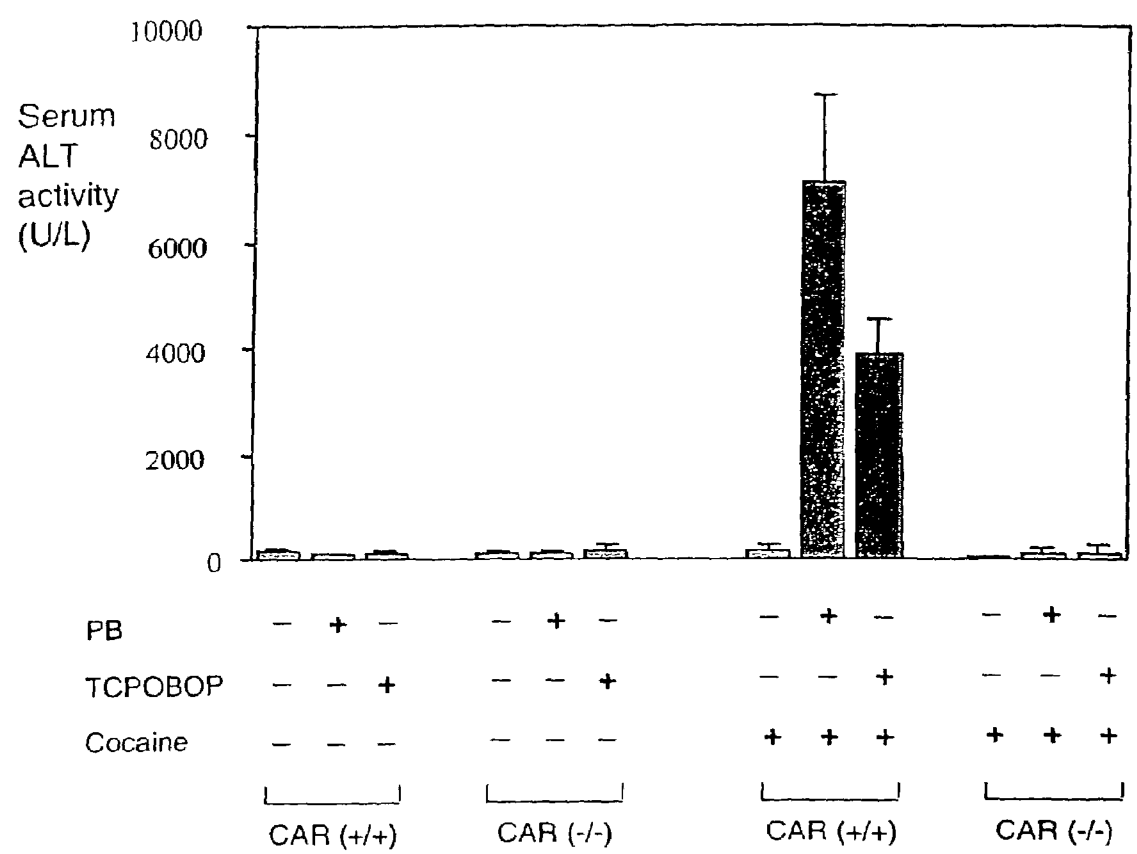

FIG. 4 is a bar graph showing the effect of PB or TCPOBOP on cocaine-mediated hepatotoxicity, measured as serum alanine aminotransferase (ALT) activity. Male mice were pretreated with PB or TCPOBOP for three days. Twenty-four hours after the last dose, one injection of cocaine was given to the animals. Blood was drawn 20 hours after cocaine treatment for determination of serum ALT activity.

FIGS. 5A and 5B are pictures of representative Northern blots of xenobiotic activation of the murine CYP3A11 gene by murine CAR in a liver sample. Mice (8–10 weeks old, 3 mice per treatment) were treated with corn oil (CO) for 6 or 24 hours, PB for 24 hours, or TCPOBOP for 6 hours.

Figure 6:
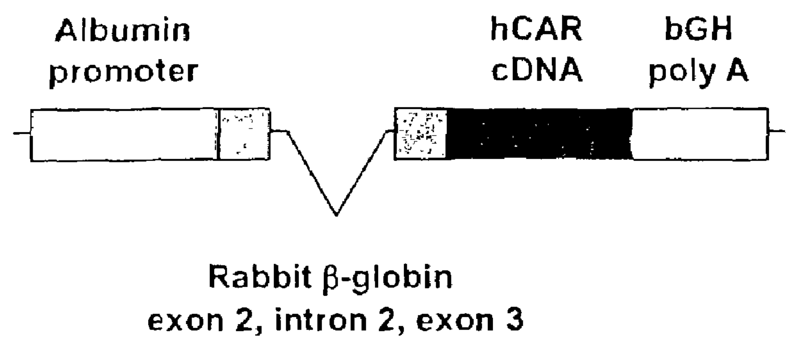

FIG. 6 is a schematic illustration of the transgene construct used to generate mice expressing human CAR. This transgenic construct contains the liver specific, albumin promoter operably linked to the cDNA sequence for human CAR. To enhance the expression and stability of human CAR transcripts, a region from an abundantly expressed gene, rabbit β-globin, and the polyadenylation (poly A) sequence from bovine growth hormone were also added to this construct.

Figures 7A, 7B, 7C:
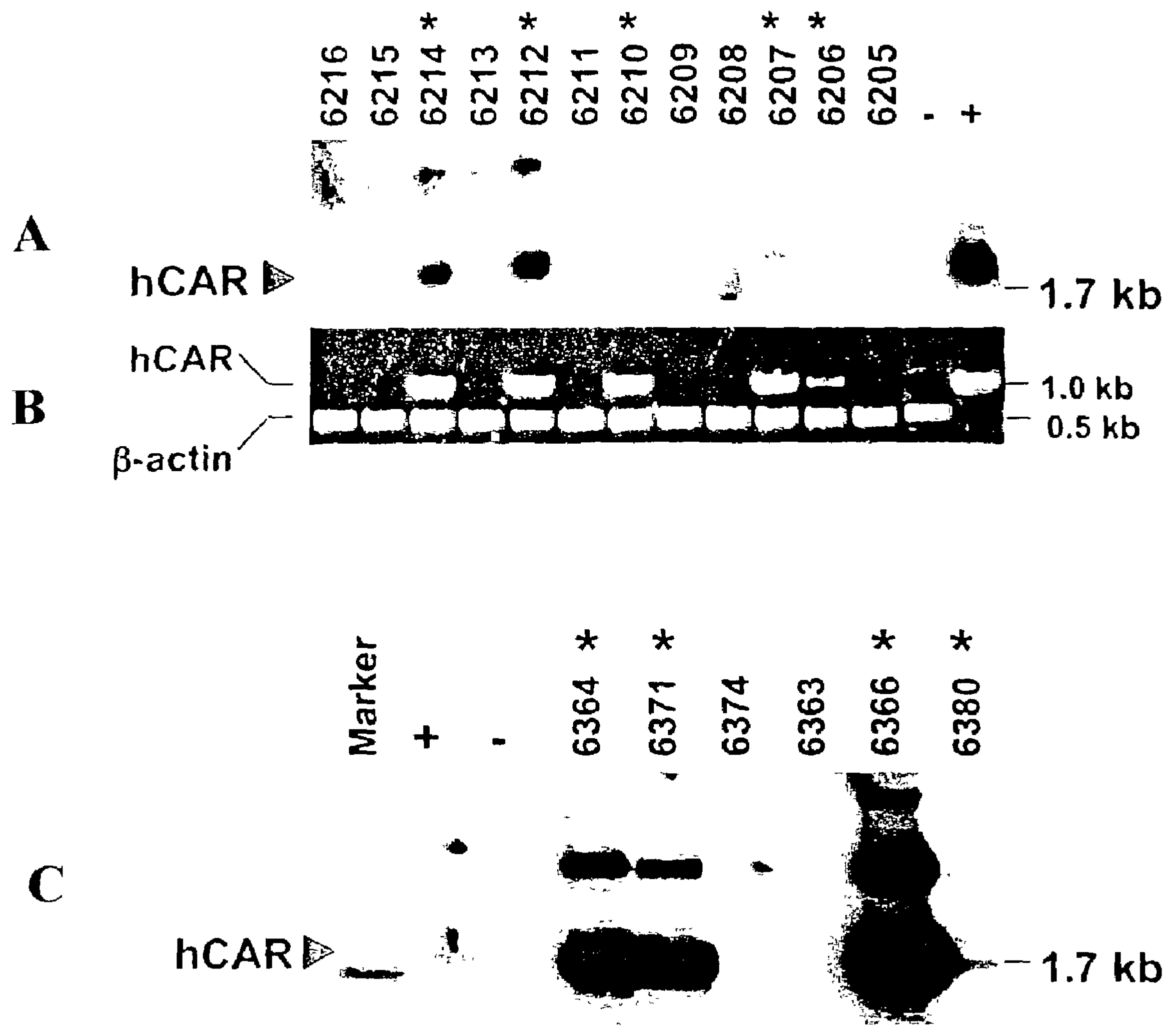

FIGS. 7A and 7C are pictures of representative Southern blots of genomic DNA from mice generated using the human CAR transgene construct. The lanes containing DNA that bound to the human CAR probe are labeled with as asterisk.

FIG. 7B is a representative gel showing the PCR amplification of genomic DNA from mice generated using the human CAR transgene construct. The production of a PCR product using primers specific for human CAR confirmed the results of the Southern blot analysis in FIGS. 7A and 7C. Based on these analyses, nine of the mice were identified as transgenic mice containing DNA encoding human CAR.

Figure 8:
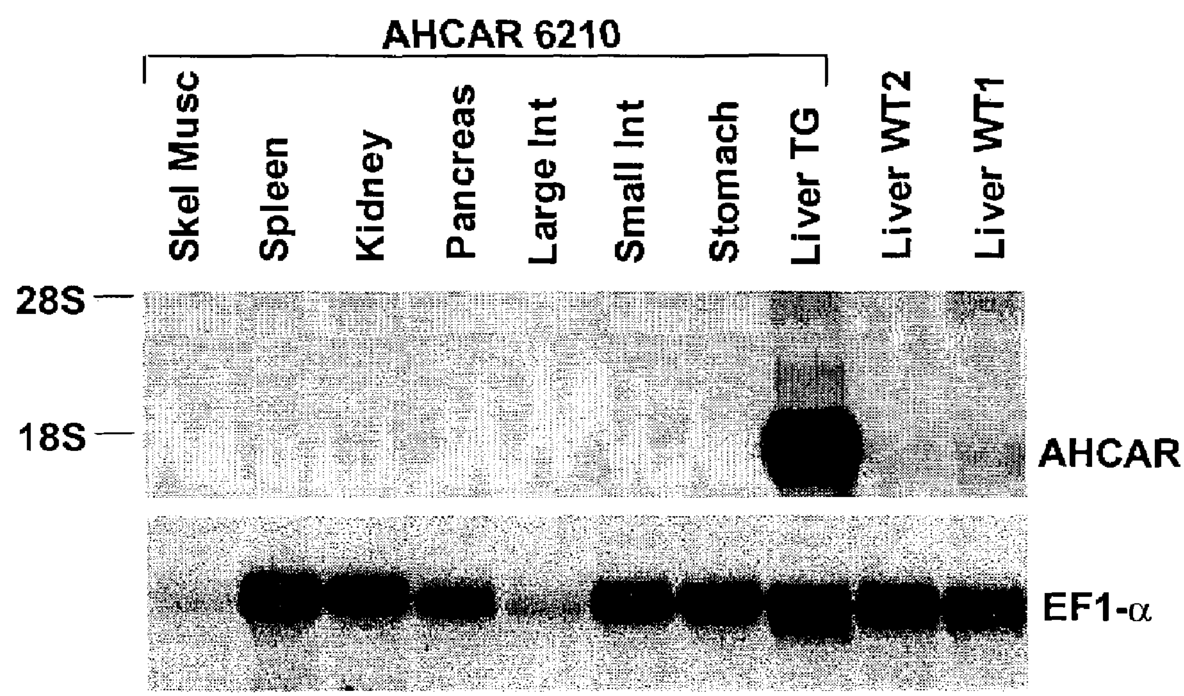

FIG. 8 is a Northern blot illustrating expression of human CAR mRNA transcripts in one of the humanized CAR mice lines (line 6210). Human CAR mRNA was specifically expressed in the liver.

Figure 9:
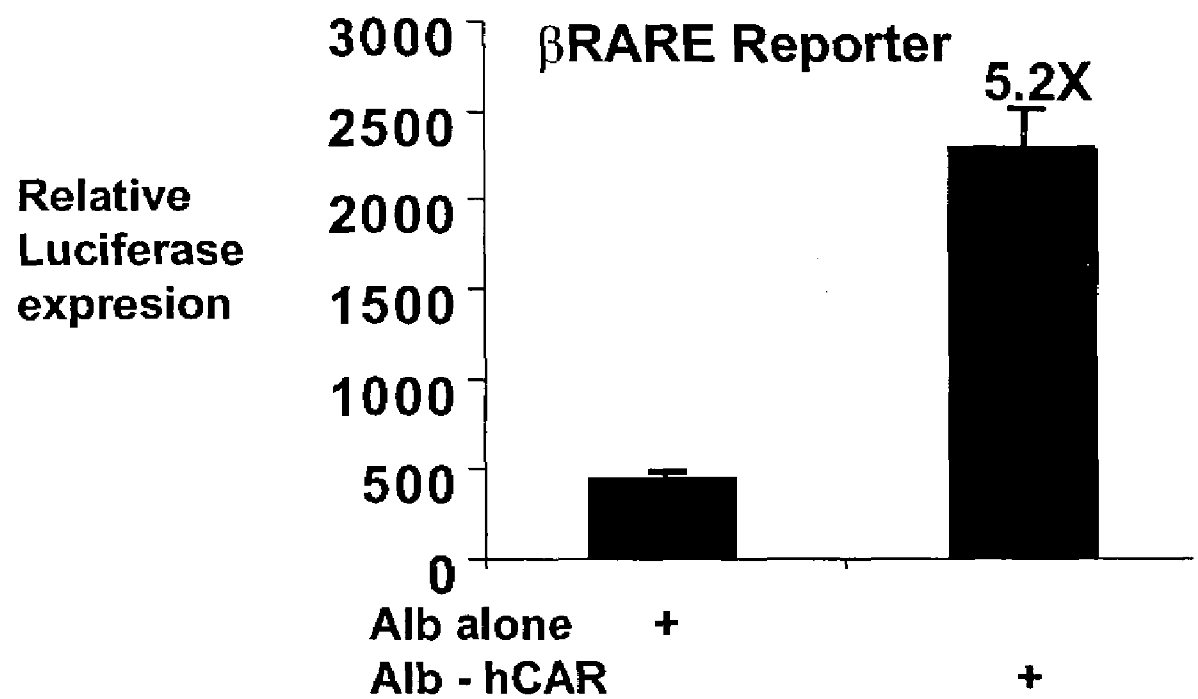

FIG. 9 is a bar graph illustrating the induction of a CAR reporter gene in HepG2 cells transiently transfected with the human CAR transgenic construct illustrated in FIG. 6. These results indicate that this transgenic construct encodes functional human CAR which can activate the expression of a reporter gene operably liked to a CAR responsive promoter. These transfected cells may be used to screen candidate compounds to determine whether they activate or inhibit human CAR.

Figure 10:
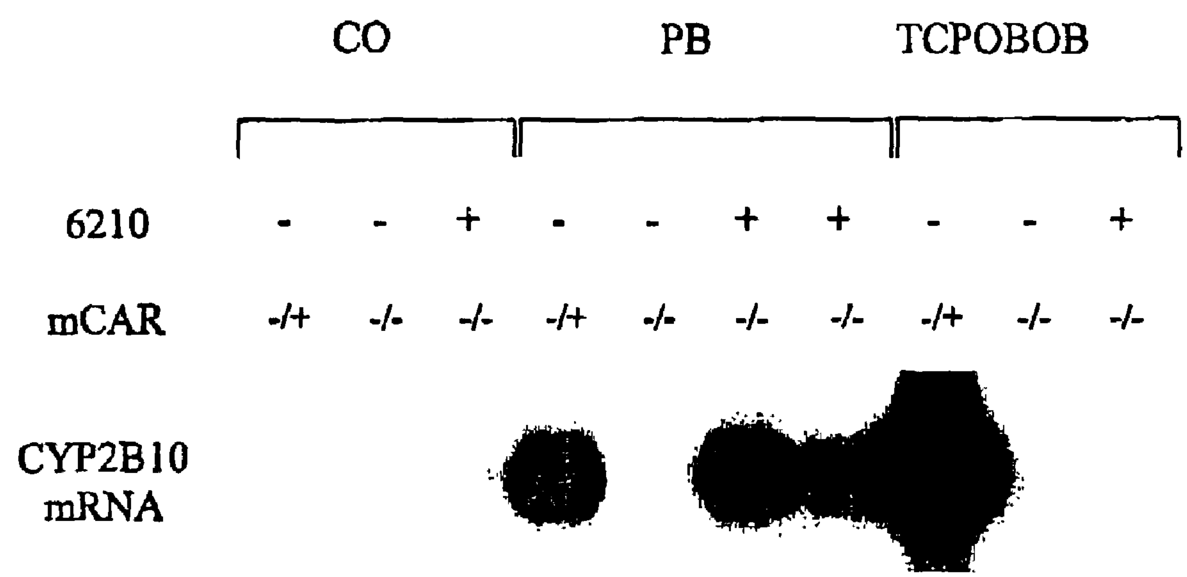

FIG. 10 is a picture of a Northern blot illustrating induction of the CAR target gene CYP2B10 by PB, but not by TCPOBOP, in humanized CAR mice lacking a functional murine CAR gene. Animals with the indicated genotypes (with, "+," or without, "−," the line 6210 hCAR transgene, and heterozygous, "−/+," or homozygous, "−/−," for the murine CAR gene mutation) were treated with PB or TCPOBOP for 24 hours. Total RNA was prepared from the livers of the individual mice, and CYP2B10 mRNA expression was assessed by Northern blotting.

Figure 11A:
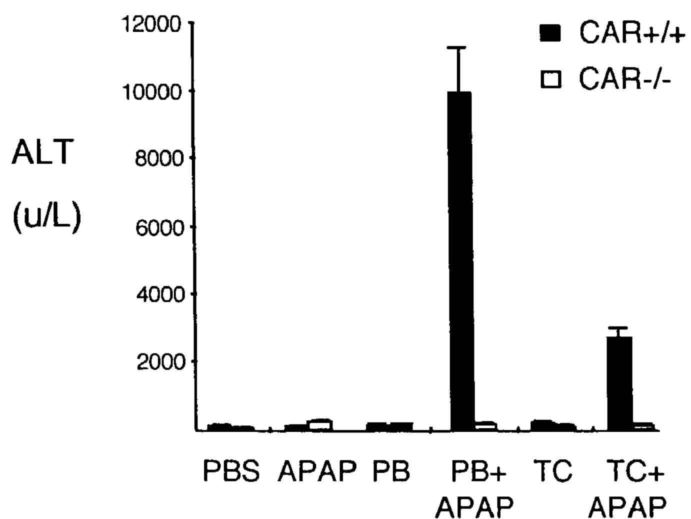
Figure 11B:
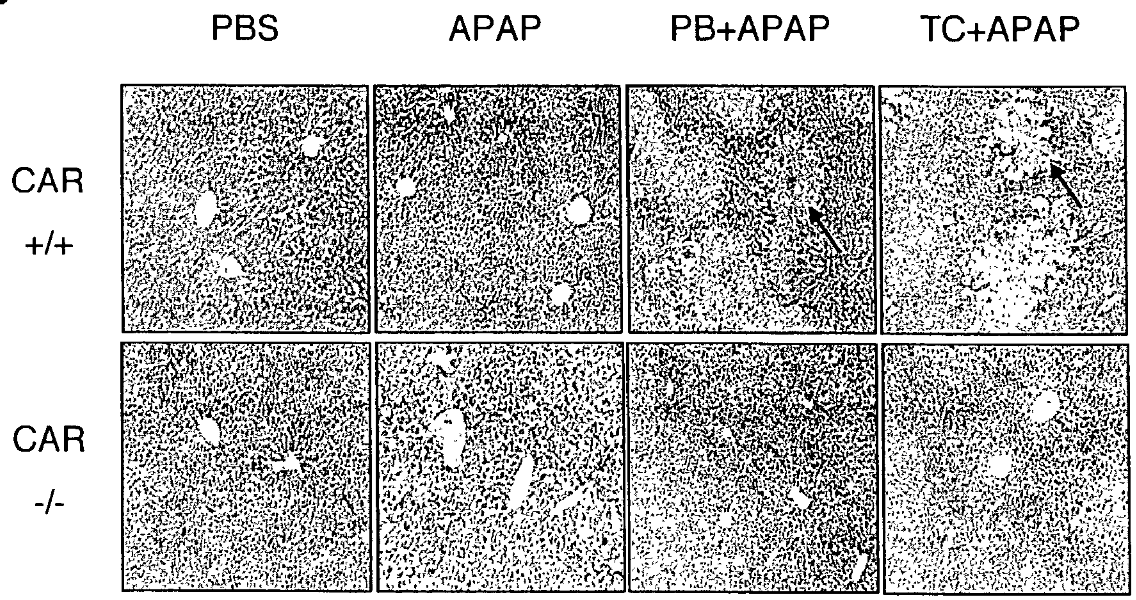
Figure 11C:
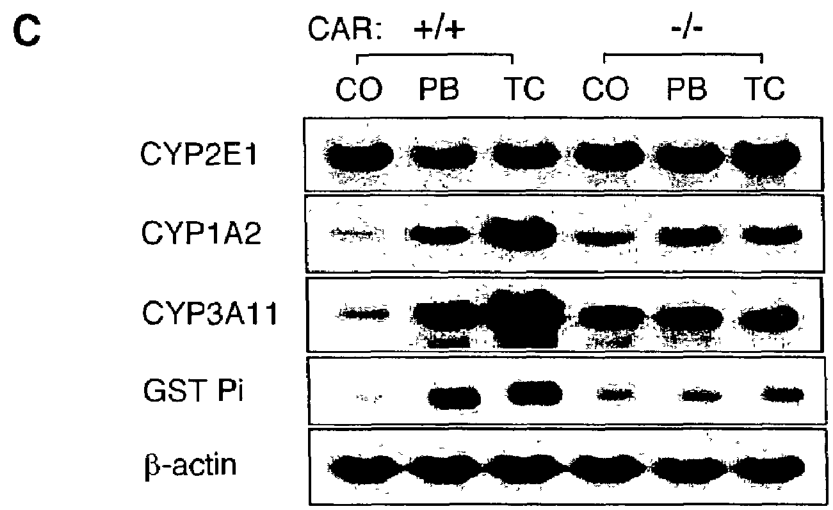
Figure 11D:
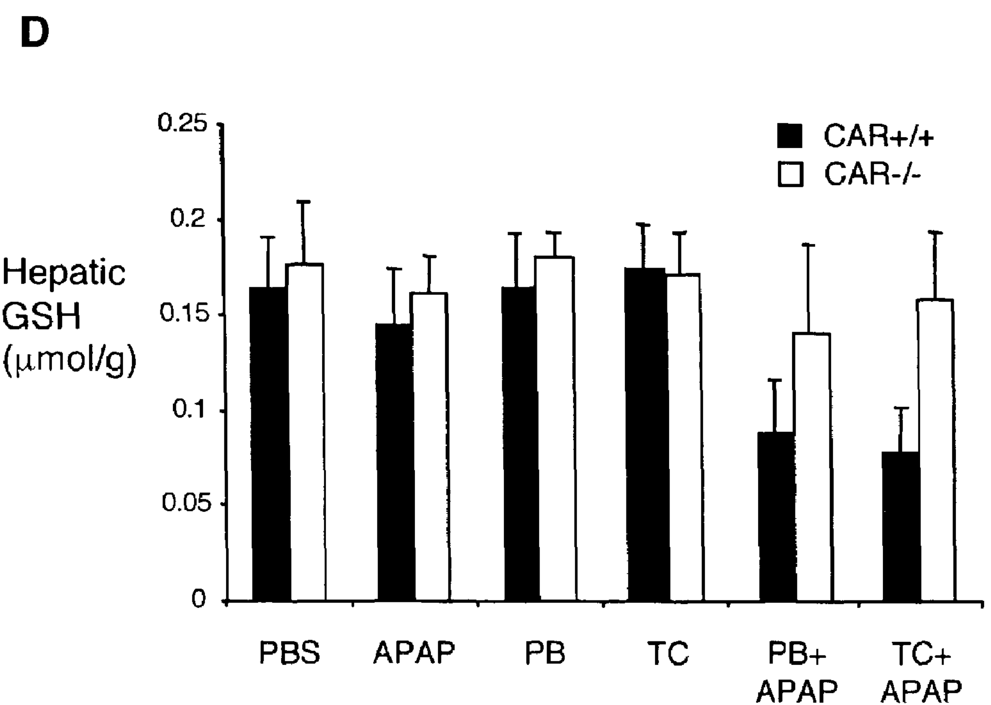

FIGS. 11A–11D demonstrate that CAR activation induces APAP toxicity. CAR (+/+) or CAR (−/−) animals pretreated with phenobarbital (PB), TCPOBOP (TC), or vehicle alone were administered a 250 mg/kg dose of APAP by intraperitoneal injection (n=5–7 per treatment group) (FIG. 11A). Serum was collected and alanine aminotransferase (ALT) levels were measured after 24 hours. Liver sections from different treatments were examined by histological staining (FIG. 11B). Liver samples from all treated animals were analyzed but only representative histology is presented. PB or TCPBOBP pretreated livers from wild-type animals showed extensive hepatic centrilobular necrosis as indicated by arrows. CAR (+/+) or CAR (−/−) animals were pretreated with PB, TCPOBOP (TC), or vehicle alone for three days (FIG. 11C). Total liver RNA was prepared and subjected to Northern blot analysis with indicated probes. Liver samples treated as indicated were collected two hours after APAP and GSH levels were measured (n=5–7) (FIG. 11D). The hepatic GSH levels in the PB and TC pretreated wild-type animals were significantly different from those of both the CAR (+/+) animals injected with vehicle alone (p=0.011 and p=0.0046, respectively) and CAR (−/−) animals pretreated with PB and TC (p=0.034 and p=0.026, respectively).

Figure 12A:
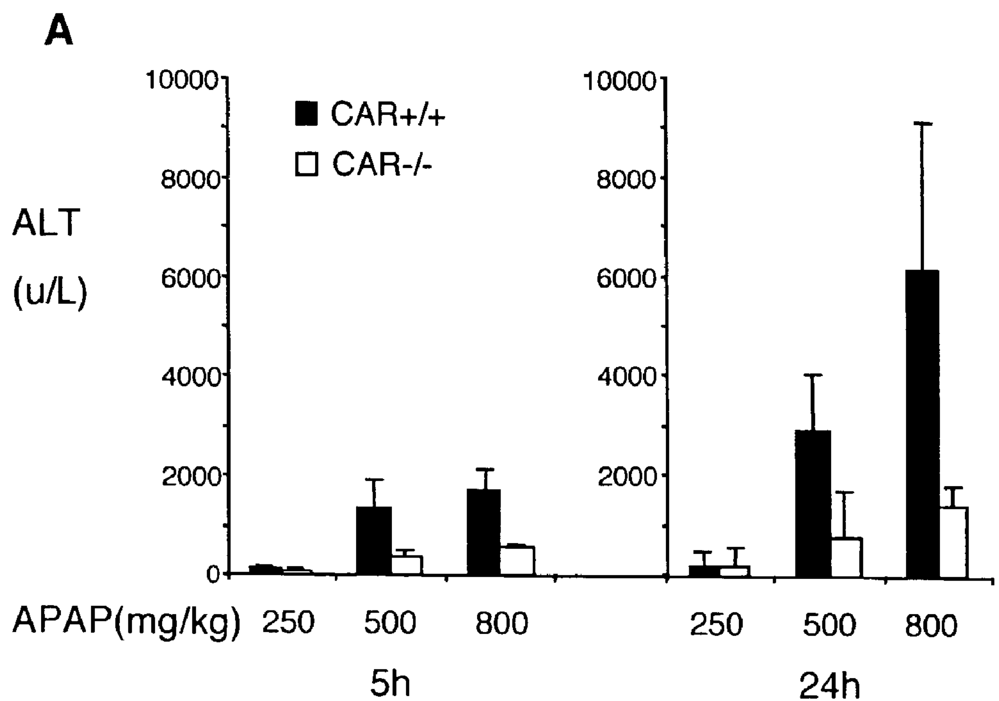
Figure 12B:
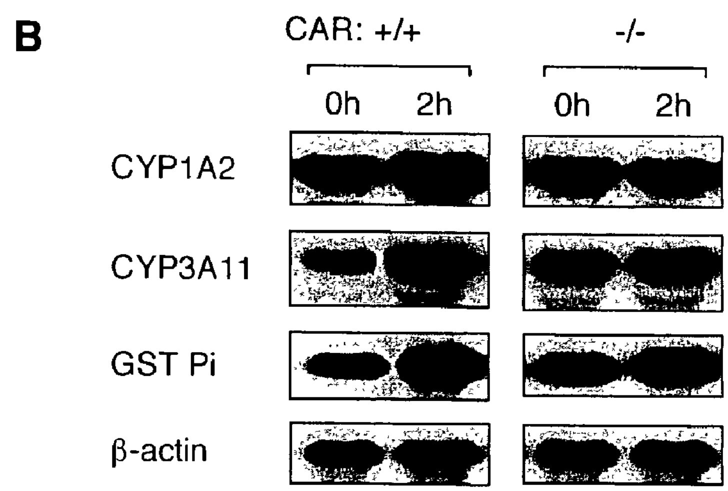

FIGS. 12A and 12B show that CAR (−/−) mice are resistant to APAP toxicity. CAR (+/+) and CAR (−/−) animals were given 250 mg/kg, 500 mg/kg, or 800 mg/kg doses of APAP, respectively (FIG. 12A). Blood samples were collected 5 or 24 hours later and serum alanine aminotransferase (ALT) levels were measured (n=5–7). At the dose of 500 mg/kg and 800 mg/kg, CAR (−/−) animals were significantly less sensitive than wild-type animals to APAP toxicity (with 500 mg/kg, p=0.019 for five hours and p=0.026 for 24 hours; with 800 mg/kg, p=0.016 for five hours and p=0.0008 for 24 hours). Total liver RNA was prepared from 500 mg/kg APAP treated CAR (+/+) and CAR (−/−) livers at 0 and 2 hours as indicated. Total RNA (10 μg) from different samples was subjected to Northern blot analysis with indicated probes (FIG. 12B). The same blot was stripped and re-probed with β-actin as loading control. Quantitation of mRNA levels by densitometry showed that the induction of CYP1A2, CYP3A11, and GSTPi was approximately 2.8, 4.4 and 3.9 fold, respectively.

Figure 13:
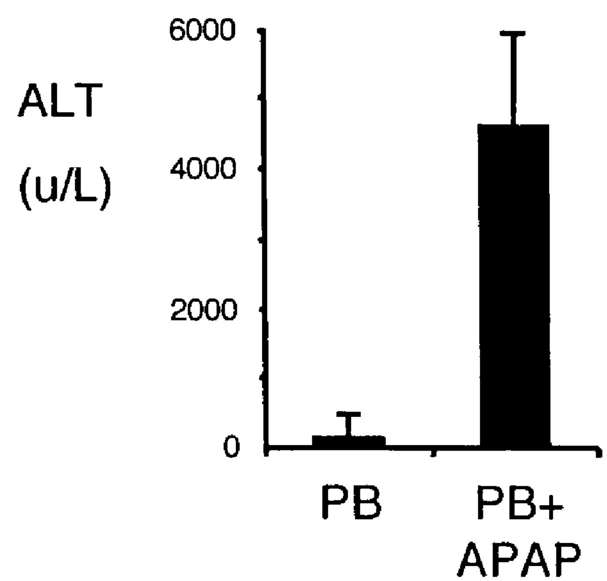

FIG. 13 illustrates the sensitivity of CAR humanized mice to APAP. CAR humanized mice (n=3) were pretreated with phenobarbital (PB) or vehicle alone for three days and administered a 250 mg/kg dose of APAP by intraperitoneal injection. Serum was collected and alanine aminotransferase (ALT) levels were measured after 24 hours.

Figure 14A:
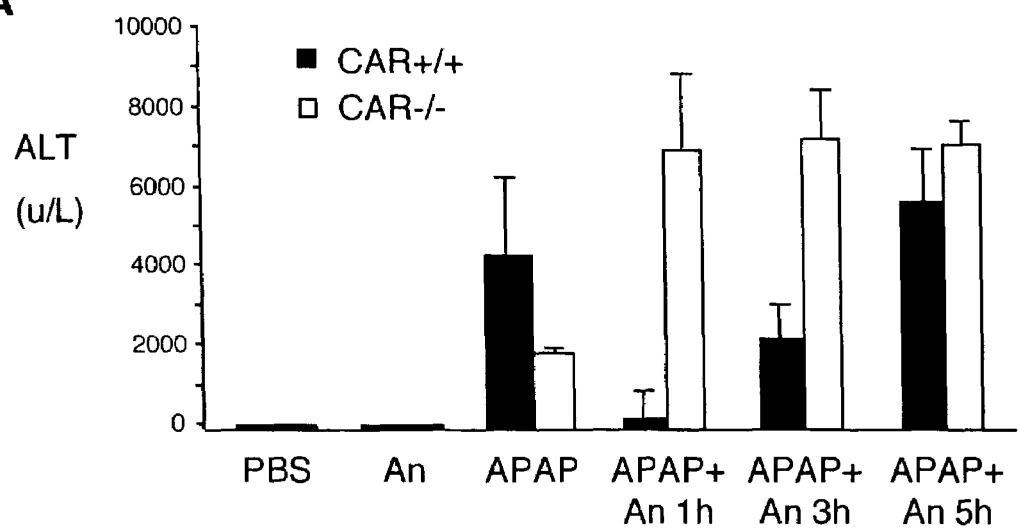
Figure 14B:
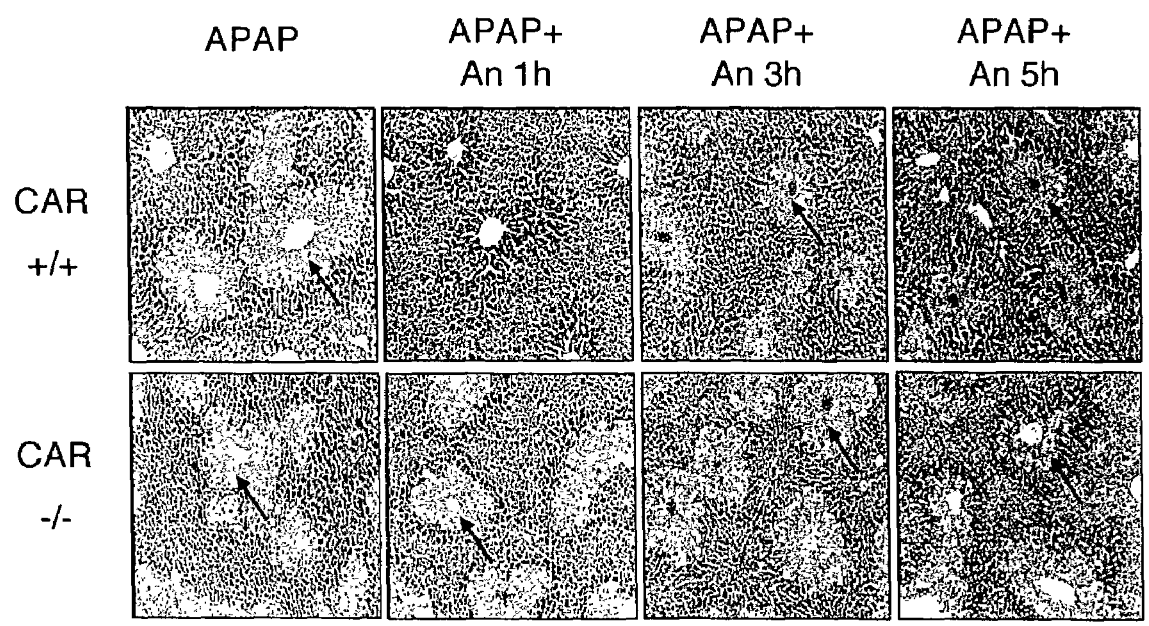

FIGS. 14A and 14B illustrate the hepatoprotection by androstanol treatment. CAR (+/+) or CAR (–/–) animals were given a 500 mg/kg dose of APAP by intraperitoneal injection, either with or without an additional injection of androstanol (An, 100 mg/kg) 1, 3, or 5 hours later (FIG. 14A). Serum alanine aminotransferase (ALT) levels were measured 24 hours later (n=5–7). At one and three hours, CAR (+/+) animals showed significantly lower ALT levels than CAR (–/–) animals (both $p<0.0001$). Liver sections from the same animals 24 hours after different treatments as indicated were stained with hematoxylin and eosin (FIG. 14B). Arrows indicate areas of hepatic necrosis.

Figure 15A:
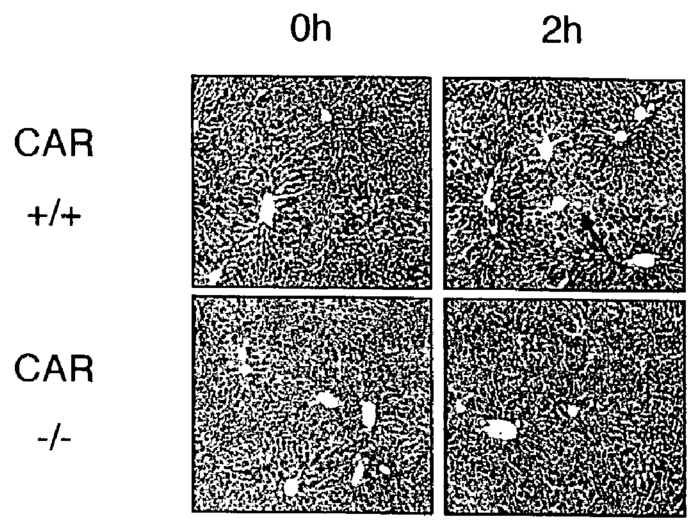
Figure 15B:
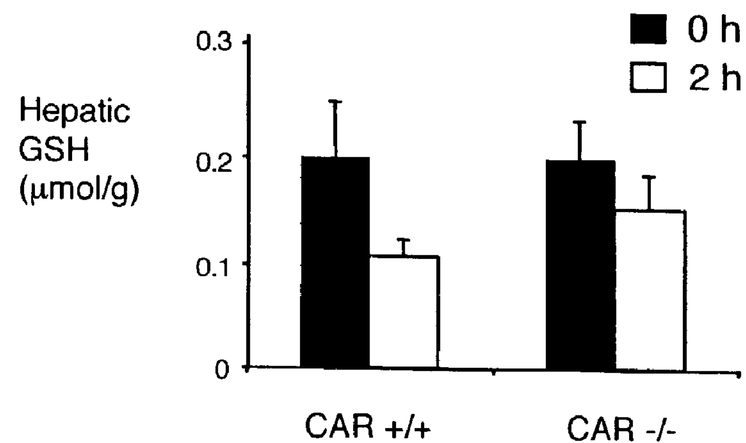

FIG. 15A is a picture of the histological staining of liver sections after two hours of 500 mg/kg APAP treatment. Liver sections from animals injected with 500 mg/kg APAP for 0 or 2 hours were stained with hematoxylin and eosin. Arrows indicate initial stages of necrosis surrounding central veins. The same liver samples were collected and GSH levels were measured at 0 and 2 hours as indicated. FIG. 15B is a graph of these GSH levels. CAR (–/–) animals were resistant to GSH depletion compared to CAR (+/+) animals ($p=0.032$).

Figure 16:
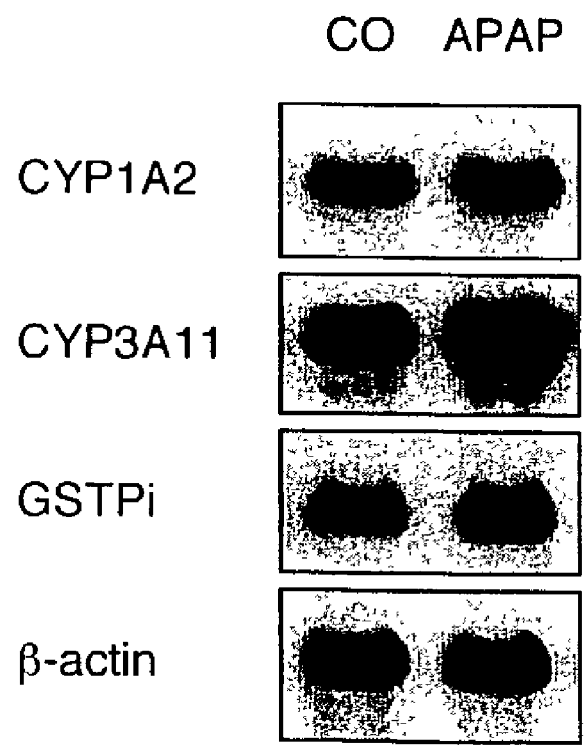

FIG. 16 is a picture of a Northern blot indicating induction of genes by APAP. CAR humanized mice (n=3) were treated with 500 mg/kg APAP or vehicle. After two hours, total liver RNA was prepared and subjected to Northern blot analysis with indicated probes. Quantitation of mRNA levels by densitometry indicated that the induction of CYP1A2, CYP3A11, and GSTPi was 1.8, 2.4 and 1.8 fold, respectively.

Figure 17:
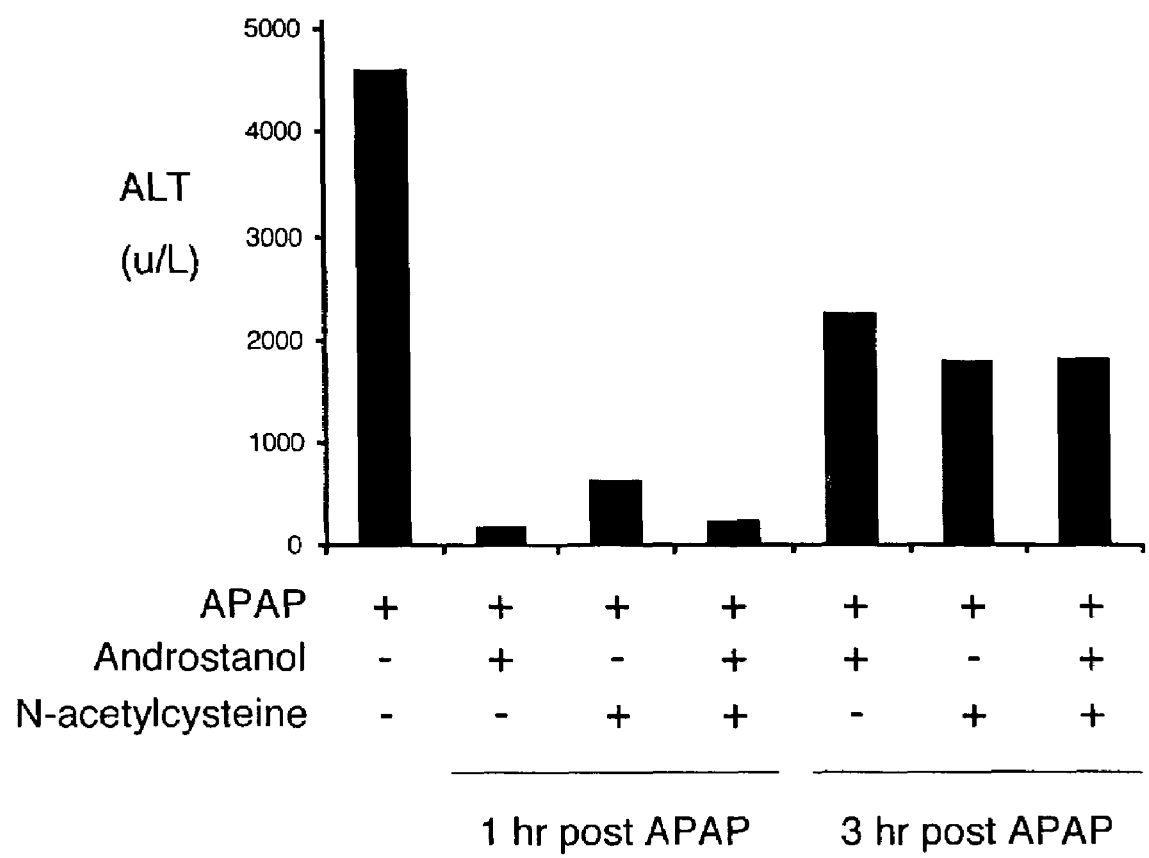

FIG. 17 is a bar graph comparing the hepatoprotective effects of androstanol and N-acetylcysteine. Wild-type mice (n=3 per group) were administered a 500 mg/kg dose of APAP by intraperitoneal injection. One to three hours later, as indicated, androstanol (100 mg/kg) or N-acetylcysteine (1 g/kg) were given by intraperitoneal injection. Serum samples from each group were pooled, and ALT levels were measured 24 hours after APAP administration.

FIG. 18 is the nucleic acid sequence (SEQ ID NO: 25) and deduced amino acid sequence (SEQ ID NO: 2) of a human CAR receptor (WO 99/15,555). Preferably, the DNA binding domain of human CAR includes amino acids 11–75 or a DNA binding fragment thereof. Preferably, the gene activation and/or ligand binding domain of human CAR includes amino acids 76–348 or a gene activating and/or ligand binding fragment thereof (WO 93/17,041). In preferred embodiments, a humanized CAR mouse expresses a human CAR protein that includes or that consists of a DNA binding domain, gene activation domain, and/or ligand binding domain, or fragment thereof.

FIG. 19 is the nucleic acid (SEQ ID NO: 26) and deduced amino acid sequence (SEQ ID NO: 1) of a murine CAR receptor, mCAR1 (WO 99/15,555). Preferably, the DNA binding domain of murine CAR includes amino acids 21–86 or a DNA binding fragment thereof. Preferably, the gene activation and/or ligand binding domain of human CAR includes amino acids 182–358 or a gene activating and/or ligand binding fragment thereof.

FIG. 20A is a schematic representation of the sequences of mCAR1, mCAR2, and human CAR. The sequence of mCAR1 (SEQ ID NO: 1) is shown, and differences between mCAR1 and human CAR and also the mCAR2 variant (SEQ ID NO: 27, GenBank accession number AAC53350) are indicated. The DNA binding domain is in bold. Dots indicate residues not present in human CAR. The positions of the introns in the mCAR gene are indicated. The first intron is 5 nucleotides upstream of the ATG encoding the first methionine. Introns that fall within a codon are indicated after the corresponding amino acid (WO 99/15,555).

FIG. 20B is a schematic representation indicating comparisons of mCAR1 to related members of the nuclear hormone receptor superfamily. The DNA binding, hinge, and ligand binding/dimerization domains of mCAR1 are indicated, and the percent identity of the analogous domains of related proteins is indicated. VDR is the human vitamin D receptor, xONR is a *Xenopus laevis* orphan receptor (Smith et al., *Nucl. Acids Res.* 22:66–71, 1994), and EcR is the *Drosophila melanogaster* ecdysone receptor (WO 99/15,555).

Figure 21:
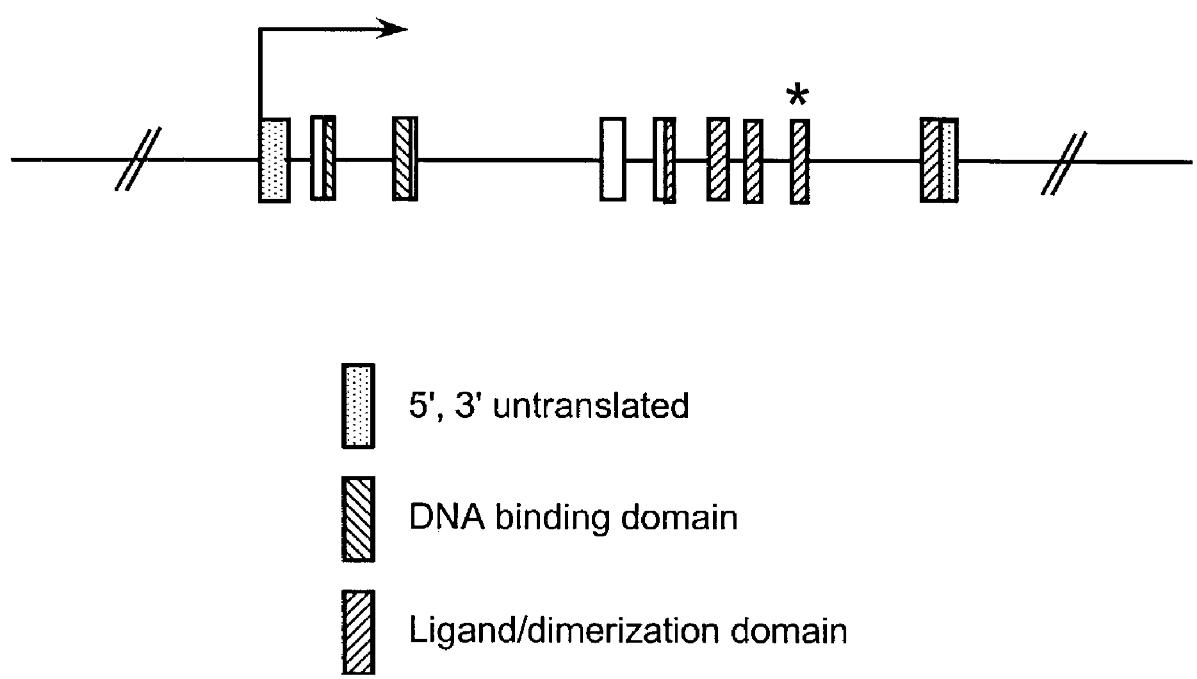

FIG. 21 is a diagram indicating the positions of the mCAR introns, 5' untranslated and 3' untranslated regions of the primary transcript, and the positions of various portions of the transcript and protein. For the 3' extended transcripts, the 3' untranslated region extends into the 3' flanking region. The 8th exon deleted in mCAR2 is indicated by a star (WO 99/15,555).

DETAILED DESCRIPTION OF THE INVENTION

The present invention is directed to compositions and methods relating to the function of the nuclear hormone receptor, CAR, particularly in human biological processes involving xenobiotic metabolism. Accordingly, the present invention provides transgenic animals comprising a mutation in a CAR receptor. Particularly, the present invention provides transgenic animals deficient of or lacking in the CAR gene, and comprising a reduction or absence of CAR receptor activity. The present invention also provides transgenic animals expressing a human CAR receptor. The transgenic animals of the present invention may be used, for example, in methods for identifying CAR ligands, including compounds that induce the activation of CAR target genes, and measuring the toxicity and half-life of such compounds. The present invention also provides methods which allow for the identification of compounds that activate CAR receptors and are potentially toxic to mammals (e.g., humans), as well as compounds that inhibit CAR receptors and reduce the toxicity or CYP-mediated metabolism of a pharmaceutically active compound (e.g., acetaminophen) administered to a mammal.

CAR Receptor Knockout Animals

The present invention provides transgenic animals which are deficient of or lacking in a CAR gene ("CAR knockout"). The transgenic animals of the present invention include transgenic animals that are heterozygous (+/–) and homozygous (–/–) for a mutation in the CAR gene. In one aspect, the transgenic animals of the present invention comprise a reduction or absence of native or naturally-occurring CAR receptor activity. In a preferred aspect, the transgenic animals of the present invention are mice.

Various methods known in the art may be used to produce CAR knockout mice of the present invention. For example, an appropriate targeting vector may be produced using standard methods known in the art (see, e.g., Sambrook, et al., 1989, *Molecular Cloning: A Laboratory Manual*, Second Edition, Cold Spring Harbor Laboratory Press, Cold Spring Harbor, N.Y.; E. N. Glover (eds.), 1985, *DNA Cloning: A Practical Approach*, Volumes I and II; M. J. Gait (ed.), 1984, *Oligonucleotide Synthesis*; B. D. Hames & S. J. Higgins (eds.), 1985, Nucleic Acid Hybridization; B. D. Hames & S. J. Higgins (eds.), 1984, *Transcription and Translation*; R. I. Freshney (ed.), 1986, Animal Cell Culture; Immobilized Cells and Enzymes, IRL Press, 1986; B. Perbal, 1984, A Practical Guide To Molecular Cloning; F. M. Ausubel et al., 1994, *Current Protocols in Molecular Biology*, John Wiley & Sons, Inc.). For example, the targeting vector may be prepared in accordance with conventional ways, where sequences may be synthesized, isolated from natural sources, manipulated, cloned, ligated, subjected to in vitro mutagenesis, primer repair, or the like. At various stages, the joined sequences may be cloned, and analyzed by restriction analysis, sequencing, or the like.

Once an appropriate targeting vector has been prepared, the targeting vector may be introduced into an appropriate host cell using any method known in the art. Various techniques may be employed in the present invention, including, for example: pronuclear microinjection; retrovirus mediated gene transfer into germ lines; gene targeting in embryonic stem cells; electroporation of embryos; sperm-mediated gene transfer; and calcium phosphate/DNA co-precipitates, microinjection of DNA into the nucleus, bacterial protoplast fusion with intact cells, transfection, polycations, e.g., polybrene, polyornithine, or the like (see, e.g., U.S. Pat. No. 4,873,191; Van der Putten, et al., 1985, *Proc. Natl. Acad. Sci., USA* 82:6148–6152; Thompson, et al., 1989, *Cell* 56:313–321; Lo, 1983, *Mol Cell. Biol.* 3:1803–1814; Lavitrano, et al., 1989, *Cell*, 57:717–723). Various techniques for transforming mammalian cells are known in the art (see, e.g., Gordon, 1989, *Intl. Rev. Cytol.*, 115:171–229; Keown et al., 1989, *Methods in Enzymology*; Keown et al., 1990, *Methods and Enzymology*, Vol. 185, pp. 527–537; Mansour et al., 1988, *Nature*, 336:348–352).

Successful insertion of the targeting vector by homologous recombination is typically detected by identifying cells for expression of the marker gene. In a preferred embodiment, the cells transformed with the targeting vector are subjected to treatment with an appropriate agent that selects against cells not expressing the selectable marker. Only those cells expressing the selectable marker gene survive and/or grow under certain conditions. For example, cells that express the introduced neomycin resistance gene are resistant to the compound G418, while cells that do not express the neo gene marker are killed by G418.

Selected cells are then injected into a blastocyst (or other stage of development suitable for the purposes of creating a viable animal, such as, for example, a morula) of an animal (e.g., a mouse) to form chimeras (see, e.g., Bradley, A. in *Teratocarcinomas and Embryonic Stem Cells: A Practical Approach*, E. J. Robertson, ed., IRL, Oxford, pp. 113–152 (1987)). Alternatively, selected ES cells can be allowed to aggregate with dissociated mouse embryo cells to form the aggregation chimera. A chimeric embryo can then be implanted into a suitable pseudopregnant female foster animal and the embryo brought to term. Chimeric progeny can be used to breed animals to generate heterozygous mice. Heterozygous mice can then be mated to produce homozygous mice.

Characterization and Analysis of CAR Receptor Knockout Mice

In a preferred embodiment, CAR knockout mice of the present invention exhibit a decrease or absence of induction, expression or activity of a CAR target gene in response to a xenobiotic inducer. In a particular embodiment, CAR knockout mice of the present invention exhibit a decrease or absence of CYP enzyme induction, activity, or expression in response to a xenobiotic inducer, including PB and TCPOBOP.

More specifically, CAR knockout mice exhibited an absence in the expression of CYP2B10 in response to either PB or TCPOBOP. The robust induction of expression of CYP2B10 mRNA in response to either PB or TCPOBOP was detected in wild-type male or female mice but was absent in knockout animals (FIG. 2A). Similar results were obtained with two independent CAR knockout mouse lines. This requirement for CAR was also demonstrated in the small intestine, using in situ hybridization. As indicated in FIG. 2B, either PB or TCPOBOP also induced CYP2B10 expression in the small intestine in wild-type mice, but was not detected in CAR knockout mice. Similar to the induction of CYP2B10, substantial induction of murine CYP3A11 mRNA in response to PB or TCPOBOP was observed in wild-type mice (FIG. 5A). In contrast, a negligible level of induction of CYP311 was detected in CAR −/− mice (FIG. 5B).

In another embodiment, CAR knockout mice of the present invention exhibit an absence of increased liver mass or no enlargement of the liver upon treatment with an xenobiotic inducer, including PB or TCPOBOP. More specifically, hyperplasia or hypertrophy in the liver in response to treatment with either phenobarbital or the more potent inducer TCPOBOP were not detected in the CAR knockout mice.

Acute treatments with PB-like inducers, particularly TCPOBOP, cause an up to 2-fold increase in liver mass relative to total body mass (See, e.g., Heubel et al., *Biochem. Pharmacol.* 38:1293–1300, 1989). This hepatomegaly is thought to be a reflection of both cellular hypertrophy and mitogenesis. After three days of treatment with either PB or TCPOBOP, an increase in liver mass was observed in wild-type mice. Whereas, CAR −/− mice subjected to the same PB or TCPOBOP treatments did not show any evidence of increased liver mass as observed in the wild-type mice (FIG. 3A).

In a further embodiment, CAR knockout mice of the present invention exhibit an absence of xenobiotic induction of DNA synthesis when treated with 5-bromodeoxyuridine (BrdU). As demonstrated in FIG. 3B, xenobiotic induction of DNA synthesis revealed by increased incorporation of BrdU in the wild-type animals was completely absent in the CAR −/− animals.

In yet a further embodiment, CAR knockout mice of the present invention exhibit decreased metabolism of the CYP substrate zoxazolamine. Many studies have demonstrated that increased CYP enzyme activity results in increased metabolic inactivation of this muscle relaxant, which is reflected in decreased duration of zoxazolamine-induced paralysis. As demonstrated in Tables 1 and 2, pretreatment of wild-type animals with either PB or TCPOBOP significantly decreased the duration of paralysis. The duration of paralysis was substantially longer in untreated CAR −/− mice than in wild-type mice, the paralysis was not affected by pretreatment with either PB or TCPOBOP. For example, wild-type control female mice were paralyzed more than 12 hours, while wild-type xenobiotic-pretreated female mice were not paralyzed. Among the CAR −/− females, two animals from each group of control, PB-treated, or TCPOBOP-treated animals died; the survivors were paralyzed for more than 12 hours.

TABLE 1

Increased duration of zoxazolamine-induced paralysis in male CAR (−/−) mice due to decreased metabolism of zoxazolamine

| | CAR (+/+) | CAR (−/−) |
|---|---|---|
| Control | 2 hours | >5 hours |
| PB-treated | <20 minutes | >5 hours |
| TCPOBOP-treated | <20 minutes | >5 hours |

TABLE 2

Increased duration of zoxazolamine-induced paralysis in female CAR (−/−) mice due to decreased metabolism of zoxazolamine

| | CAR (+/+) | CAR (−/−) |
|---|---|---|
| Control | >12 hours | died |
| PB-treated | not paralyzed | died |
| TCPOBOP-treated | not paralyzed | died |

In these experiments, mice were pretreated for three days with PB or TCPOBOP, after which time they were given a single intraperitoneal injection of zoxazolamine (300 mg/kg). Paralysis time was recorded as the time when the mice were able to right themselves repeatedly.

In another embodiment, CAR knockout mice of the present invention are absent of liver damage when treated with cocaine in the presence of a xenobiotic inducer, such as PB or TCPOBOP. Preferably, CAR knockout mice of the present invention pretreated with PB or TCPOBOP do not exhibit acute hepatotoxicity or cocaine-mediated hepatotoxicity when injected with cocaine. For example, treatment with PB-like inducers, such as PB or TCPOBOP also sensitizes animals to hepatotoxic effects of a number of compounds, including cocaine. As shown in FIG. 4, treatment with either PB or TCPOBOP resulted in a significant increase in serum levels of the liver enzyme alanine aminotransferase (ALT) as an acute response to cocaine administration. Evidence of liver damage was not observed in CAR −/− animals.

In a further embodiment, CAR knockout mice exhibit a resistance to acetaminophen toxicity. As described below, inhibition of CAR activity by administration of the inverse agonist ligand androstanol one hour after acetaminophen treatment blocked hepatotoxicity in wild-type mice, but not in CAR null mice.

Functional Role of CAR Receptor

The present invention demonstrates that CAR is essential for response to PB-like inducers of xenobiotic metabolism, and thus CAR functions as a xenobiotic receptor in vivo to mediate the response to PB-like inducers. CAR can therefore be added to the previously described peroxisome proliferator activated receptor a and the aryl hydrocarbon receptor as a primary determinant of the response of phase I metabolic enzymes to foreign compounds. CAR is joined in this by its closest relative within the receptor superfamily, PXR/SXR, which has recently been shown to mediate response to a distinct group of xenobiotics (See, e.g., Jones et al., *Mol. Endocrinol.* 14:27–39, 2000; Kliwer et al., *Cell* 92:73–82, 1998; Blumberg et al., *Genes Dev.* 12:3195–3205). Although both DNA binding specificity and xenobiotic responses of CAR and PXR/SXR have been reported to overlap to some extent, no evidence for any compensatory effect of the latter was observed in the CAR knockout animals. Thus, it is now apparent that specific xenobiotics can induce specific metabolic responses by activating distinct receptors.

This mechanism may account for a large number of clinically significant drug-drug interactions in which the presence of one compound, such as phenobarbital, results in increased metabolism of another drug or foreign compound. Differences in the levels of activation of xenobiotic receptors among individuals based on differences in exposure to specific xenobiotics may also explain the significant inter-individual variability of the levels of particular cytochromes. Consistent with the very low basal levels of mouse CYP2B10, most humans have low or undetectable levels of CYP2B6, a human target of CAR activation. However, this enzyme is present at up to 100-fold higher levels in a subset of individuals. The results described here suggest that this variability could be the basis for the relatively rare, but clinically significant hepatotoxicity observed in a subset of individuals exposed to high levels of cocaine. More generally, variations in CAR activity in response to the wide range of PB-like inducers may have significant impact on the metabolism of a wide range of pharmacologic agents and other foreign compounds. The CAR mice described herein facilitate the identification of compounds able to activate CAR in vivo, as well as enable the identification of additional, specific downstream target genes that mediate its effects.

CAR Target Genes

Various CAR target genes are known in the art and may be applicable to the compositions and methods of the present invention. The CAR target genes include, but are not limited to cytochrome P450 genes, particularly, cytochrome P450 genes and other enzymes involved in xenobiotic metabolism (see, e.g., Waxman, *Archives of Biochemistry and Biophysics* 369, 1, 1999; Kliewer et al., *Science* 284, 757–760, 1999). Preferred CAR target genes include murine CYP2B10 (SEQ ID NO: 11, GenBank Accession No. NM_009998) and human CYP2B6 (SEQ ID NO: 12, GenBank Accession No. AC023172). Additional preferred CAR target genes include murine CYP3A11 (SEQ ID NO:13, Accession No. NM_07818) and human CYP3A4 (SEQ ID NO:14, GenBank Accession No. NM _017460).

CAR target genes may also include a CAR responsive promoter operably-linked to a reporter gene, such as human growth hormone, secreted alkaline phosphatase, chloramphenicol acetyl transferase, luciferase, green fluorescent protein, CYP2B6, or any other reporter gene (see, for example, Ausubel et al., Current Protocols in Molecular Biology, Chapter 9, John Wiley & Sons, New York, 2000). Examples of appropriate promoters include native CYP promoters, such as the CYP2B10 promoter (GenBank Accession No. U48732; Honkakoski et al., J. Biol. Chem. 271, 9746–9753, 1996) containing the previously described phenobarbital response element (Honkakoski et al., Mol. Cell. Biol. 18:5652–5658, 1998), the CYP2B6 promoter (GenBank Accession No. AC023172), the CYP3A11 promoter (Toide et al., Arch. Biochem. Biophys. 338(1):43–49, 1997), the CYP3A4 promoter (Accession No. AF185589), or synthetic promoter constructs in which DNA binding sites for CAR/RXR heterodimers are operably-linked to functional basal promoters (Tzameli et al., Mol. Cell. Biol. 20: 2951–2958, 2000).

The determination or measurement of the induction of CAR target genes by CAR may be accomplished using standard methods known in the art. More particularly, the level of induction of the CAR target gene or transgene may be determined using standard assays for measuring the level of encoded mRNA or protein (see for example, Ausubel et al., Current Protocols in Molecular Biology, John Wiley & Sons, New York, 2000). Alternatively, an enzymatic activity of a CAR target gene, such as the 7-pentoxyresorufin O-dealkylase activity of the CYP2B10 CAR target gene, may be measured (Pellinen et al. Hepatology 23:515–23, 1996). Examples of CAR target genes include CYP2B10, a CYP2B6, CYP3A11, and CYP3A4; examples of CAR responsive promoters include the CYP2B10, CYP2B6, CYP3A11, and CYP3A4 promoters and promoters operably-linked to DNA binding sites for CAR/RXR heterodimers. Alternatively, an increase in CAR receptor activity can be assayed by determining an increase in liver mass relative to total body mass, an increase in release of a liver enzyme such as alanine aminotransferase into the serum, or an increase in DNA synthesis in the liver, using the assays described herein. CAR-mediated induction may be measured in response to a number of xenobiotic compounds, including TCPOBOP.

Transgenic Mice Expressing Human CAR Receptor

A humanized CAR mouse expressing the human CAR receptor may be generated by any of several standard methods (see, for example, Ausubel et al. (Chapter 9), supra). Preferably, the humanized CAR mouse lacks murine CAR. For example, a conventional transgenic animal expressing the human CAR gene from a promoter active in appropriate tissues, such as the liver or the intestine, may be generated. Also contemplated by the present invention is a humanized CAR mouse which expresses a region or portion of the humanized CAR receptor that is sufficient for binding of a ligand, including the human CAR ligand binding domain or a portion thereof (see, e.g., PCT Publication No. WO 0171361).

Various promoters known in the art may be used for directing expression of the human CAR receptor. Examples of such promoters for expression of transgenes include, but are not limited to the zinc-inducible metallothionein promoter, the DEX-inducible tyrosine aminotransferase (TAT) promoter, the rifampicin inducible CYP3A4 promoter, the albumin promoter (Xie et al., Nature 406:435–439, 2000), the fatty acid binding protein (FABP), transthyretin (TTR) (Ye et al., Mol Cell Biol. 19:8570–8580, 1999), or CAR promoter. The FABP promoter is expressed in the liver and small intestine. The TTR promoter is also well described and widely used promoter to achieve liver-specific expression of transgenes. Other regulatory sequences may be used to enhance expression of the human CAR receptor in a humanized CAR mouse.

The human CAR transgene may then be introduced into a homozygous CAR −/− mouse by conventional breeding (Pierson et al., *Mol. Endocrinol.* 14:1075–1085, 2000; Slee et al., *Proc Natl Acad Sci U S A.* 96:8040–8045, 1999). In another possible method, the human CAR transgene may be injected into fertilized oocytes from homozygous CAR −/− mice, directly generating the desired transgenic mice. In a third method, embryonic stem cells may be generated from a homozygous CAR −/− animal (Ausubel et al. (Chapter 9), supra). Conventional homologous recombination techniques may then be used to replace the inactivated murine CAR gene with a functional human CAR receptor gene (Fiering et al., Methods Enzymol. 306:42–66, 1999). Since the CAR −/− animals contain the neo gene which confers resistance to G418, another appropriate gene such as hygromycin may be used in the human CAR replacement construct to allow the selection of cells in which the human CAR gene has replaced the inactivated murine CAR gene. In still another possible method, a functional human CAR receptor gene may be introduced into a homozygous CAR −/− mouse using gene therapy and a promoter active in appropriate tissues, such as the promoters described above, and contained in an adenoviral, adeno-associated viral, retroviral, lentiviral, herpes viral, nonviral, or any other suitable vector (see, for example, Sarkar et al., *Hum Gene Ther.* 11:881–894, 2000; Goddard et al., *Gene Ther.* 4:1231–1236, 1997).

If desired, mice expressing human CAR, but lacking mouse CAR can be generated by mating humanized CAR mice with the CAR −/− mice described above. Alternatively, ES cells or embryos from humanized CAR mice can be genetically modified as described above to disrupt the endogenous mouse CAR gene.

It is known that the ligand binding domains of human and mouse CAR genes differ somewhat in amino acid sequence, and that these two proteins respond differently to some activators. In particular, TCPOBOP is an agonist ligand for the murine CAR receptor, but not the human CAR receptor (Tzameli et al., supra). Similarly, clotrimazole is an inverse agonist for the human, but not the murine, CAR receptor (Moore et al., supra). As a result, CAR −/− knockout mice expressing a functional human CAR receptor also provide useful models for drug screening since their response to drugs or other xenobiotic compounds should be based on the human rather than the murine CAR receptor. Such "humanized" CAR mice allow for the identification of CAR ligands, including compounds, such as those in clinical development, with potentially undesirable effects in humans.

In one aspect, transgenic mice of the present invention expressing human CAR express only human CAR in the liver. In a particular embodiment, transgenic mice expressing human CAR exhibit an induction of a xenobiotic response, particularly, an induction of a CAR target gene, such as CYP2B10 mRNA in response to PB. In another particular embodiment, the transgenic mice expressing human CAR do not demonstrate or exhibit an induction of an xenobiotic response, such as activation of a CAR target gene in response to TCPOBOP.

Human CAR-Mediated Toxicity

As described in the examples below, CAR was determined to function as a key regulator of acetaminophen metabolism and hepatotoxicity. Both known CAR activators and high doses of acetaminophen induced expression of three acetaminophen metabolizing enzymes in wild-type, but not CAR null mice. Additionally, CAR null mice were resistant to acetaminophen toxicity. Inhibition of CAR activity by administration of the inverse agonist ligand androstanol one hour after acetaminophen treatment blocked hepatotoxicity in wild-type, but not CAR null mice. These results demonstrate that inhibitors of CAR receptor expression and/or activity are useful for the treatment of any adverse-side effects associated with acetaminophen or other hepatotoxic agents in mammals (e.g., humans).

In particular, overdoses of acetaminophen (APAP, also known as 4'-hydroxyacetanilide, N-acetyl-p-aminophenol and paracetamol) are the leading cause of hospital admission for acute liver failure in the United States. Ingestion of amounts of APAP only 2–3 fold above the maximum daily recommended dose can cause hepatotoxicity and higher doses result in centrilobular necrosis that is potentially fatal. The basis for this toxicity has been well studied. Particularly at high doses, cytochrome P450 enzymes, especially CYP1A2, CYP2E1, and isoforms of CYP3A, convert APAP to a reactive quinone form, N-acetyl-p-benzoquinone imine (NAPQI) that covalently binds to cellular macromolecules and also causes production of reactive oxygen species. At subtoxic doses, NAPQI is inactivated by glutathione S transferases (GSTs) via conjugation with reduced glutathione (GSH), but NAPQI accumulates when GSH levels are depleted. Among the numerous GST enzymes, the GSTPi isoforms are particularly effective at NAPQI inactivation. Their importance in APAP toxicity was confirmed by the unexpected demonstration that knockout mice lacking both GSTPi isoforms are relatively resistant to APAP hepatotoxicity due to a decreased rate of GSH depletion (Henderson et al., *Proc Natl Acad Sci U S A* 97:12741–12745, 2000).

APAP toxicity is increased in both humans and rodents by pretreatment with various inducers of CYP gene expression including ethanol, an inducer of CYP2E and 3A isoforms (Kostrubsky et al., *Toxicol Appl Pharmacol* 143:315–323, 1997 and Sinclair et al., Biochem Pharmacol 55:1557–1565, 1998) and PB, a well known inducer of CYP2B, 3A and other isoforms (Pirotte, Ann Intern Med 101:403, 1984 and Burk et al., Res Commun Chem Pathol Pharmacol 69:115–158, 1990).

Assays for CAR Receptor Activity

The homozygous CAR −/− animals described herein are useful for drug metabolism assays since these animals allow for the identification of CAR ligands and drugs or other xenobiotic compounds that induce expression of CYP2B10, CYP3A11, or other CAR target genes in wild-type, but not CAR −/− animals. The detection of CYP2B10 or CYP3A11 induction may be performed by any of several assays, including assays of CYP2B10 or CYP3A11 protein levels (for example, by Western blot analysis), mRNA levels (for example, by Northern blot analysis), or enzymatic activity (for example, my measuring 7-pentoxyresorufin O-dealkylase enzymatic activity as described, for example, in Pellinen et al. (Hepatology 23:515–23, 1996)). Alternatively, an increase in liver mass relative to total body mass or an increase in DNA synthesis in the liver may be measured as described herein. Similar assays for other CAR target genes may also be used.

Moreover, as alternatives to assays involving endogenous murine CAR target genes, assays may be conducted to measure appropriate reporter transgenes inserted by any standard technique (for example, those techniques described above) into wild-type mice, CAR −/− mice, humanized CAR mice, mice lacking the gene encoding the receptor related to CAR (known as SXR, PXR or by other names (Kliewer et. al., Cell 92:73–82, 1998; Blumberg et al., Genes Dev. 12:3195–3205, 1998)), or any other appropriate strain. These reporter transgenes consist of a CAR responsive promoter operably-linked to an easily measured reporter gene. Examples of appropriate promoters include native CYP promoters such as the CYP2B10 promoter containing the previously described phenobarbital response element (Honkakoski et al., supra), the CYP2B6 promoter, the CYP3A11 promoter, the CYP3A4 promoter, or synthetic promoter constructs in which DNA binding sites for CAR/RXR heterodimers are linked to functional basal promoters (Tzameli, et al., supra). Examples of appropriate reporter genes include, without limitation, human growth hormone, secreted alkaline phosphatase, luciferase, green fluorescent protein, chloramphenicol acetyl transferase, CYP2B6, CYP3A11. and any other reporter gene (see, for example, Ausubel et al. (Chapter 9), supra). The assays for CAR target genes involve standard procedures (see, for example, Ausubel et al. (Chapter 9), supra) and may be based on appropriate samples from the mice, such as liver or serum samples. Alternatively, hepatocytes or other appropriate cell types may be harvested from the animals and propagated. Compounds may be administered to these cells to determine whether the compounds effect a change in expression of CAR target genes or reporter transgenes.

Candidate compounds may also be tested for their ability to activate or inhibit human CAR in cell based assays using cells that have been transiently or stably transfected with a transgenic construct encoding human CAR. For example, the Alb-hCAR transgenic construct illustrated in FIG. 6 which encodes human CAR under the control of the albumin promoter was used to transiently transfect a human hepatoma derived HepG2 cell line. The HepG2 cell lines contains a plasmid with a previously described reporter construct, denoted betaRAREluciferase, which contains a luciferase reporter gene under the control of a CAR responsive promoter (Forman et al., Nature 395(6702):612–5, 1998). As illustrated in FIG. 9, transfection of the cells with the Alb-hCAR transgene construct resulted in a 5.2-fold greater level of luciferase reporter gene expression than transfection of the cells with the corresponding control construct which lacks the human CAR coding sequence. This result indicates that this transgenic construct encodes functional human CAR which can activate the expression of a reporter gene operably liked to a CAR responsive promoter. The cells transfected with the Alb-hCAR construct can be used to identify candidate compounds that increase the expression of the luciferase reporter gene as activators of human CAR and to identify candidate compounds that decrease the expression of the luciferase reporter gene as inhibitors of human CAR.

Therapeutic Methods and Routes of Administration

The invention also features methods for preventing, stabilizing, or treating toxicity associated with CAR-mediated metabolism of a xenobiotic by administering an inhibitor of CAR receptor expression and/or activity to a mammal (e.g., a human). Accordingly, in one such aspect, the invention features a method for preventing, stabilizing, or treating an adverse effect or symptom associated with one or more hepatotoxic agents (e.g., acetaminophen and/or phenobarbital) in a mammal (e.g., a human) by administering to a mammal (for example, a human) one or more compounds that inhibit the expression and/or activity of a CAR receptor in the mammal. Preferably, the compound decreases the number of liver cells that are killed by the hepatotoxic agent by at least 20, 30, 40, 50, 60, 70, 80, 90, 95, or 100% compared to a vehicle control. In preferred embodiments, compound decreases the serum alanine aminotransferase activity of a mammal treated with the hepatotoxic agent by at least 20, 30, 40, 50, 60, 70, 80, 90, 95, or 100% compared to a vehicle control. In some embodiments, the level of reduced glutathione decreases by less than 20, 30, 40, 50, 60, 70, 80, 90, or 95% in a mammal treated with both the compound and the hepatotoxic agent. Preferably, the compound decreases the expression or an activity of CAR (e.g., the induction of a CAR target gene) by at least 20, 30, 40, 50, 60, 70, 80, 90, 95, or 100% compared to the corresponding expression or activity of CAR in the presence of the hepatotoxic agent, but in the absence of the compound. Exemplary hepatotoxic agents include compounds whose metabolism is induced by human CAR.

With respect to the therapeutic methods of the invention, it is not intended that the administration of compounds to a mammal be limited to a particular mode of administration, dosage, or frequency of dosing; the present invention contemplates all modes of administration, including oral, intraperitoneal, intramuscular, intravenous, intraarticular, intralesional, subcutaneous, or any other route sufficient to provide a dose adequate to prevent or treat an infection. One or more compounds may be administered to the mammal in a single dose or multiple doses. When multiple doses are administered, the doses may be separated from one another by, for example, one week, one month, one year, or ten years. It is to be understood that, for any particular subject, specific dosage regimes should be adjusted over time according to the individual need and the professional judgment of the person administering or supervising the administration of the compositions. If desired, conventional treatments (e.g., treatments that reduce liver toxicity such as N-acetylcysteine) can be used in combination with the compounds of the present invention.

Suitable carriers include, but are not limited to, saline, buffered saline, dextrose, water, glycerol, ethanol, and combinations thereof. The composition can be adapted for the mode of administration and can be in the form of, for example, a pill, tablet, capsule, spray, powder, or liquid. In some embodiments, the pharmaceutical composition contains one or more pharmaceutically acceptable additives suitable for the selected route and mode of administration. These compositions may be administered by, without limitation, any parenteral route including intravenous, intraarterial, intramuscular, subcutaneous, intradermal, intraperitoneal, intrathecal, as well as topically, orally, and by mucosal routes of delivery such as intranasal, inhalation, rectal, vaginal, buccal, and sublingual. In some embodiments, the pharmaceutical compositions of the invention are prepared for administration to the mammal in the form of liquids, including sterile, non-pyrogenic liquids for injection, emulsions, powders, aerosols, tablets, capsules, enteric coated tablets, or suppositories.

Exemplary mammals include humans, primates such as monkeys, animals of veterinary interest (e.g., cows, sheep, goats, buffalos, and horses), and domestic pets (e.g., dogs and cats).

The following examples are intended only to illustrate the present invention and should in no way be construed as limiting the subject invention.

EXAMPLES

Example 1

Targeting Vector Construction

To construct the targeting vector for the CAR locus, an XbaI-EagI fragment containing the nuclear localized β-galactosidase gene from vector pPD 46.21 was subcloned into the XbaI and EcoRI sites of the pGKneo plasmid. DNA from AB 1 ES cells was used to amplify CAR genomic fragments for both 5' and 3' arms. For the 5' arm, a 3 kb CAR promoter fragment was cloned into the ApaI and XbaI sites. For the 3' arm, a 5 kb fragment spanning exons 3 to 9 was cloned into the SalI and NotI sites. The primers for the 5' arm were 5'-gcgcgcgggccctggcatacattaacacaaacacatacatat-3' (SEQ ID NO.: 3) and 5'-gcgcgctctagaaggacccagactctggacccagggc-aaaga-3' (SEQ ID NO: 4). The primers for the 3' arm were 5'-gcgcgcgtcgacaggtgaagtgcttctccccaacagaaacaa-3' (SEQ ID NO: 5) and 5'-gcgcgcgcggccgctgtcctgggagcagcctctgcagc-cgct-3' (SEQ ID NO: 6).

Example 2

Generation of CAR Receptor Knockout Mice

ABI ES cells ($10^7$) were electroporated with 25 μg targeting construct in 0.9 ml PBS using a Bio-Rad Gene Pulser (500 μF, 230 V). The cells were then plated on one or two 10-cm plates containing a monolayer of irradiated STO feeder cells. About twenty-four hours later, the cells were subjected to G418 selection (350 μg/ml, Gibco) for 9 days. Resistant clones were analyzed by Southern blotting after HindIII digestion, using the 3' probe indicated in FIG. 1A (FIG. 1B). The primers for the 3' probe were 5'-ggacaacct-cagcccacagtgatgc-3' (SEQ ID NO: 7) and 5'-tcctttggttaccac-ctgactctgc-3' (SEQ ID NO: 8). Two positive clones were expanded and injected into C57BL/6 blastocysts. Male chimeras were back crossed to C57BL/6 female mice. Heterozygotes were determined by Southern blotting and intercrossed to generate homozygotes.

Example 3

Analysis of CAR and CAR Knockout Mice

To assess the functional role of CAR, two independent mouse lines were generated in which a promoter proximal segment of the CAR gene, including a portion of the DNA binding domain, was replaced by the coding region for β-galactosidase (FIG. 1A). These β-galactosidase "knockin" animals were unable to express CAR mRNA (FIG. 1C). This loss of CAR expression did not result in any overt phenotype; homozygous CAR −/− animals were born at expected Mendelian frequency, and both male and female CAR −/− animals were fertile.

Example 4

Animal Treatment

At least three mice between about 8–10 weeks old were used for each treatment. Mice were pretreated by intraperitoneal injection with corn oil, PB (100 mg/kg, Sigma), or TCBOPOP (3 mg/kg) for the indicated time. For a three day PB treatment, mice were injected intraperitoneally three times with PB, at one injection per day.

Example 5

Zoxazolamine Paralysis Test

Mice pretreated with corn oil, PB, or TCPOBOP were given a single intraperitoneal injection of zoxazolamine (300 mg/kg, Sigma) approximately 24 hours after the last dose of PB. Mice were placed on their backs, and the paralysis time was defined as the time required for the animal to regain sufficient consciousness to right itself repeatedly (Liang et al., Proc. Natl. Acad. Sci. U S A, 93:1671–6, 1996).

Example 6

Cocaine Treatment and Alanine Aminotransferase (ALT) Assay

Male mice pretreated with corn oil, PB, or TCPOBOP were injected intraperitoneally with cocaine HCl (30 mg/kg) 24 hours after the last dose of PB. The mice were anaesthetized 24 hours after cocaine treatment. Blood was drawn from the eye for determination of serum ALT activity.

Example 7

RNA Analysis

Approximately 20 μg of total RNA from individual mouse livers was subjected to Northern blot analysis (FIG. 1C). A mouse CAR cDNA probe was used to reveal the absence of CAR transcripts in the CAR null mice. Probes for CYP2B10 were prepared by RT-PCR with mouse liver total RNA using Superscript One-step RT-PCR System (Life Technologies). PCR primers were 5'-ccgcctctagaagtcaacattggttagac-3' (SEQ ID NO: 9) and 5'-ccgccggatcccacactaagcctcataat-3' (SEQ ID NO: 10). For in situ hybridization, small intestine tissue was cross sectioned at 7 μM thickness. Slides were subjected to in situ hybridization with a [$^{35}$S]-labeled CYP2B10 antisense probe. To prepare the probe, the CYP2B10 RT-PCR product was subcloned into the XbaI and BamHI sites of Bluescript7 SK(−) phagemid (Stratagene). The plasmid was linearized with Xba I. T7 RNA polymerase was used to synthesize [$^{35}$S]-labeled antisense probes.

Example 8

Hepatocyte Proliferation

To determine the proliferation of hepatocytes following PB or TCPOBOP treatment, mice pretreated with corn oil, PB, or TCPOBOP received a single intraperitoneal dose of BrdU/FdU (2 ml/100 g, Amersham). Mice were sacrificed approximately 2 hours after BrdU administration. BrdU incorporation was determined using a mouse anti-BrdU monoclonal antibody (DAKO Corporation) and Vectastain ABC Kit (Vector Laboratories Inc.) (FIG. 3B), using standard procedures.

Example 9

Human CAR Transgene Construct

To generate transgenic mice expressing a human CAR receptor, the transgene construct illustrated in FIG. 6 was used. The transgenic construct contained the coding sequence for a human CAR receptor operably linked to the liver specific, albumin promoter. Additionally, a region from an abundantly expressed gene, rabbit β-globin, was added between the promoter and the CAR receptor coding sequence to enhance the expression of the human CAR receptor. The polyadenylation (poly A) sequence from bovine growth hormone was also added downstream of the human CAR receptor coding sequence. The bovine growth hormone is a strong poly A sequence that ensures termination of transcription and stabilization of the mRNA transcripts. Furthermore, the use of a heterologous poly A sequence eliminates the requirement to isolate the genomic sequence which corresponds to the endogenous poly A sequence of human CAR.

The transgenic human CAR construct was generated from several previously described plasmids. To generate the starting vector, a BamHI-EcoRI 640 base pair fragment consisting of part of exon 2, intron 2, and exon 3 of the rabbit β-globin gene [nucleotides ~551–1190 from Entrez accession number V00878, from the previously described vector pKCR (Nikaido et al., *Nature* 311:631–635, 1984)] was inserted into the corresponding sites in the pBluescript plasmid (Stratagene) to generate vector KCR-KS. A 350 base-pair blunt-ended XbaI-XhoI fragment from the bovine growth hormone polyadenlyation signal ("bGHpA," containing nucleotides 1671–1867 of Entrez accession number AF335419) was removed from the PGKNeo plasmid (Mortensen et al., *Mol. Cell Biol.* 12(5):2391–5, 1992) and inserted into the EcoRV site of the KCR-KS vector to generate the KbpA vector.

To facilitate cloning of the human CAR cDNA insert into the KbpA vector, we introduced an annealed oligonucleotide consisting of restriction sites AvrII, StuI, BglII, EcoRV, and EcoRI downstream of the original EcoRI site and upstream of the bGHpA site to generate the KbpAlb vector. A XbaI-NotI (gap-filled), human CAR cDNA ("hCAR," 1.2 kilobases, GenBank Accession No. 458541) was then subcloned into the AvrII-EcoRV sites of the KbpAlb vector to obtain the KbpAlb-hCAR construct. A 2.5 kb HindIII-BamHI fragment consisting of KCR, hCAR cDNA, and bGHpA was then ligated into the corresponding sites of a modified bluescript 3'sk vector to yield vector KbpAlb-hCAR3'sk. The modified bluescript 3'sk vector that was used for this step contained unique eight base-pair clusters such as AscI, SwaI, and PacI cleavage sites that replaced the ClaI-Acc65I region in the 3' end of the original bluescript SK vector. Lastly, a 2.3 kb fragment containing the albumin promoter digested with NotI and BamHI (obtained from Ronald Evans, Xie et al., supra) was cloned into the NotI and BamHI sites of the KbpAlb-hCAR3'sk vector to obtain the Alb-hCAR transgenic construct. This plasmid contains an ampicillin resistance gene and the ColE1 origin of replication.

Example 10

Generation and Characterization of Humanized CAR Mice

For the generation of humanized CAR mice, fertilized one-celled embryos collected from C57BL/6 donor females mated with C57BL/6 males were collected in M2 media and microinjected with the linearized Alb-hCAR transgenic construct described above. The resulting mice were tested as described below to determine whether they expressed human CAR. The integration and retention of the transgenic construct in the mice was confirmed by standard Southern blotting analysis. For this analysis, genomic DNA was digested with BamHI and Asp718 and then probed with a 1 kb fragment containing the BamHI-EcoRI restriction enzyme-digested sequence encoding the human CAR ligand binding domain (LBD). The human LBD region was used as the probe because the LBD is the region that is the least homologous to murine CAR. The expected band of about 1.7 kb indicates that a mouse is a transgenic mouse containing the human CAR coding sequence (FIGS. 7A and 7C, * denotes lanes identified as containing DNA from a transgenic mouse). Nine transgenic founder mice were identified based on this analysis.

To further confirm that these transgenic mice contained DNA encoding human CAR, PCR analysis was performed. Primers hCAR-hinge5' (5'-CCGGAATTCAGGAAAGACATGATACTGTCGGCAGAAGCC-3', SEQ ID NO: 15) and hCAR3' (5'-cgcggatccGGCCGCTGCAGGCGCAGAACTGGTAGGTATGG-3', SEQ ID NO: 16) were used to specifically amplify the human CAR cDNA sequence and to generate a PCR product of 1000 base pairs (FIG. 7B). As a positive control, primers SCBF (5'-GAT GTG CTC CAG GCT AAA GTT-3', SEQ ID NO: 17) and SCBR (5'-AGA AAC GGA ATG TTG TGG AGT-3', SEQ ID NO: 18) were used to amplify endogenous mouse β-actin to produce a PCR product of 600 base pairs. This analysis confirmed that the nine founder mice contained human CAR DNA.

Four of the nine mice lines were also tested by Northern blot analysis to determine if they expressed human CAR mRNA transcripts of the expected size (~1.5 kb). For this analysis, cellular mRNA was probed with the same probe to the LBD region that was used for the Southern blot analysis. One of the mice lines, number 6210, expressed a human CAR mRNA transcript of the expected size (FIG. 8). The human CAR mRNA, which was under the control of the liver specific albumin promoter, was specifically expressed in the liver of this transgenic line. The other three lines appeared to express mRNA transcripts that were larger than the expected size. These larger mRNA transcripts may indicate rearrangement of the transgene or inappropriately-spliced structures. All of the four lines were analyzed for human CAR expression in at least the following organs: the liver, spleen, small intestine, and pancreas.

Example 11

Generation and Characterization of Humanized CAR Mice Lacking a Functional Endogenous Murine CAR Gene To test the function of the human CAR transgene in mice lacking the endogenous mouse CAR gene, mice from the transgenic line 6210 were first mated with mice homozygous for a mutation that inactivates the murine CAR gene. Male and female offspring from this mating that carried the 6210 transgene and were heterozygous for the murine CAR gene mutation were then mated. Among other genotypes, the offspring from such matings included animals homozygous for the murine CAR gene mutation and carrying the 6210 human CAR transgene, animals homozygous for the murine CAR gene mutation and lacking the 6210 human CAR transgene, and animals heterozygous for the murine CAR gene mutation and lacking the 6210 human CAR transgene.

As illustrated in FIG. 10, the response of these three groups of mice to two different xenobiotic inducers, phenobarbital (PB) and 1,4-bis-[2-(3,5,-dichloropyridyloxy)] benzene (TCPOBOP), was examined. Both of these inducers activate murine CAR, resulting in increased expression of the CYP2B10 gene. However, it is known that human CAR can be activated by PB, but not TCPOBOP (Tzameli et al., supra). In mice homozygous for the murine CAR gene mutation and lacking the human CAR transgene, no functional CAR is expressed and no response was observed to either inducer. Mice heterozygous for the murine CAR gene mutation and lacking the human CAR transgene express only murine CAR. These murine CAR expressing animals showed induction of CYP2B10 mRNA in response to both inducers. Mice homozygous for the murine CAR gene mutation and carrying the human CAR transgene express only human CAR in the liver. These human CAR expressing mice showed induction of CYP2B10 mRNA in response to PB, but did not respond to TCPOBOP.

These results demonstrate that the human CAR receptor maintains its activity and specificity when expressed in the mouse. In particular, the humanized CAR activates CAR target genes, such as CYP2B10. Mice expressing human CAR, but not murine CAR also induces a CAR target gene in response to the human CAR inducer PB, but did not in response to the murine CAR inducer TCPOBOP. These results further demonstrate the utility of mice expressing functional human CAR for the identification of compounds or treatments that specifically affect the activity of that receptor.

Example 12

CAR-Mediated Toxicity in CAR Knockout Mice

The effect of PB and the potent CAR agonist TCPOBOP on APAP toxicity was examined in wild-type and CAR knockout mice. Both strains of mice were treated with inducers or the vehicle control, followed by 250 mg/kg APAP. For these studies, mice were kept in a pathogen-free animal facility under standard 12 hour light/12 hour dark cycle and fed standard rodent chow and water ad libitum. At least five mice between 8 and 10 weeks old were used in each treatment group. For 3-day PB (100 mg/kg) treatment, mice were injected intraperitoneally three times, one injection per day. TCPOBOP (3 mg/kg) and/or APAP were injected intraperitoneally. Phenobarbital and TCPOBOP were suspended or dissolved in corn oil, and APAP was dissolved in basic PBS (pH=11). PB and APAP were purchased from Sigma (St Louis, Mo.); TCPOBOP was a gift from Dr. Stephen Safe.

For ALT measurements, blood was collected at different times as indicated and transferred to T-MGA tubes (Terumo Medical Corp., Elkton, Md.). Serum was isolated by centrifugation at 12,000×g for 10 minutes in 4° C. ALT activity was determined using Vitros ALT slides (Johnson & Johnson Ortho-Clinical Diagnostics, Rochester, N.Y.) at the Methodist Hospital, Houston, Tex.

For histologic examination of the treated mice, the left lobe of the livers was removed and immediately fixed in 4% formaldehyde-PBS solution, embedded in paraffin, sectioned at 5 μm, and stained with hematoxylin and eosin. Samples were examined under a light microscope. For RNA studies, total RNA was extracted using TRIzol Reagent (Invitrogen Life Technologies, Carlsbad, Calif.) according to the manufacture's instruction. Equivalent amount of RNA from 3–5 mice were pooled and 10 μg of each sample was subjected to northern blot analysis. All cDNA probes were prepared by RT-PCR with mouse liver RNA using SuperScript One Step RT-PCR system (Invitrogen Life Technologies, Carlsbad, Calif.). Preparation of probes for CYP2B10 and CYP3A11 were described as previously (Wei et al., *Nature* 407:920–923, 2000 and Zelko et al., *Mol Cell Biol* 21:2838–2846, 2001). PCR primers used were: CYP1A2: 5'-ccgcctctagagcggtttcttaccaata-3' (SEQ ID NO: 19) and 5'-ccgccggatccagccagagtaggcaaatct-3' (SEQ ID NO: 20), CYP2E1: 5'-ggatgaatatgccctacatg-3' (SEQ ID NO: 21) and 5'-tgatgggcagcaggtctcat-3' (SEQ ID NO: 22), GSTPi: 5'-acagaaactatgtgagcctg-3' (SEQ ID NO: 23) and 5'-atgggacggttcacatgttc-3' (SEQ ID NO: 24). Hepatic non-protein thiol was measured as an indication of hepatic GSH content. Mice were sacrificed two hours after intraperitoneal injection with APAP. Livers were removed and immediately homogenized in four volumes of 5% trichloroacetic acid and then centrifuged at 1,600×g for 15 minutes. Supernatant (0.5 ml) was mixed with 1.5 ml 0.1 mM Ellman's reagent [5,5'-dithiobis(2-nitrobenzoic acid)] (Sigma, St Louis, Mo.) and allowed to stand at room temperature for 15 minutes. Absorbance was read at 412 nm using GSH solutions as quantitative standards.

Based on the above analysis, neither the inducers alone nor the tested dose of APAP induced hepatotoxicity, as indicated by either the serum levels of the liver enzyme alanine amino transferase (ALT) or histologic examination.

In contrast, animals treated with either PB or TCPOBOP plus APAP showed strongly elevated ALT levels and hepatic necrosis at 24 hours (FIGS. 11A and 11B). The CAR null mice showed no such hepatotoxicity.

Among genes associated with APAP toxicity, PB or TCPOBOP treatment modestly suppressed CYP2E1 mRNA levels, but induced CYP1A2, CYP3A11 and GSTPi mRNAs in the wild-type animals (FIG. 11C). Neither the suppression of CYP2E1 nor the induction of the other enzymes was observed in the CAR null mice. The strong induction of GSTPi expression by PB or TCPOBOP treatments suggests that GSH depletion could contribute to the xenobiotic induced toxicity, and wild-type mice pretreated with PB or TCPOBOP showed an approximately 50% decrease in hepatic GSH two hours after APAP administration (FIG. 11D). To rule out the possibility that the CAR knockout animals are somehow resistant to NAPQI, the metabolite was directly injected into the livers of both wild-type and CAR null mice, and serum ALT levels were increased 5 to 10 fold in both. Thus, that both increased NAPQI production and GSH depletion may contribute to xenobiotic induced APAP toxicity.

To determine whether CAR null mice were also resistant to toxic doses of APAP, wild-type and knockout animals were treated with the analgesic at 500 mg/kg and 800 mg/kg. At either 5 or 24 hours, the CAR knockout animals showed significantly lower serum ALT levels than the wild-type animals (FIG. 12A). This resistance suggests that the CAR null animals may lack a xenobiotic response to the drug itself. To avoid complications associated with the extensive necrosis observed at later times, CYP1A2, CYP3A11, and GSTPi expression was examined two hours after administration of 500 mg/kg APAP. Even at this early time, expression of all three mRNAs was increased in wild-type, but not CAR null mice (FIG. 12B). The resistance of the CAR null animals to APAP toxicity was also demonstrated by the absence of the initial stages of both hepatocellular damage and GSH depletion observed with the wild-type animals (FIGS. 15A and 15B). Thus, loss of CAR function results in resistance to APAP toxicity that is associated with the absence of the induction of APAP metabolizing enzymes. Since neither APAP nor NAPQI functions as a CAR agonist, this activation may be similar to that of PB, which is based on induction of nuclear translocation, rather than direct ligand binding.

Example 13

Human CAR-Mediated APAP Toxicity

To determine whether human CAR is also involved in APAP sensitivity, CAR humanized animals that are homozygous for the human CAR transgene and the murine CAR mutation were treated with the general CAR activator PB induced expression of CYP1A2 and CYP3A11 mRNAs, and resulted in increased sensitivity to APAP (FIG. 13). Treatment of the humanized mice with 500 mg/kg of APAP also increased expression of CYP1A2, CYP3A11 and GSTPi, indicating that human CAR is activated by APAP (FIG. 16B).

Transactivation by mouse CAR, but not human CAR, can be blocked by the inverse agonist androstanol. Androstanol treatment not only prevents induction, but also decreases basal expression of CAR target genes, including CYP3A11. Androstanol pretreatment decreases APAP toxicity in wild-type mice. To determine whether androstanol administration following APAP treatment has a similar effect, single intraperitoneal injections of androstanol (100 mg/kg, dissolved or suspended in corn oil) were given at various times after administration of 500 mg/kg APAP to wild-type or CAR null mice. This 5α-androstan-3α-ol (androstanol) was purchased from Steraloids (Newport, R.I.). For comparison, N-acetylcysteine (1 g/kg, purchased from Sigma and dissolved in PBS) was administered intraperitoneally to other mice. Wild-type mice treated with the inverse agonist one hour after APAP showed a nearly complete absence of hepatotoxicity (FIGS. 14A and 14B). This remarkable hepatoprotective effect is mediated by CAR, because androstanol treatment did not block toxicity in identically treated CAR knockout animals (FIGS. 14A and 14B). Even at three hours after APAP treatment, when modest levels of hepatic necrosis are already evident in APAP treated mice (FIG. 15A), androstanol treatment of the wild-type mice resulted in somewhat lower serum ALT levels relative to untreated wild-type animals. The protective effect of androstanol at one and three hours was very similar to that of the antioxidant N-acetylcysteine, which is used therapeutically to treat APAP overdose (FIG. 17). The serum ALT levels in the CAR (−/−) animals treated with both androstanol and APAP were somewhat higher than those of the CAR nulls treated with APAP alone (FIG. 14A). Since androstanol is reportedly a weak PXR agonist (Moore et al., J Biol Chem 275:15122–15127, 2000), this increase may be due to an activation of PXR that becomes evident in the absence of functional CAR. Treatment of wild-type mice with the strong PXR agonist 5-pregnen-3b-ol-20-one-16a-carbonitrile (PCN) resulted in an increase in sensitivity to APAP comparable to that observed with TCPOBOP pretreatment. Relative to the wild-type control, androstanol treatment had no protective effect when administered five hours after APAP treatment.

Thus, CAR is a central mediator of APAP toxicity in mice and humans. CAR is apparently not involved in the toxicity associated with the ethanol dependent induction of CYP2E1 and other targets (Kostrubsky et al., supra and Sinclair et al., supra) since CAR activation modestly decreases CYP2E1 mRNA levels. However, activation of either mouse or human CAR by appropriate inducers, including APAP itself, results in increased production of APAP metabolizing enzymes and increased toxicity. Fatal outcomes have been reported for the combination of PB and APAP in humans. Current therapeutic approaches to APAP toxicity are primarily based on treatments with reducing agents to replenish GSH levels. The results described herein support the use of CAR inverse agonists as inhibitors of CAR-mediated toxicity in mammals (e.g., humans). Thus, potent and specific inverse agonists for human CAR provide a clinically useful means to treat toxicity of APAP or other hepatotoxic agents.

Other Embodiments

From the foregoing description, it will be apparent that variations and modifications may be made to the invention described herein to adopt it to various usages and conditions. Such embodiments are also within the scope of the following claims.

All publications mentioned in this specification are herein incorporated by reference to the same extent as if each independent publication or patent application was specifically and individually indicated to be incorporated by reference.

What is claimed is:

1. A transgenic mouse whose genome comprises a transgene comprising a nucleic acid sequence encoding a human CAR receptor of SEQ ID NO: 2 or a functional variant thereof having at least about 95% sequence identity to SEQ ID NO: 2 operably linked to a promoter, wherein expression of said nucleic acid sequence results in the production of a human CAR receptor in the liver of said mouse, wherein the human CAR receptor induces expression of a CAR target gene.

2. The transgenic mouse of claim 1, wherein the genome of said mouse comprises a disruption of the endogenous mouse CAR receptor gene, wherein said mouse lacks production of functional endogenous mouse CAR receptor.

3. The transgenic mouse of claim 1, wherein said CAR target gene is CYP2B10 or CYP2B6.

4. The transgenic mouse of claim 1, wherein said CAR target gene is CYP2B10.

5. The transgenic mouse of claim 1, wherein said CAR target gene is CYP3A11 or CYP3A4.

6. The transgenic mouse of claim 1, wherein said human CAR receptor is contacted with acetaminophen.

7. The transgenic mouse of claim 1, wherein said transgene further comprises a bovine growth hormone polyadenylation sequence.

8. The transgenic mouse of claim 1, wherein said transgene further comprises an intronic sequence of a rabbit β-globin gene.

9. The transgenic mouse of claim 8, wherein said intronic sequence is capable of increasing the expression of said human CAR receptor.

10. The transgenic mouse of claim 1, wherein said transgenic mouse exhibits an induction of a xenobiotic response in the presence of a xenobiotic inducer.

11. The transgenic mouse of claim 10, wherein the xenobiotic response induces or activates of the CAR target gene.

12. The mouse of claim 11, wherein said CAR target gene is CYP2B10.

13. The transgenic mouse of claim 11, wherein said xenobiotic inducer is phenobarbitol.

14. The transgenic mouse of claim 10, wherein the genome of said mouse comprises a disruption of the endogenous mouse CAR receptor gene, wherein said mouse lacks production of a functional endogenous mouse CAR receptor.

* * * * *

UNITED STATES PATENT AND TRADEMARK OFFICE

CERTIFICATE OF CORRECTION

PATENT NO. : 7,186,879 B2
APPLICATION NO. : 10/268822
DATED : March 6, 2007
INVENTOR(S) : David D. Moore et al.

It is certified that error appears in the above-identified patent and that said Letters Patent is hereby corrected as shown below:

Title Page, section (63) should read as follows:

This application is a continuation-in-part of International Application PCT/US01/29672, filed Sep. 21, 2001 and published in English, and a continuation-in-part of U.S. utility application Ser. No. 10/219,590, filed Aug. 15, 2002"."--,both of which claim priority to U.S. utility application Ser. No. 09/666,250, filed Sep. 21, 2000.--

In the Claims:

In Claim 11, line 2, delete "of".

In Claim 12, line 1, insert --transgenic-- between "The" and "mouse".

Signed and Sealed this

Seventeenth Day of April, 2007

JON W. DUDAS
*Director of the United States Patent and Trademark Office*